(12) United States Patent
Yen

(10) Patent No.: US 9,698,351 B2
(45) Date of Patent: Jul. 4, 2017

(54) ORGANIC MATERIAL FOR ELECTROLUMINESCENT DEVICE

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 271 days.

(21) Appl. No.: 14/698,860

(22) Filed: Apr. 29, 2015

(65) Prior Publication Data
US 2016/0322569 A1 Nov. 3, 2016

(51) Int. Cl.
H01L 51/00 (2006.01)
C07C 211/61 (2006.01)
C09K 11/06 (2006.01)
C07D 209/86 (2006.01)
C07D 307/91 (2006.01)
C07D 333/50 (2006.01)
C07D 307/77 (2006.01)
C07D 333/76 (2006.01)
(Continued)

(52) U.S. Cl.
CPC .......... H01L 51/006 (2013.01); C07C 211/61 (2013.01); C07D 209/80 (2013.01); C07D 209/86 (2013.01); C07D 307/77 (2013.01); C07D 307/91 (2013.01); C07D 333/50 (2013.01); C07D 333/76 (2013.01); C09K 11/06 (2013.01); H01L 51/0056 (2013.01); H01L 51/0061 (2013.01); H01L 51/0072 (2013.01); H01L 51/0073 (2013.01); H01L 51/0074 (2013.01); C07C 2103/54 (2013.01); C09K 2211/1007 (2013.01); C09K 2211/1011 (2013.01); C09K 2211/1014 (2013.01); C09K 2211/1022 (2013.01); C09K 2211/1029 (2013.01); C09K 2211/1088 (2013.01); C09K 2211/1092 (2013.01); H01L 51/5028 (2013.01)

(58) Field of Classification Search
CPC ...... H01L 51/006; C07C 211/61; C09K 11/06
USPC .......................................... 428/690
See application file for complete search history.

(56) References Cited

U.S. PATENT DOCUMENTS 8,962,160 B2  2/2015 Yen et al.
8,993,130 B2  3/2015 Yen et al.
(Continued)

FOREIGN PATENT DOCUMENTS

WO  2008062636 A1  5/2008
WO  2012091471 A2  7/2012

Primary Examiner — Mike M Dollinger

(57) ABSTRACT

The present invention discloses an organic material is represented by the following formula (1), the organic EL device employing the organic material as fluorescent emitting guest can display good performance like as lower driving voltage and power consumption, increasing efficiency and half-life time.

formula (1)

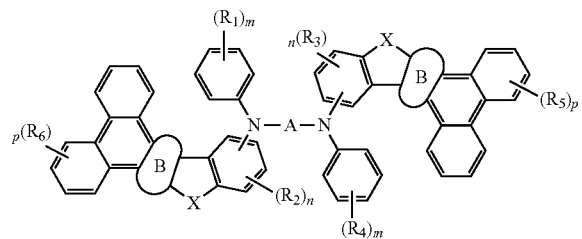

wherein A, B ring, X, m, n, p and $R_1$ to $R_6$ are the same definition as described in the present invention.

15 Claims, 1 Drawing Sheet

| 13 | — metal electrode |
| 12 | — electron injection layer |
| 11 | — electron transport layer |
| 10 | — hole blocking layer |
| 9 | — emitting layer |
| 8 | — hole transport layer |
| 7 | — hole injection layer |
| 6 | — transparent electrode |

(51) Int. Cl.
*C07D 209/80* (2006.01)
*H01L 51/50* (2006.01)

(56) References Cited

U.S. PATENT DOCUMENTS

| | | | |
|---|---|---|---|
| 9,048,437 B2* | 6/2015 | Yen | H01L 51/0068 |
| 2011/0073845 A1* | 3/2011 | Tseng | C09K 11/06 |
| | | | 257/40 |
| 2013/0048975 A1* | 2/2013 | Hong | C07D 209/80 |
| | | | 257/40 |
| 2014/0151645 A1 | 6/2014 | Yen et al. | |
| 2014/0175383 A1 | 6/2014 | Yen et al. | |
| 2014/0209866 A1 | 7/2014 | Yen et al. | |
| 2014/0231754 A1* | 8/2014 | Yen | H01L 51/0072 |
| | | | 257/40 |
| 2015/0333268 A1* | 11/2015 | Han | H01L 51/0073 |
| | | | 257/40 |
| 2016/0133844 A1* | 5/2016 | Kim | H01L 51/0054 |
| | | | 257/40 |
| 2016/0322569 A1* | 11/2016 | Yen | H01L 51/006 |

* cited by examiner

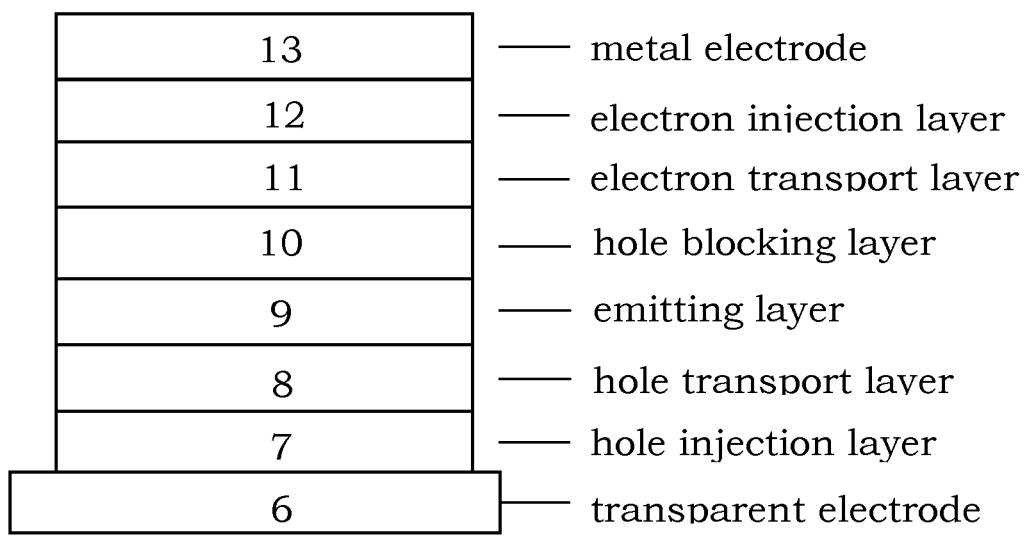

ORGANIC MATERIAL FOR ELECTROLUMINESCENT DEVICE

FIELD OF INVENTION

The present invention generally relates to an organic material and organic electroluminescent (herein referred to as organic EL) device using the organic material. More specifically, the present invention relates to the organic material having general formula (1), an organic EL device employing the organic material as fluorescent emitting guest of emitting layer.

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC).

For full-colored flat panel displays in AMOLED the material used for the fluorescent emitting layer are still unsatisfactory in half-lifetime, efficiency and driving voltage. In the present invention, for the purpose to prolong the half-life time and lower driving voltage for fluorescent guest in emitting layer for organic EL device, we employ an bis-(indenotriphenylene-phenylamine) skeleton link to naphthyl group, phenanthrenyl group, anthracenyl group, pyrenyl group, chrysenyl group, triphenylenyl group and perylenyl group to finish the organic material represented as general formula (1). The organic material show good thermal stability and charge carrier mobility for organic EL device. Indenotriphenylene skeleton based derivative disclosed in JP2013232520, KR20120072784, WO2008062636, WO2012091471, U.S. Pat. No. 8,962,160B2, U.S. Pat. No. 8,993,130B2, 20140231754A1 US20140151645A1, US20130048975A1, 20140175383A1 and US20140209866A1 are used for organic EL device are described. There are no prior arts demonstrate an bis-(indenotriphenylenephenylamine) skeleton link to naphthyl group, phenanthrenyl group, anthracenyl group, pyrenyl group, chrysenyl group, triphenylenyl group and perylenyl group used as fluorescent emitting guest for organic EL device.

According to the reasons described above, the present invention has the objective of resolving such problems of the prior-art and offering a light emitting device which is excellent in its thermal stability, high luminance efficiency, high luminance and long half-life time. The present invention disclose an organic material having general formula (1), used as a fluorescent emitting guest material have good charge carrier mobility and excellent operational durability can lower driving voltage and power consumption, increasing efficiency and half-life time of organic EL device.

SUMMARY OF THE INVENTION

In accordance with the present invention, the organic material and their use for fluorescent guest of emitting layer for organic EL device are provided. The organic material can overcome the drawbacks of the conventional materials like as shorter half-life time, lower efficiency, higher driving voltage.

An object of the present invention is to apply the organic material as fluorescent emitting guest for organic EL device and can lower driving voltage, lower power consumption and increase the efficiency.

The present invention has the economic advantages for industrial practice. Accordingly, the present invention discloses the organic material which can be used for organic EL device is disclosed. The mentioned the organic material is represented by the following formula (1)

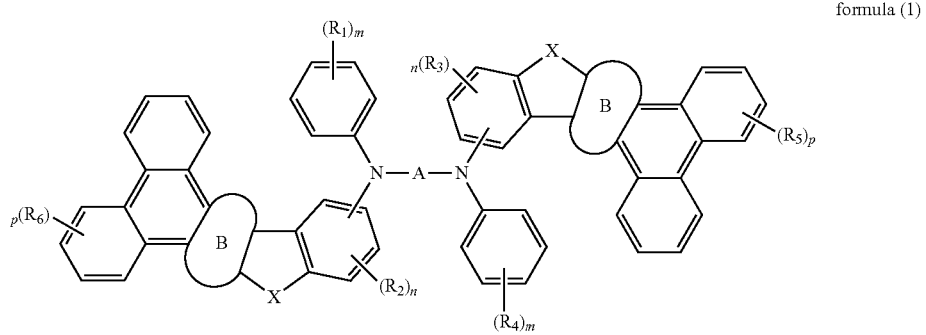

formula (1)

wherein A represents a substituted or unsubstituted fused ring hydrocarbon units with two to five rings, preferably A represents a substituted or unsubstituted naphthyl group, a substituted or unsubstituted phenanthrenyl group, a substituted or unsubstituted anthracenyl group, a substituted or unsubstituted pyrenyl group, a substituted or unsubstituted chrysenyl group, a substituted or unsubstituted triphenylenyl group and a substituted or unsubstituted perylenyl group, B ring represents a benzene ring and which is condensed with the adjacent rings in different manner; X represents a divalent bridge selected from the atom or group consisting from O, S, $C(R_7)(R_8)$ and $N(R_9)$, m represents an integer of 0 to 5, n represents an integer of 0 to 3, p represents an integer of 0 to 8, $R_1$ to $R_9$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

DESCRIPTION OF THE PREFERRED EMBODIMENTS

What probed into the invention is the organic material and organic EL device using the organic material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the organic material which can be used as fluorescent emitting guest for organic EL device are disclosed. The mentioned organic material represented by the following formula (1):

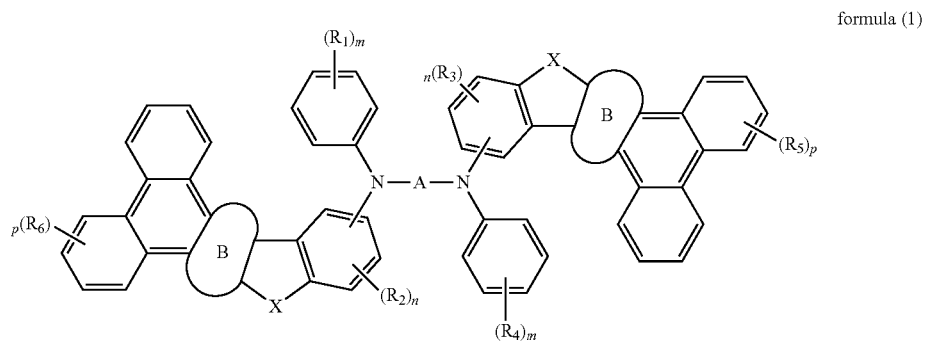

formula (1)

BRIEF DESCRIPTION OF THE DRAWINGS

FIG. 1 show one example of organic EL device in the present invention, and 6 is transparent electrode, 13 is metal electrode, 7 is hole injection layer which is deposited onto 6, 8 is hole transport layer which is deposited onto 7, 9 is fluorescent or phosphorescent emitting layer which is deposited onto 8, 10 is hole blocking layer which is deposited onto 9, 11 is electron transport layer which is deposited onto 10, and 12 is electron injection layer which is deposited on to 11.

wherein A represents a substituted or unsubstituted fused ring hydrocarbon units with two to five rings, preferably A represents a substituted or unsubstituted naphthyl group, a substituted or unsubstituted phenanthrenyl group, a substituted or unsubstituted anthracenyl group, a substituted or unsubstituted pyrenyl group, a substituted or unsubstituted chrysenyl group, a substituted or unsubstituted triphenylenyl group and a substituted or unsubstituted perylenyl group, B ring represents a benzene ring and which is condensed with the adjacent rings in different manner; X represents a divalent bridge selected from the atom or group consisting from O, S, C(R$_7$)(R$_8$) and N(R$_9$), m represents an integer of 0 to 5, n represents an integer of 0 to 3, p represents an integer of 0 to 8, R$_1$ to R$_9$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the organic material formula (1), wherein A is represented by the following formulas:

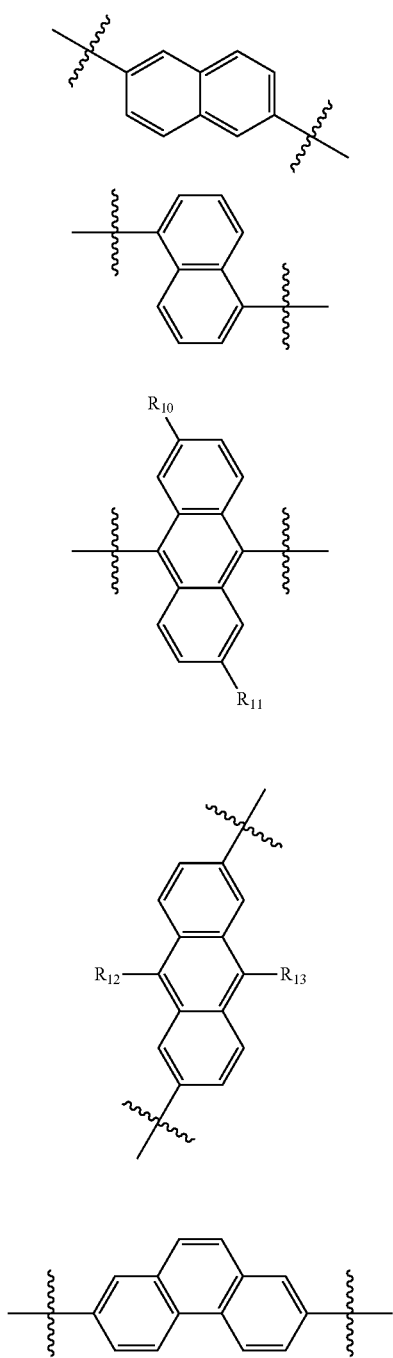

-continued

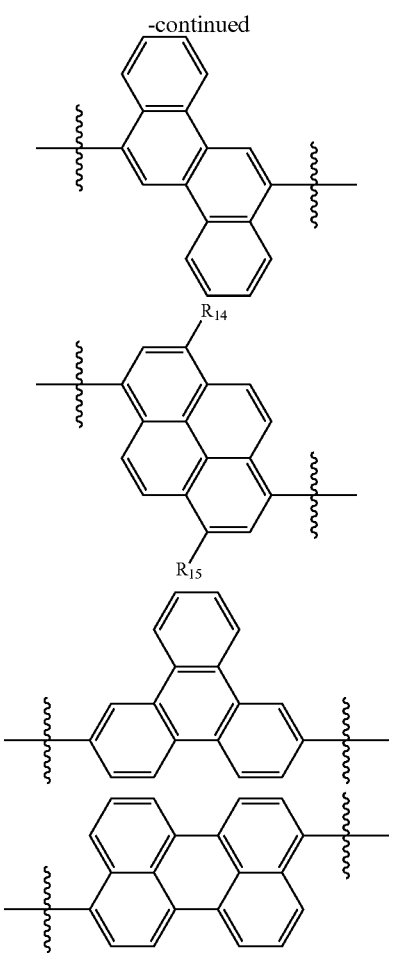

wherein R$_{10}$ to R$_{15}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the organic material formula (1), when m represents an integer of 1, preferably R$_1$ and R$_4$ are represented by the following formula (2); when m represents an integer of 2, and R$_1$ or R$_4$ are each independently in adjacent position, preferably R$_1$ and R$_4$ are represented by the following formula (3)

formula (2)

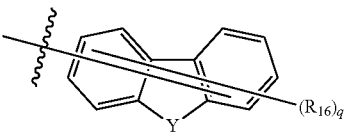

formula (3)

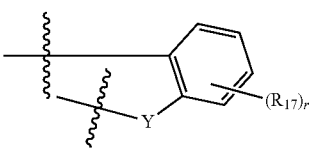

wherein Y represents a divalent bridge selected from the atom or group consisting from O, S and N(R$_{18}$), q represents an integer of 0 to 8, r represents an integer of 0 to 4, $R_{16}$ to $R_{18}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the organic material formula (1) represented by the following formula (4) to formula (6):

chrysenyl group, a substituted or unsubstituted triphenylenyl group and a substituted or unsubstituted perylenyl group, X represents a divalent bridge selected from the atom or group consisting from O, S, $C(R_7)(R_8)$ and $N(R_9)$, m represents an integer of 0 to 5, n represents an integer of 0 to 3, p represents an integer of 0 to 8, $R_1$ to $R_6$ are independently selected from the group consisting of a hydrogen atom, a substituted or unsubstituted alkyl group having 1 to 20 formula(4)

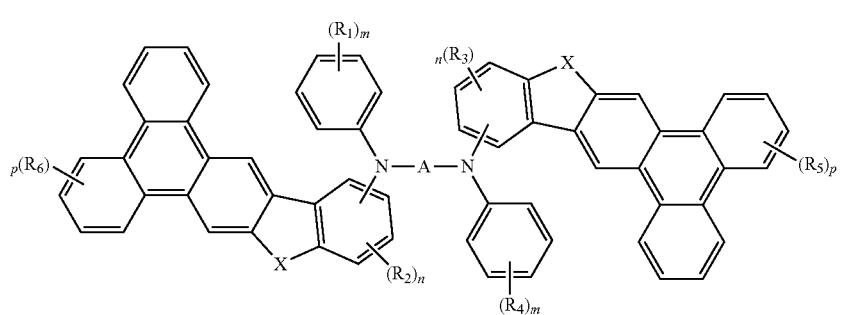

formula(5)

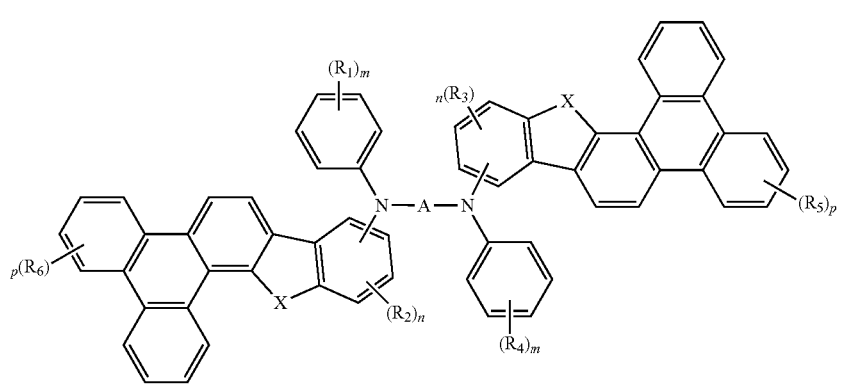

formula(6)

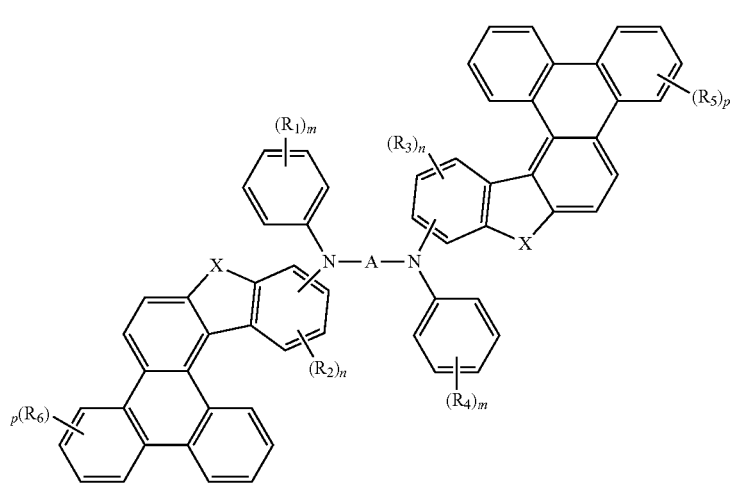

wherein A represents a substituted or unsubstituted fused ring hydrocarbon units with two to five rings, preferably A represents a substituted or unsubstituted naphthyl group, a substituted or unsubstituted phenanthrenyl group, a substituted or unsubstituted anthracenyl group, a substituted or unsubstituted pyrenyl group, a substituted or unsubstituted carbon atoms, a substituted or unsubstituted aryl group having 6 to 30 carbon atoms and a substituted or unsubstituted heteroaryl group having 3 to 30 carbon atoms.

According to the above-mentioned the organic material formula (4), to formula (6) wherein A is represented by the following formulas:

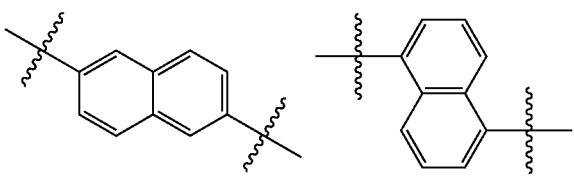

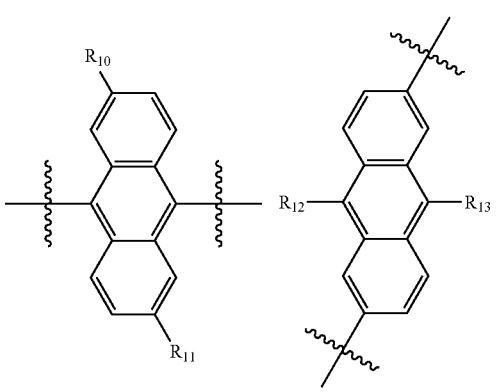

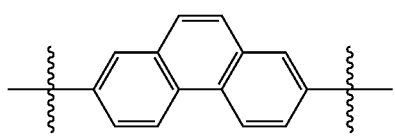

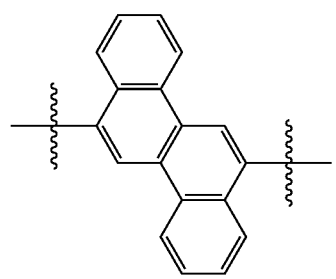

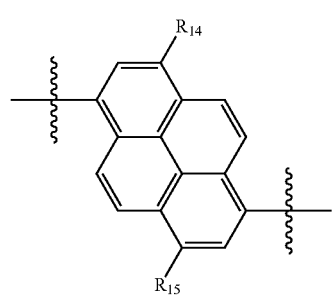

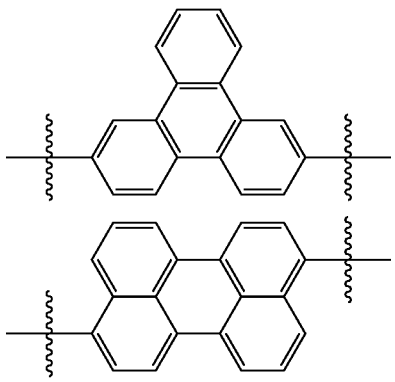

wherein $R_{10}$ to $R_{15}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the organic material formula (4) to formula (6), when m represents an integer of 1, preferably $R_1$ and $R_4$ are represented by the following formula (2); when m represents an integer of 2, and $R_1$ or $R_4$ are each independently in adjacent position, preferably $R_1$ and $R_4$ are represented by the following formula (3)

formula (2)

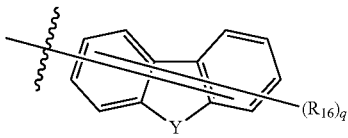

formula (3)

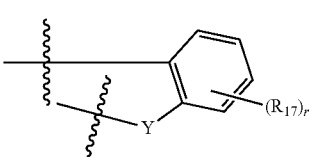

wherein Y represents a divalent bridge selected from the atom or group consisting from O, S and $N(R_{18})$, q represents an integer of 0 to 8, r represents an integer of 0 to 4, $R_{16}$ to $R_{18}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the organic material formula (4) to formula (6) represented by the following formula (7) to formula (18):

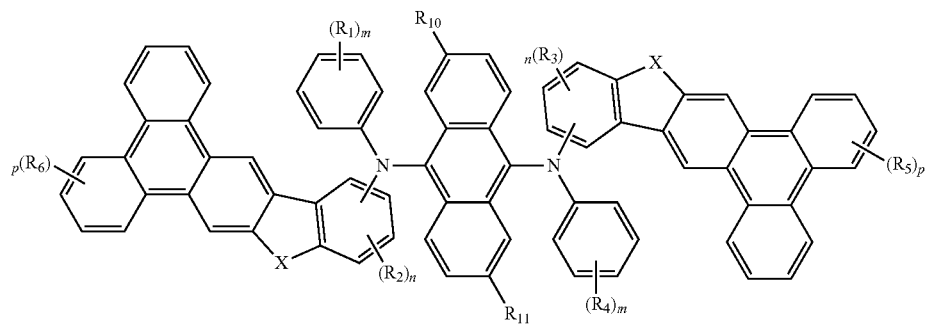
formula(7)
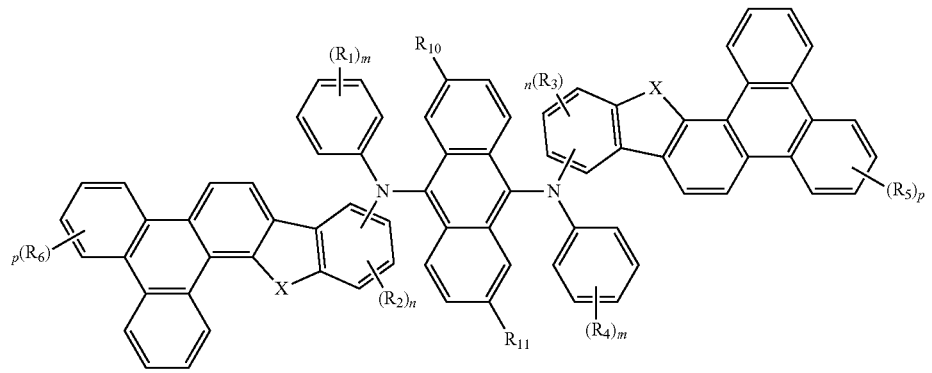
formula(8)
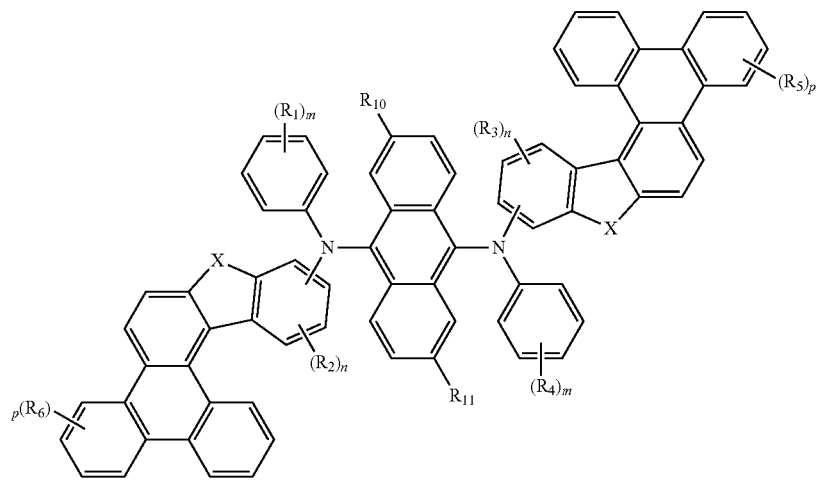
formula(9)
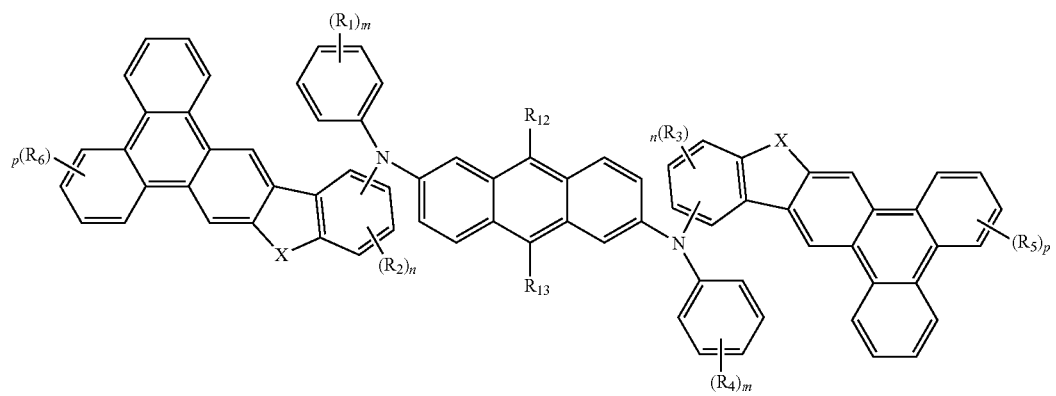
formula(10)

-continued
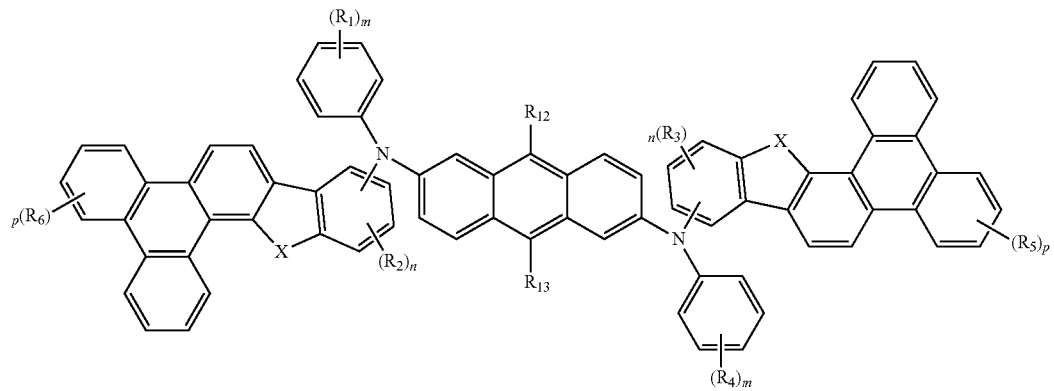
formula(11)
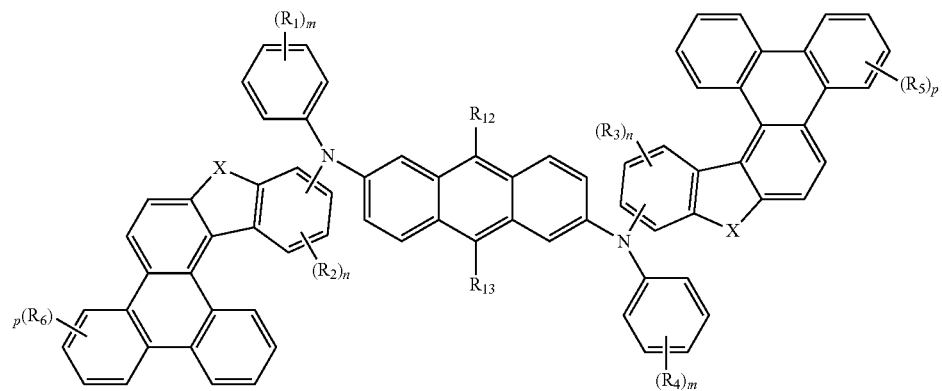
formula(12)
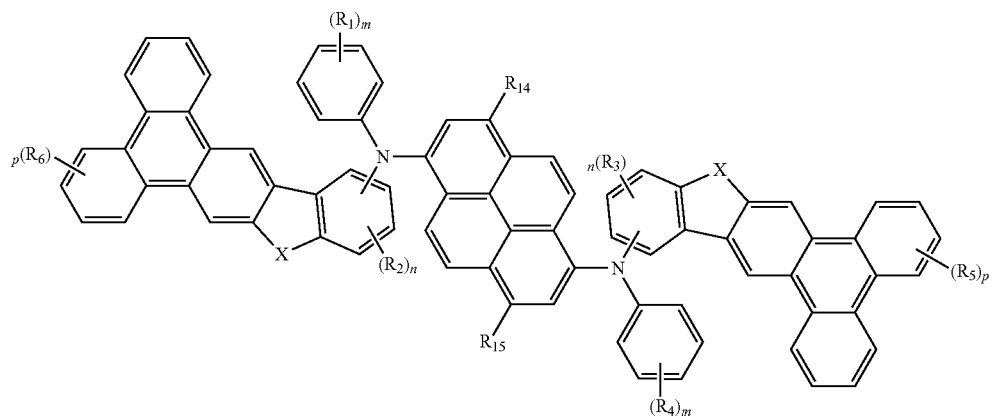
formula(13)
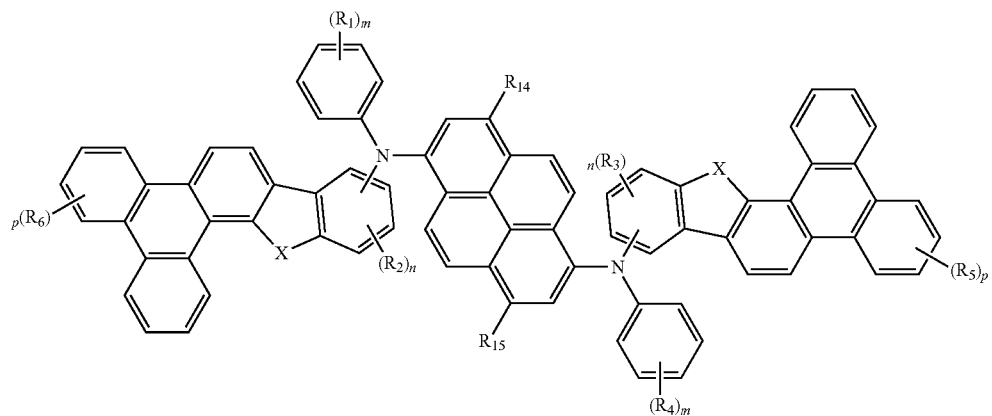
formula(14)

formula(15)
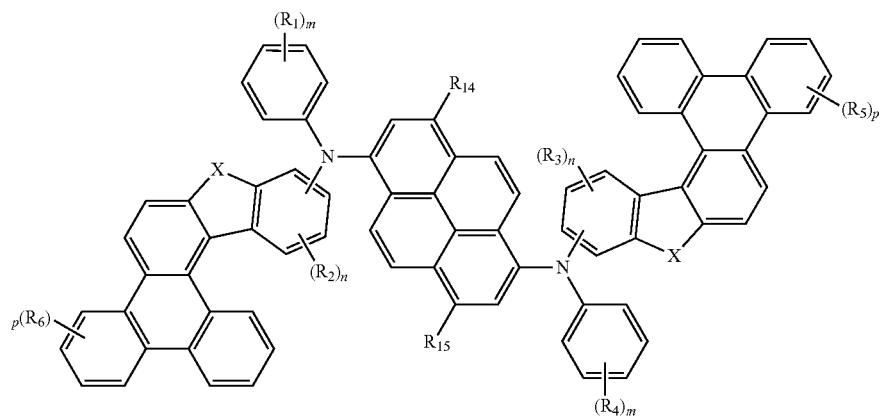
formula(16)
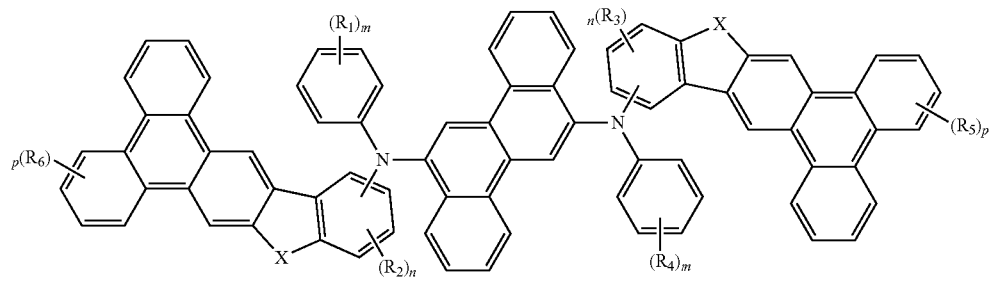
formula(17)
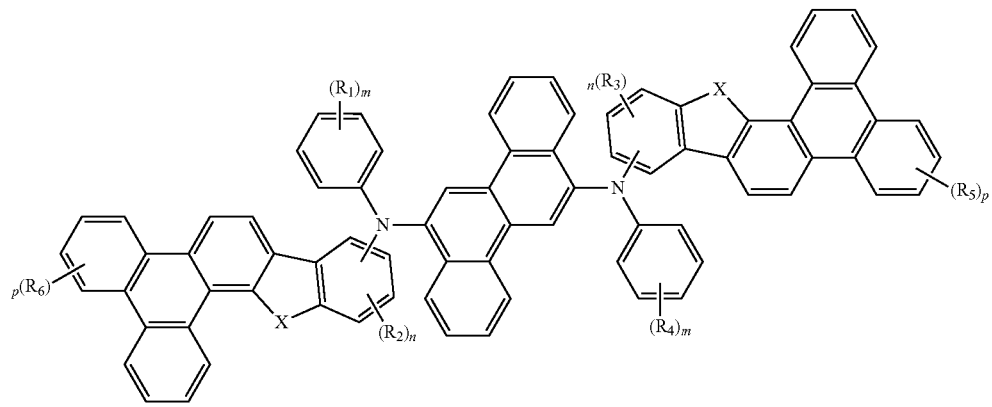
formula(18)
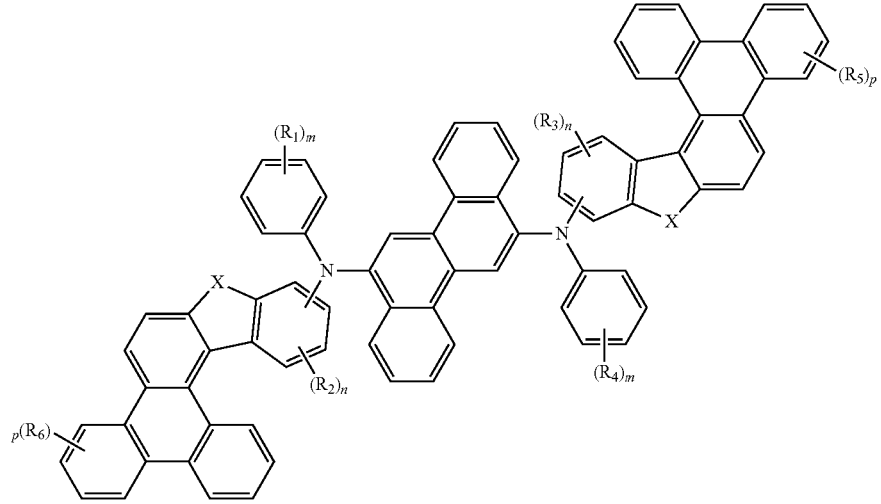

wherein X represents a divalent bridge selected from the atom or group consisting from O, S, $C(R_7)(R_8)$ and $N(R_9)$, m represents an integer of 0 to 5, n represents an integer of 0 to 3, p represents an integer of 0 to 8, $R_1$ to $R_{18}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the organic material formula (7) to formula (18), when m represents an integer of 1, preferably $R_1$ and $R_4$ are represented by the following formula (2); when m represents an integer of 2, and $R_1$ or $R_4$ are each independently in adjacent position, preferably $R_1$ and $R_4$ are represented by the following formula (3)

formula (2)

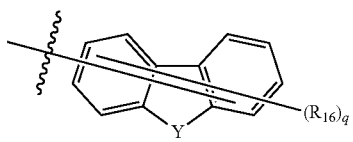

-continued formula (3)

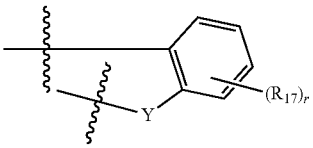

wherein Y represents a divalent bridge selected from the atom or group consisting from O, S and $N(R_{18})$, q represents an integer of 0 to 8, r represents an integer of 0 to 4, $R_{16}$ to $R_{18}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

In this embodiment, some organic material are shown below:

EX1

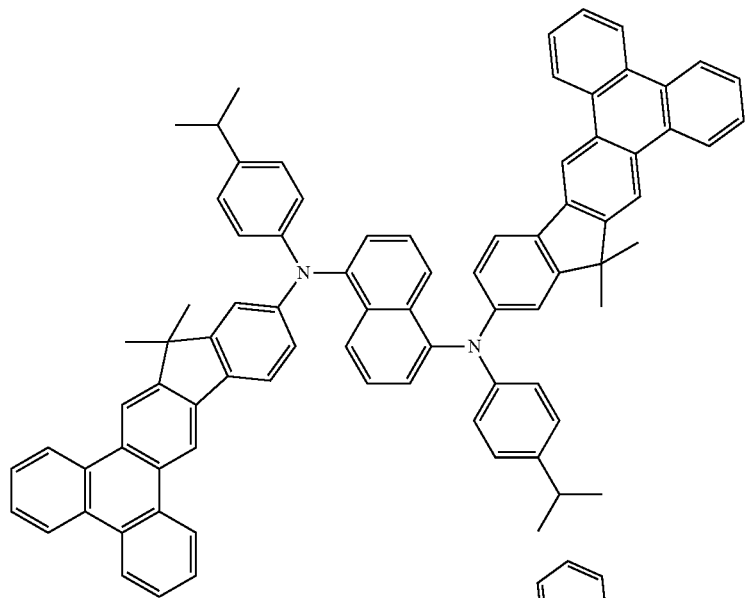

EX2

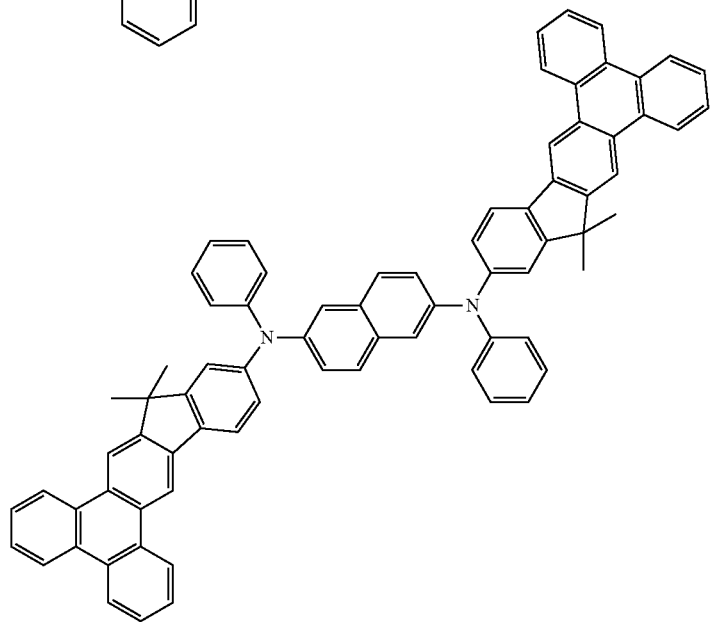

-continued
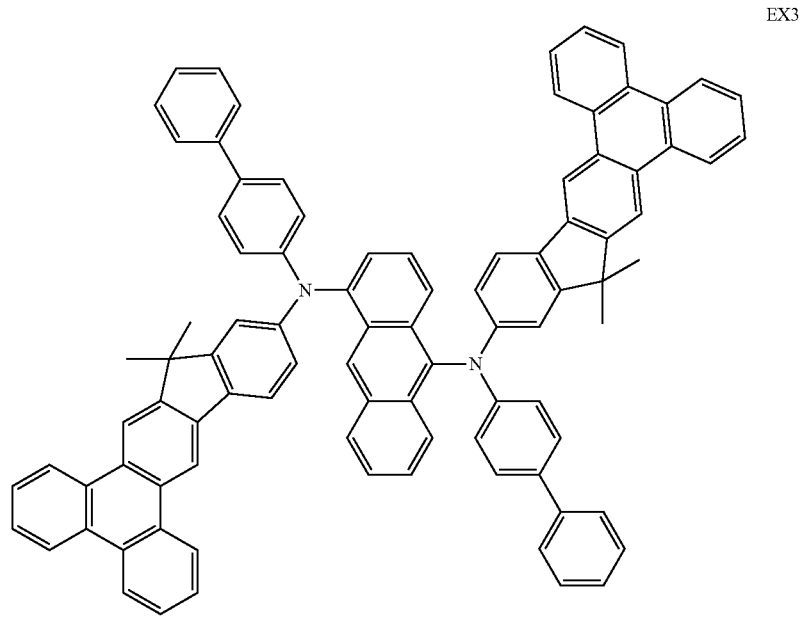
EX3
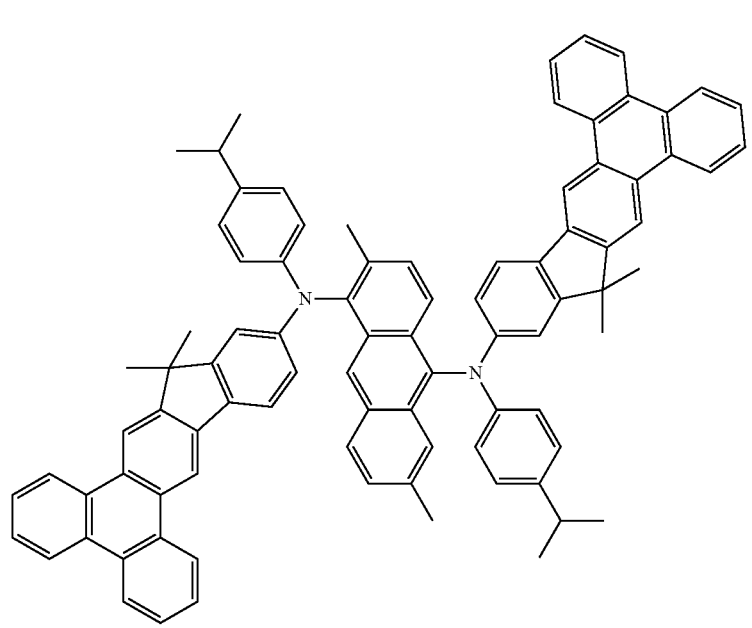
EX4

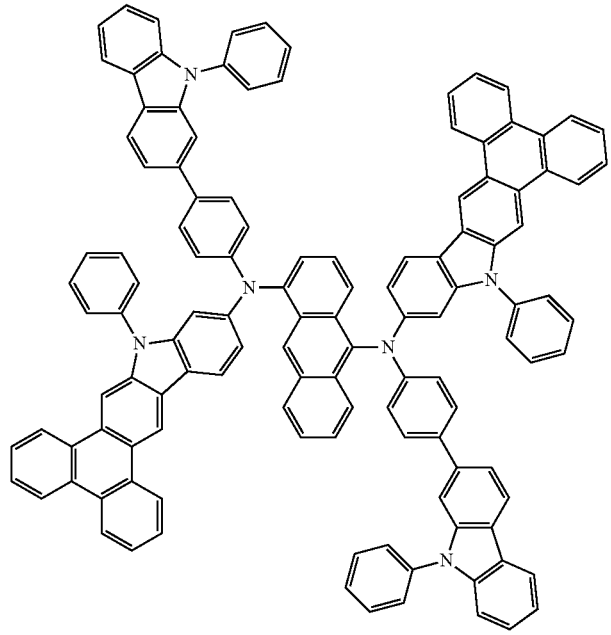
EX5
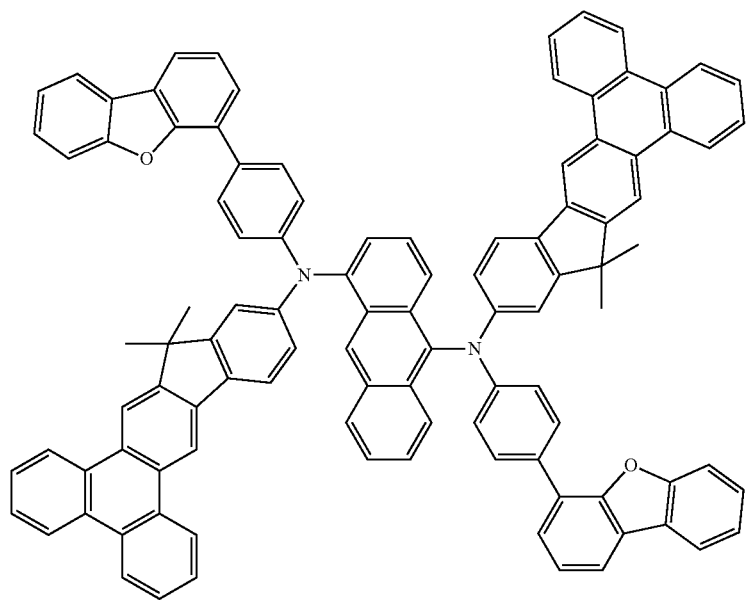
EX6

-continued
EX7
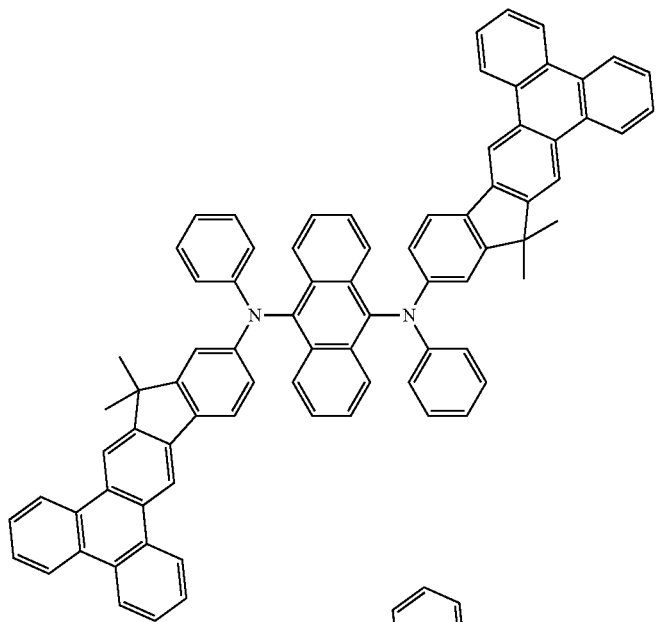
EX8
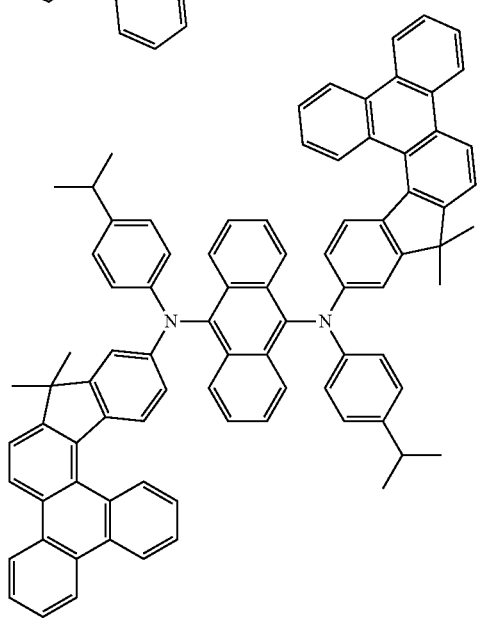
EX9
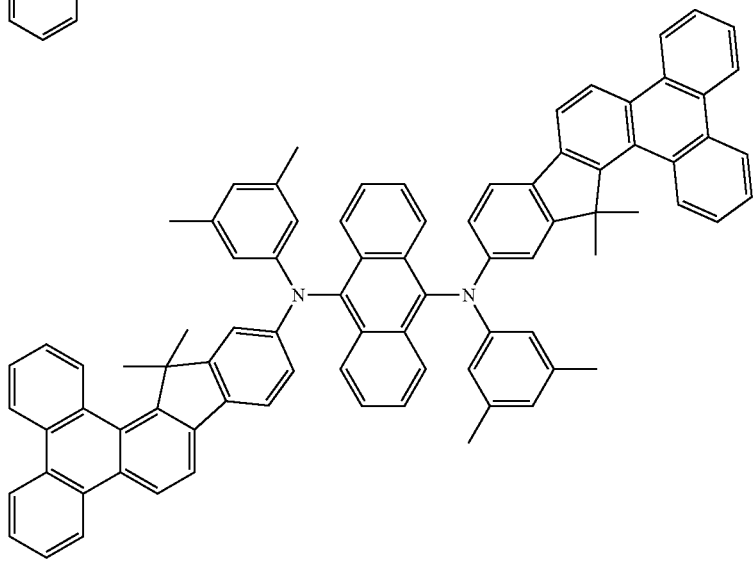

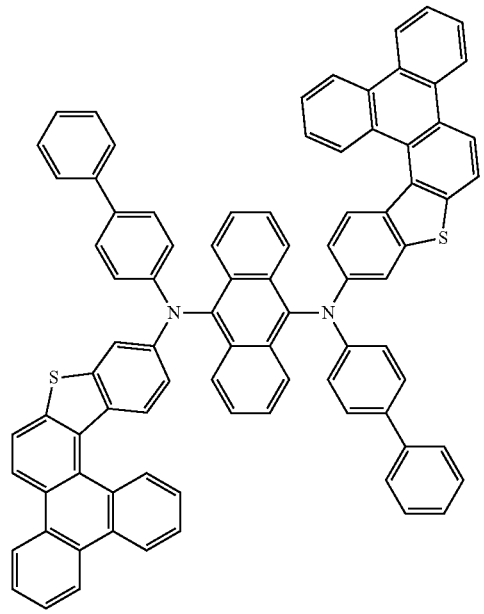
EX10
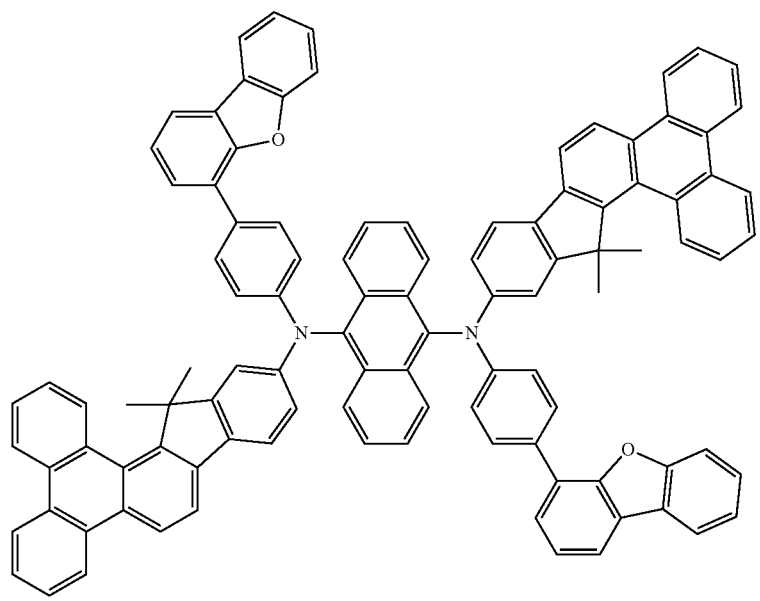
EX11

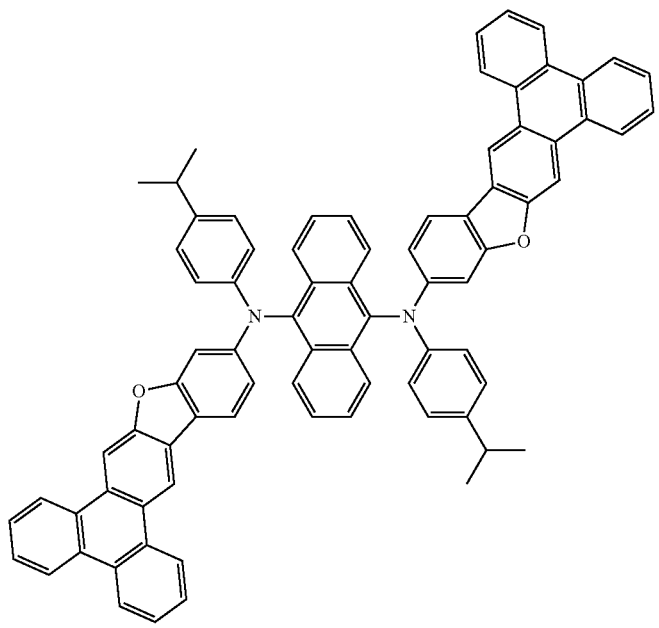
EX12
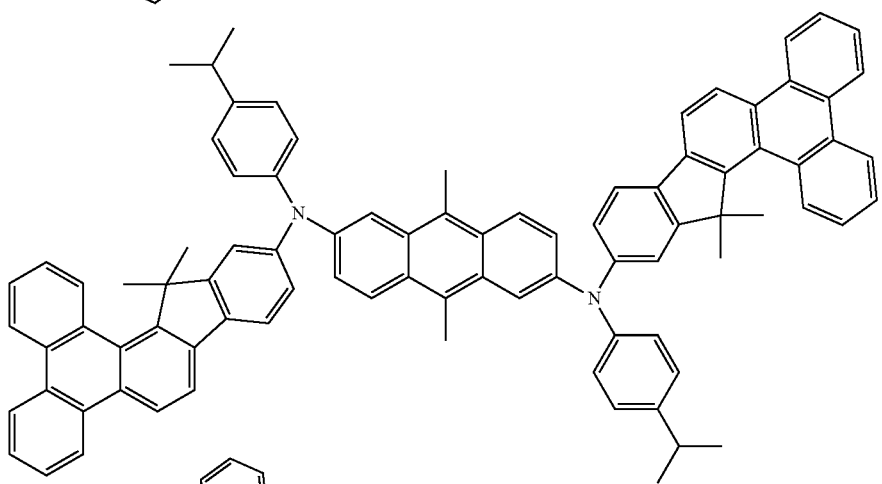
EX13
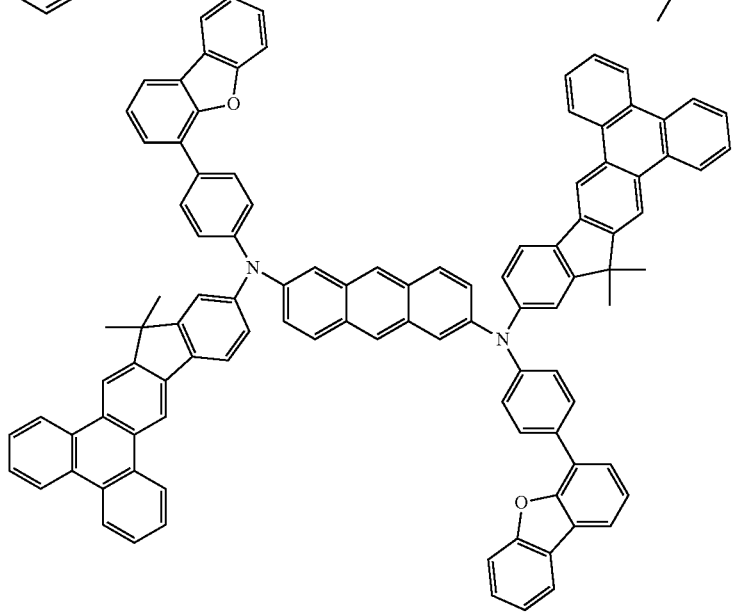
EX14

-continued
EX15
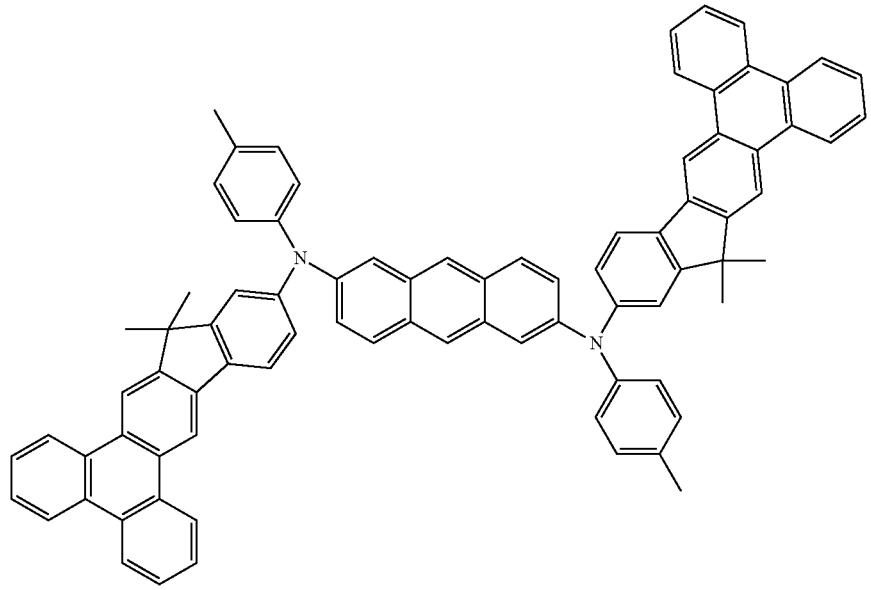
EX16
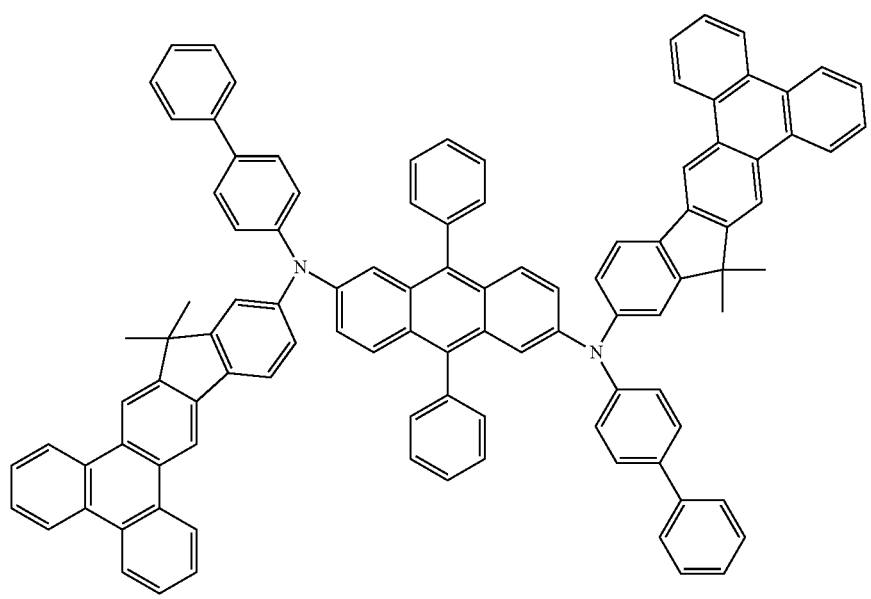
EX17
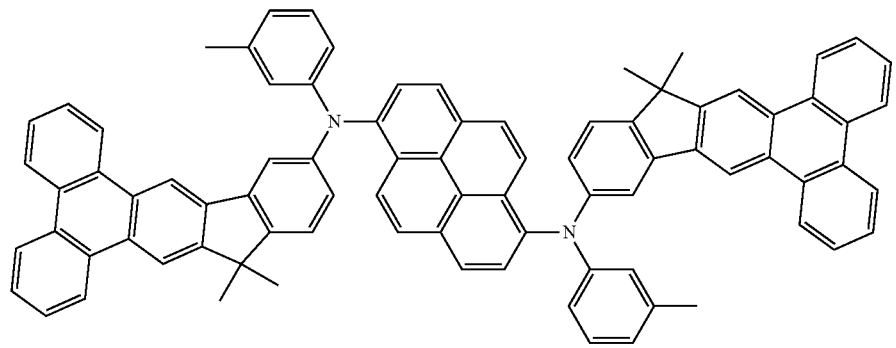

-continued
EX18
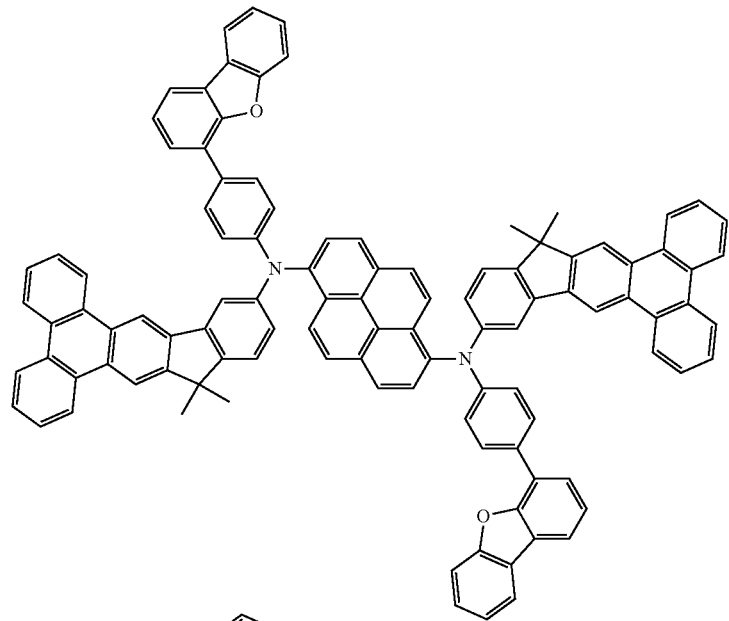
EX19
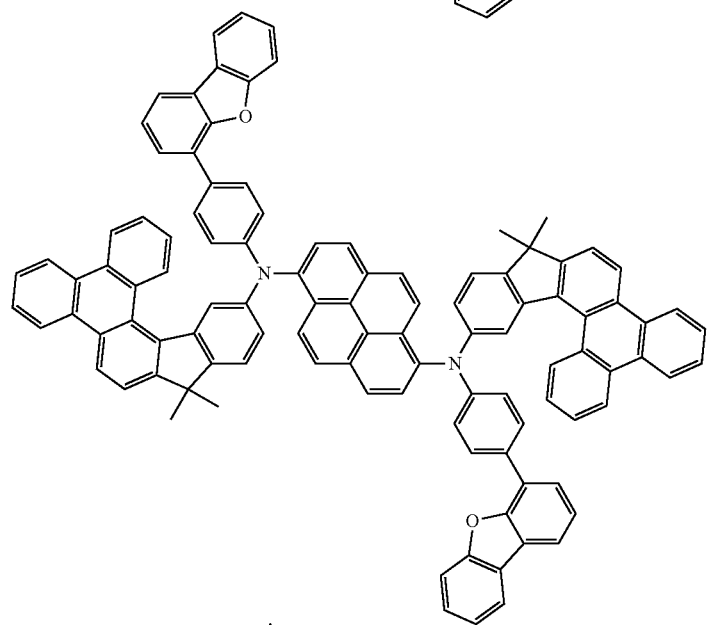
EX20
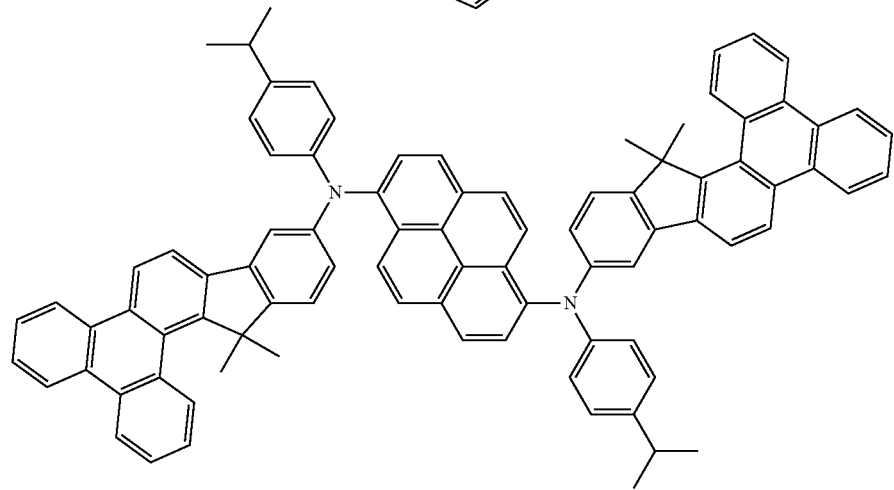

EX21
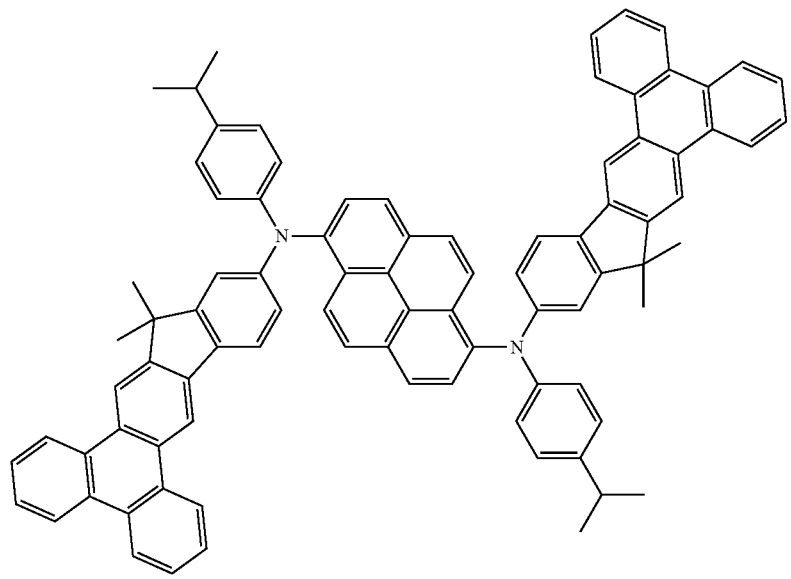
EX22
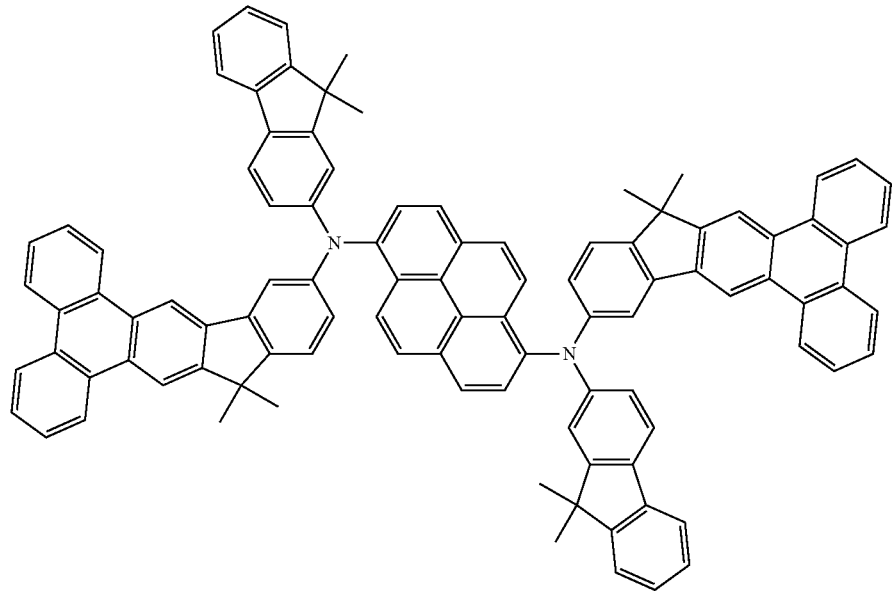
EX23
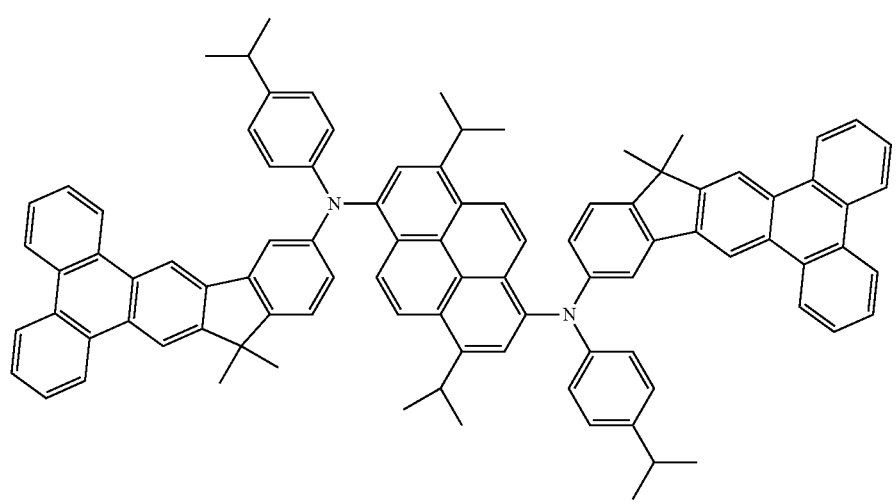

EX24
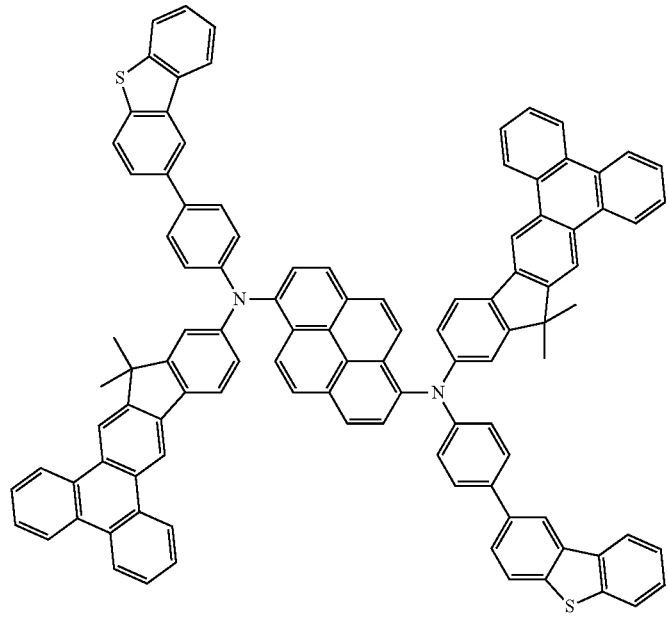
EX25
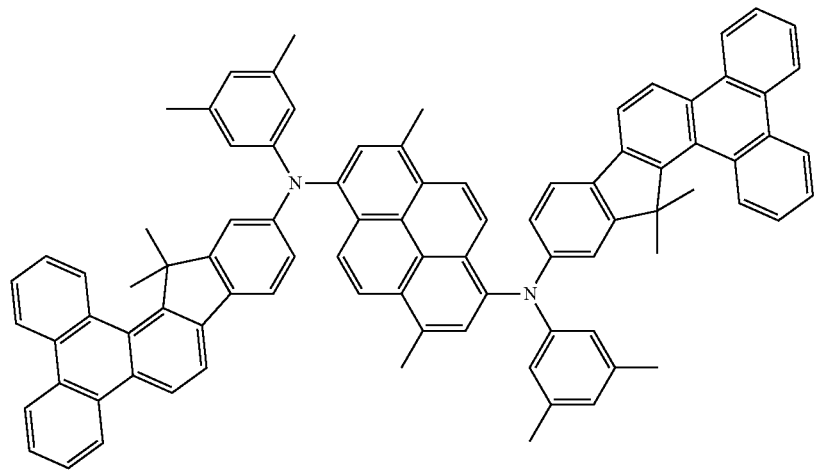
EX26
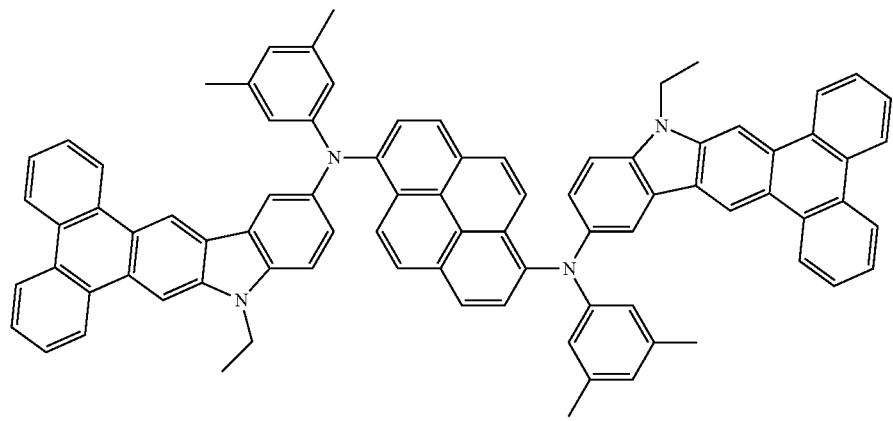

-continued
EX27
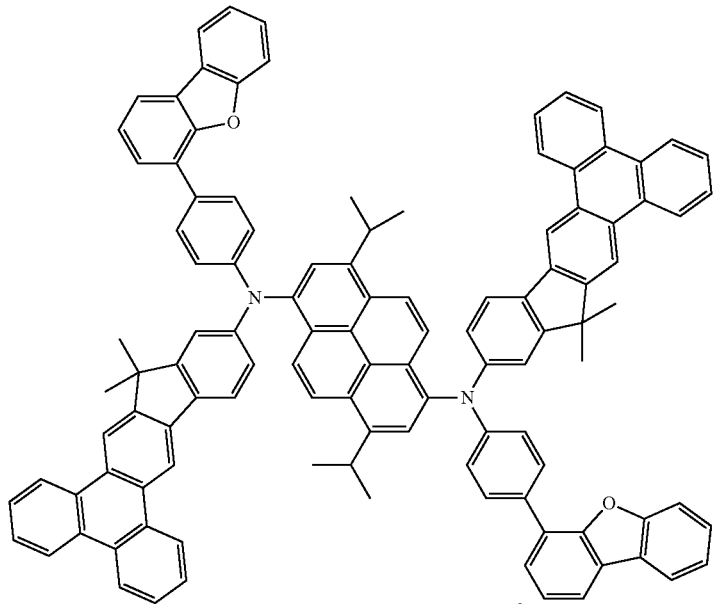
EX28
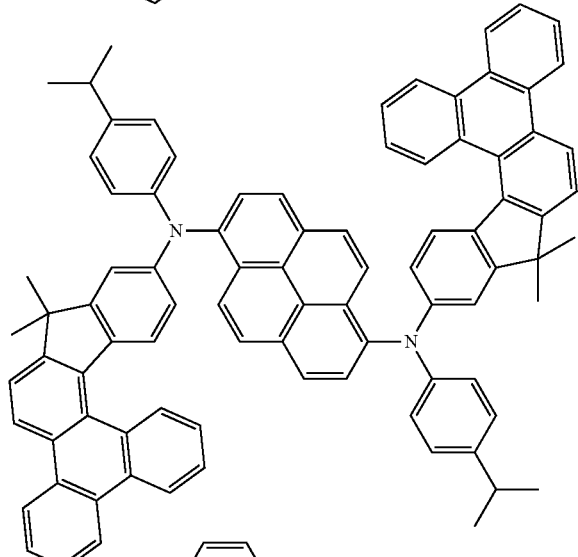
EX29
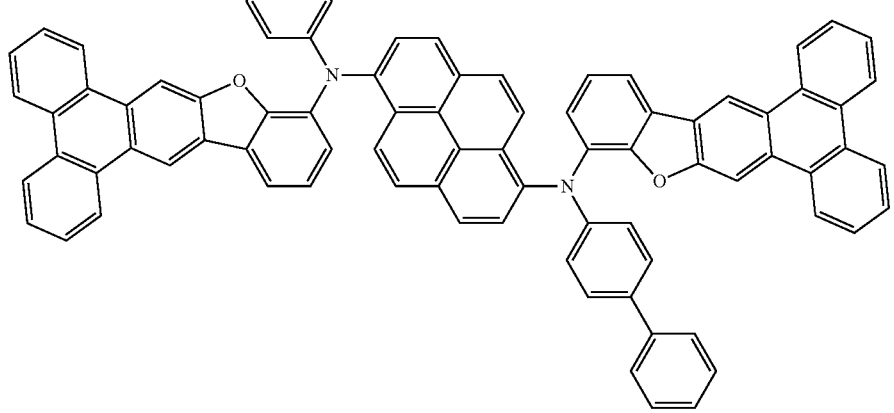

EX30
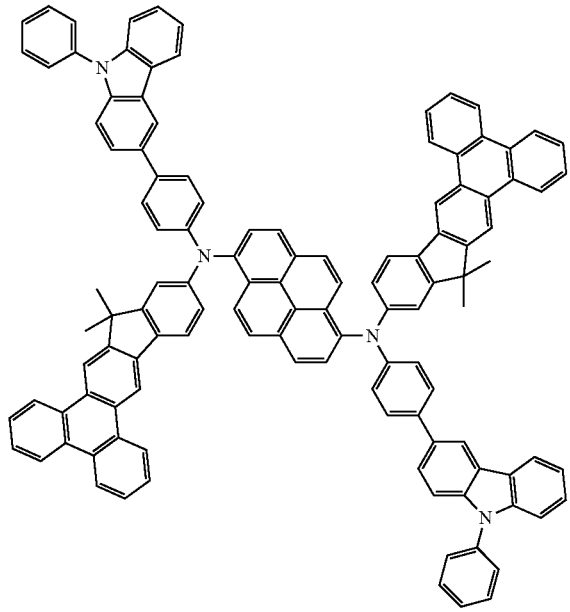
EX31
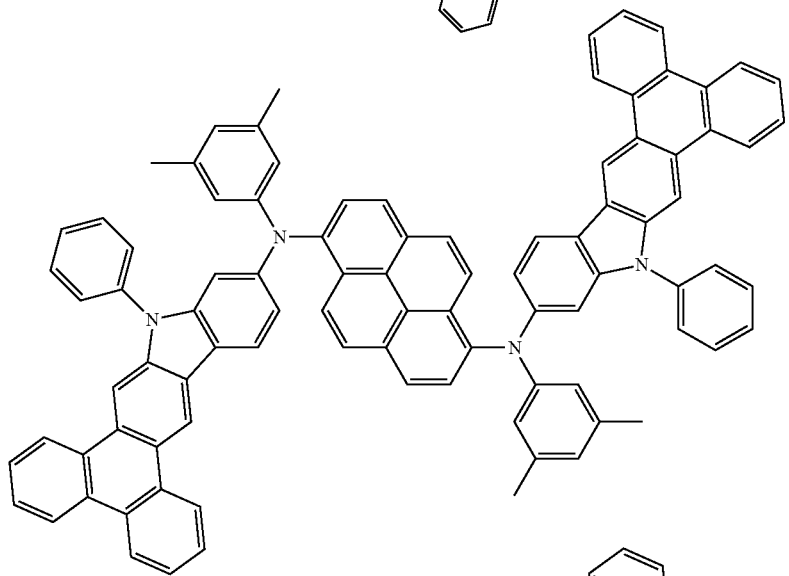
EX32
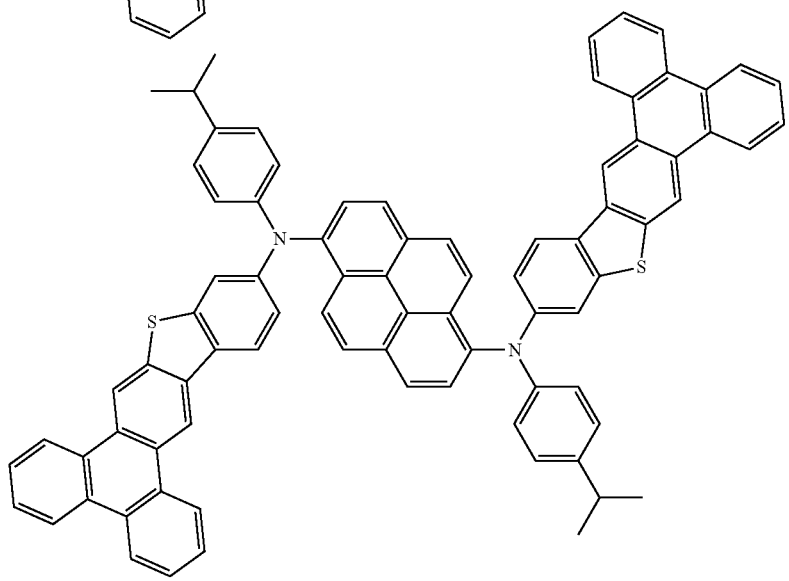

-continued
EX33
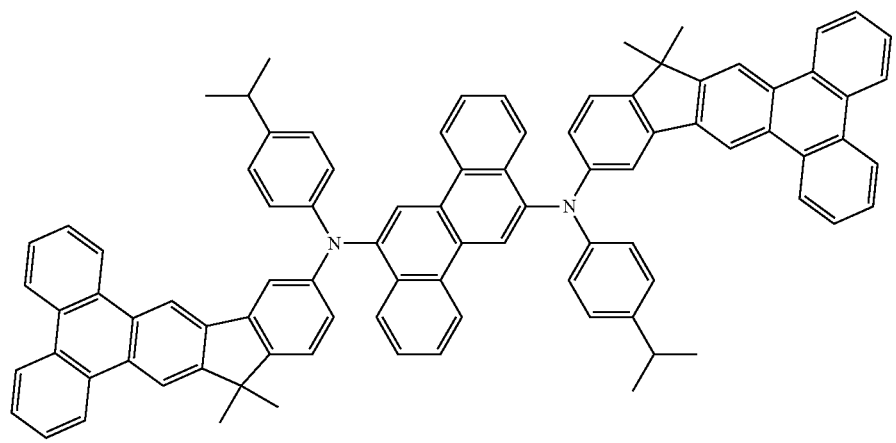
EX34
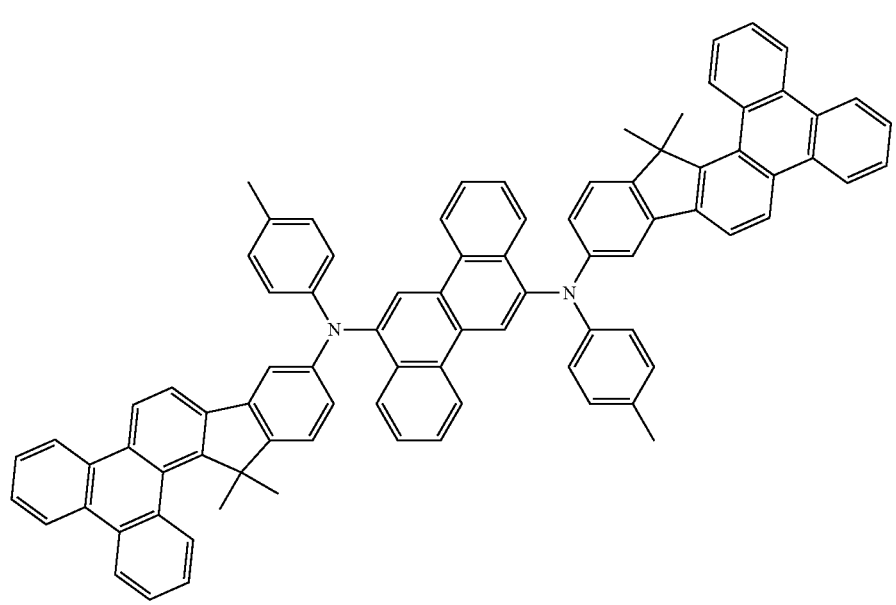
EX35
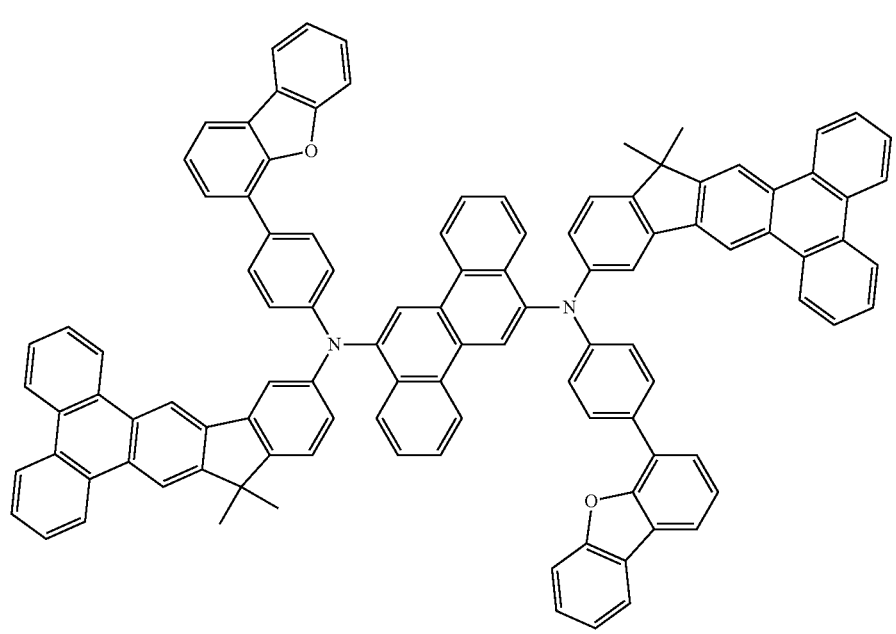

-continued
EX36
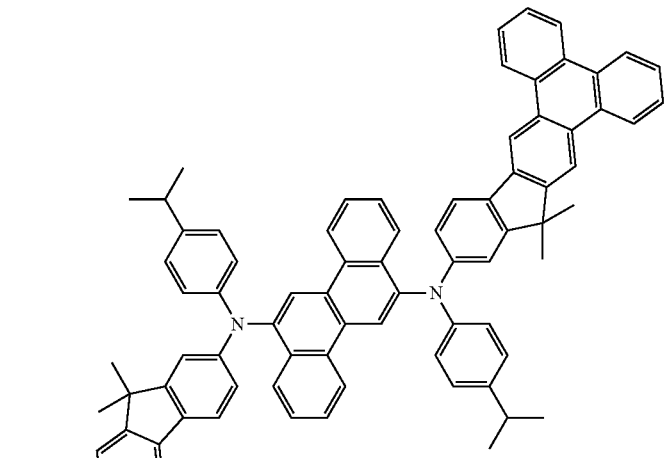
EX37
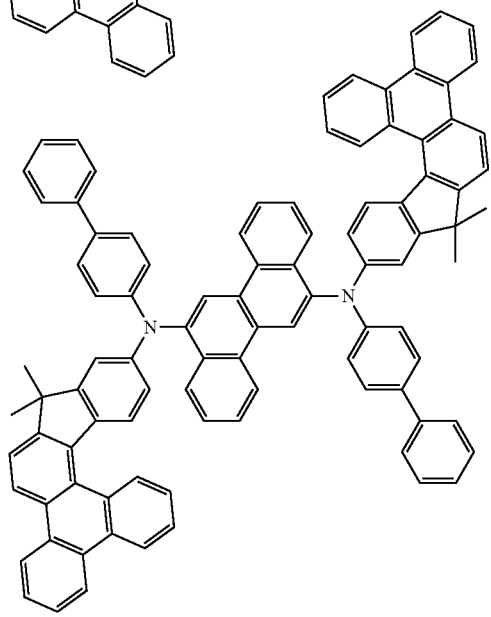
EX38
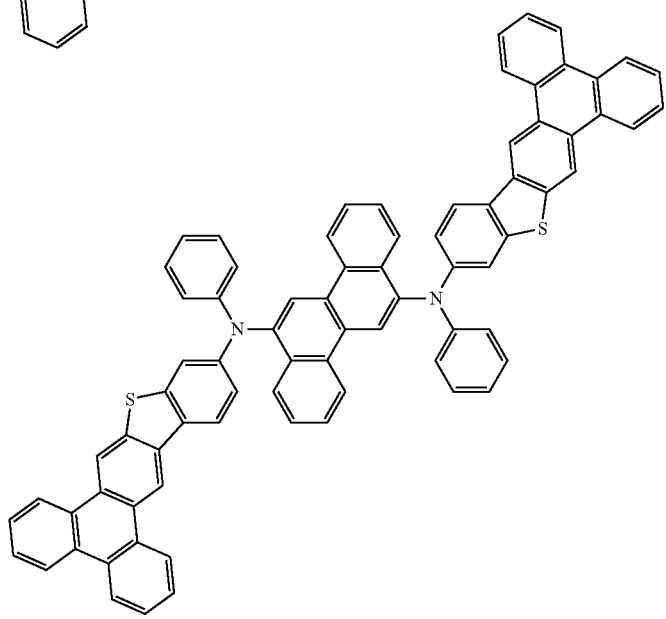

-continued
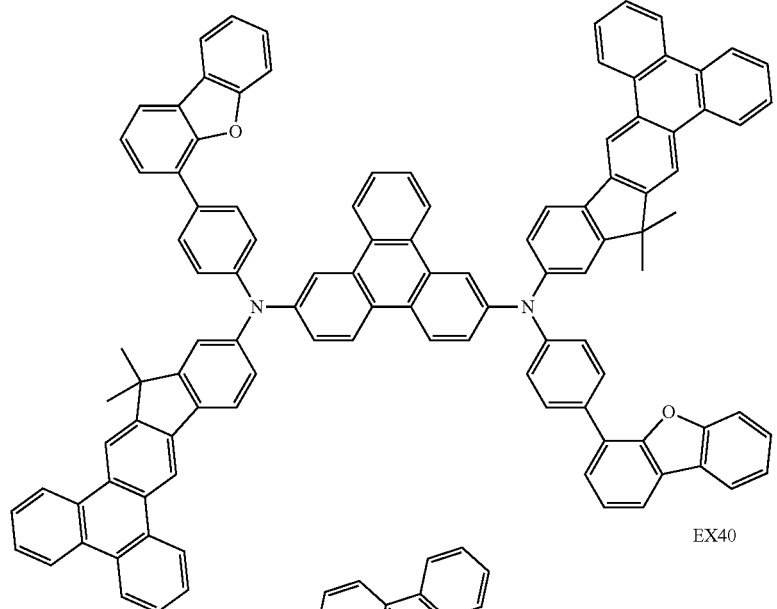
EX39
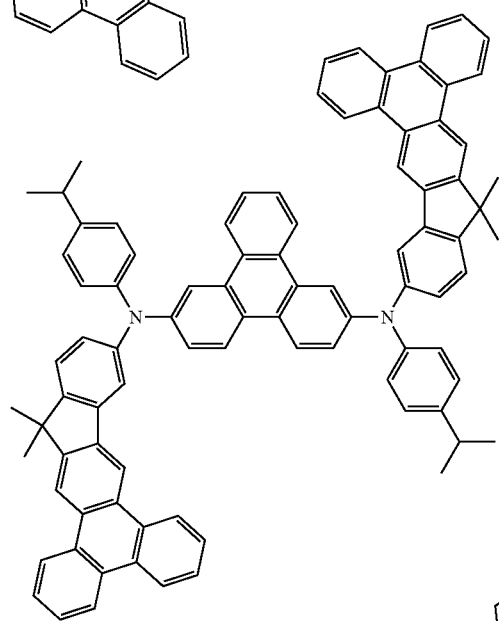
EX40
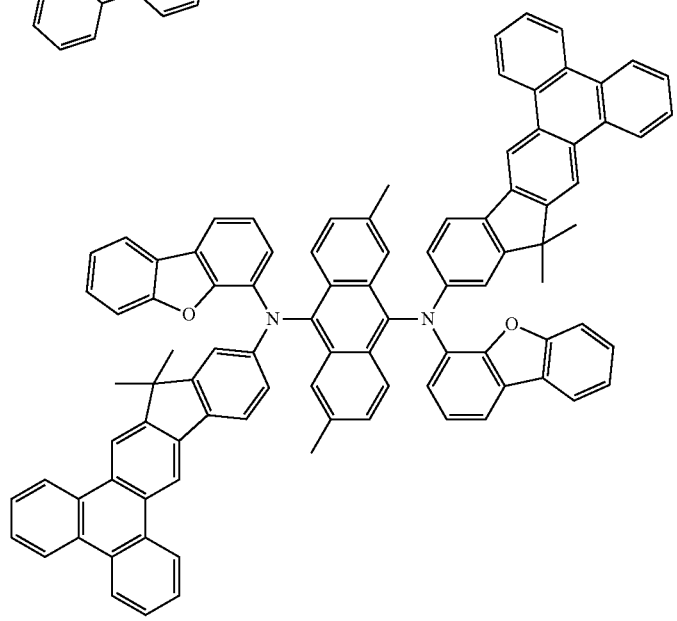
EX41

-continued
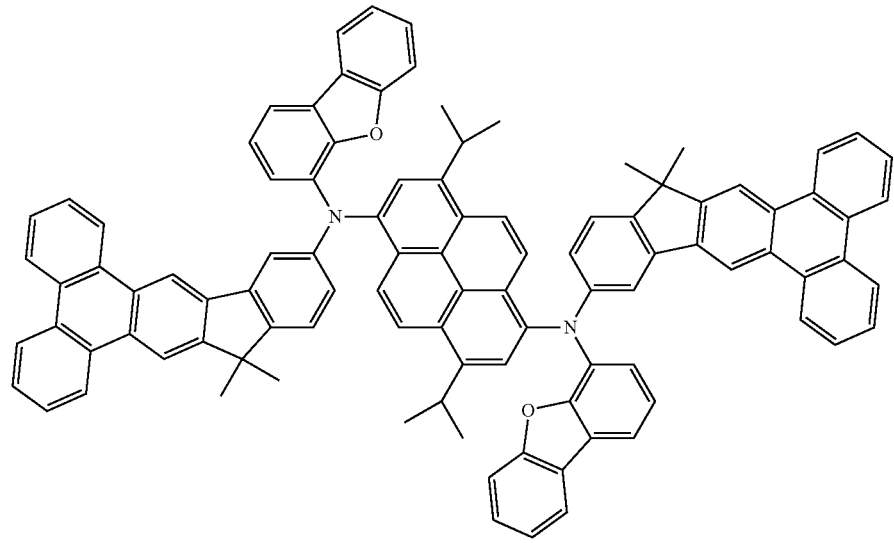
EX42
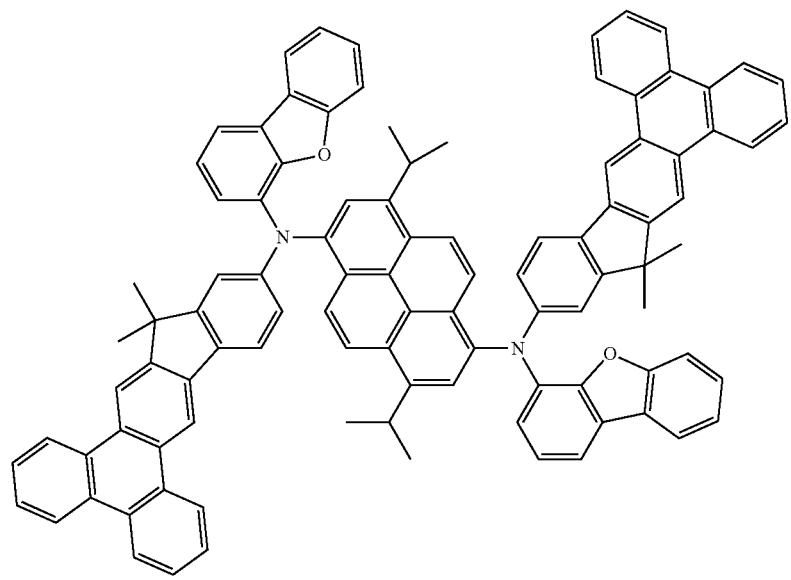
EX43

Detailed preparation for the organic material in the present invention could be clarified by exemplary embodiments, but the present invention is not limited to exemplary embodiments. EXAMPLE 1~8 show the preparation for examples of the organic material in the present invention. EXAMPLE 9 shows the fabrication of organic EL device and I-V-B, half-life time of organic EL device testing report.

Example 1

Synthesis of EX1

Synthesis of N$^1$,N$^5$-bis(10,10-dimethyl-10H-indeno[1,2-b]triphenylen-12-yl)-N$^1$,N$^5$-bis(4-isopropylphenyl)naphthalene-1,5-diamine

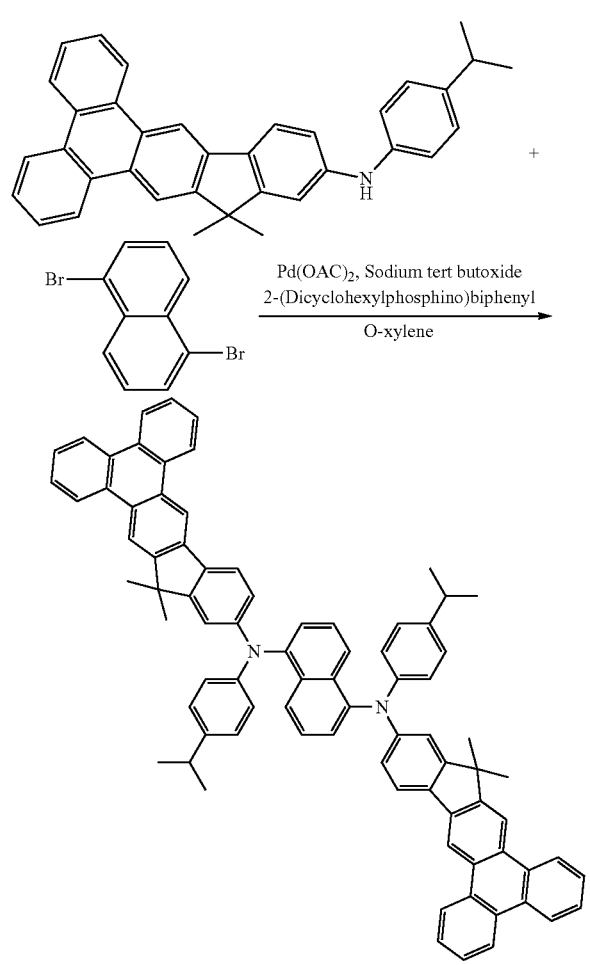

A mixture of 2.8 g (10 mmol) 1,5-dibromonaphthalene, 9.7 g (20.4 mmol) of N-(4-isopropylphenyl)-10,10-dimethyl-10H-indeno[1,2-b]triphenylen-12-amine, 0.05 g (0.2 mmol) of palladium(II)acetate, 0.15 g (0.4 mmol) of 2-(dicyclohexylphosphino)biphenyl, 3.8 g (40 mmol) of sodium tert-butoxide and 50 ml of o-xylene was refluxed under nitrogen overnight. After finishing the reaction, the solution was filtered at 120° C. to receive the filtrate, and the filtrate was added to 1 L MeOH, while stirring and the precipitated product was filtered off with suction. To give 4.0 g (yield 37%) of yellow product which was purified by column chromatography on silica (hexane-dichloromethane). MS (m/z, FAB$^+$): 1078.1.

Example 2

Synthesis of EX3

Synthesis of N-(biphenyl-4-yl)-10,10-dimethyl-10H-indeno[1,2-b]triphenylen-12-amine

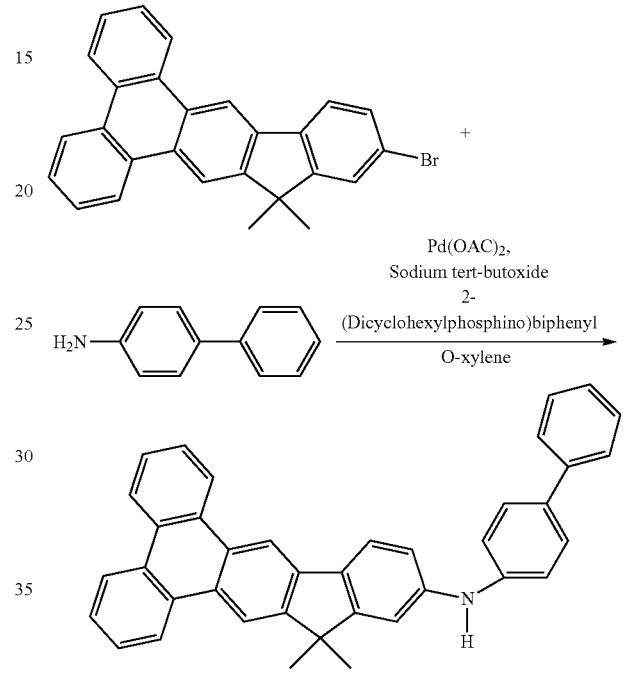

A mixture of 21.1 g (50 mmol) 12-bromo-10,10-dimethyl-10H-indeno[1,2-b]triphenylene, 9.3 g (55 mmol) of biphenyl-4-amine, 0.25 g (1 mmol) of palladium(II)acetate, 0.75 g (2.0 mmol) of 2-(dicyclohexylphosphino)biphenyl, 9.6 g (100 mmol) of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give 8.2 g (yield 32%) of yellow product which was recrystallized from hexane.

Synthesis of N$^9$,N$^{10}$-di(biphenyl-4-yl)-N$^9$,N$^{10}$-bis(10,10-dimethyl-10H-indeno[2,1-b]triphenylen-12-yl)anthracene-9,10-diamine

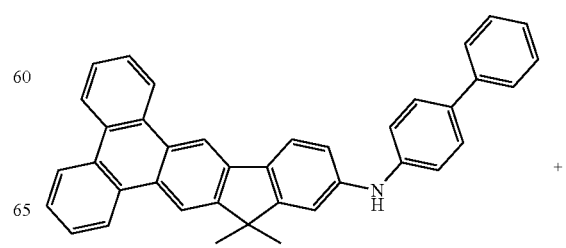

-continued

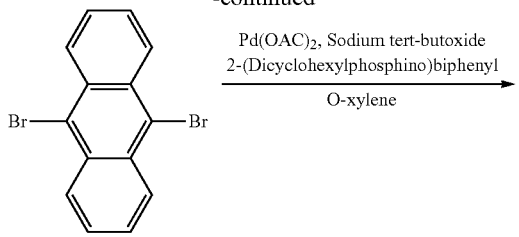

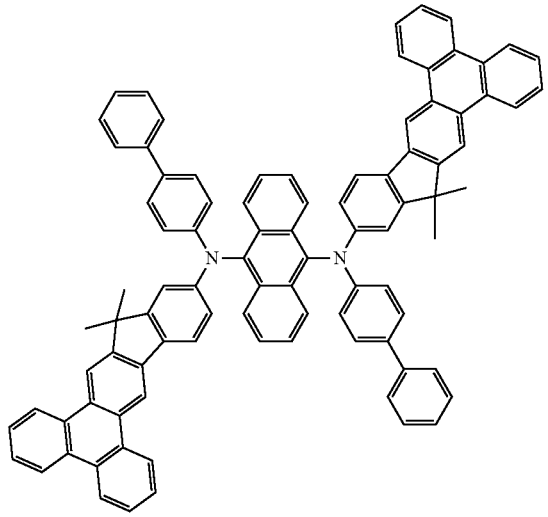

A mixture of 2.3 g (7 mmol) 9,10-dibromoanthracene, 8.9 g (16 mmol) of N-(biphenyl-4-yl)-10,10-dimethyl-10H-indeno[1,2-b]triphenylen-12-amine, 0.05 g (0.2 mmol) of palladium(II)acetate, 0.15 g (0.4 mmol) of 2-(dicyclohexylphosphino)biphenyl, 3.8 g (40 mmol) of sodium tert-butoxide and 50 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 4.4 g (yield 53%) of yellow product which was purified by column chromatography on silica (hexane-dichloromethane). MS (m/z, FAB$^+$): 1197.2.

Example 3

Synthesis of EX7

Synthesis of 10,10-dimethyl-N-phenyl-10H-indeno[1,2-b]triphenylen-12-amine

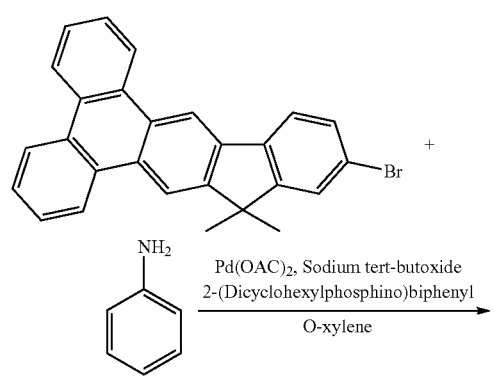

-continued

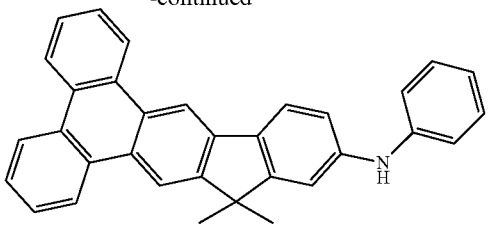

A mixture of 21.1 g (50 mmol) 12-bromo-10,10-dimethyl-10H-indeno[1,2-b]triphenylene, 5.1 g (55 mmol) of aniline, 0.25 g (1 mmol) of palladium(II)acetate, 0.75 g (2.0 mmol) of 2-(dicyclohexylphosphino)biphenyl, 9.6 g (100 mmol) of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give 8.9 g (yield 41%) of yellow product which was recrystallized from hexane.

Synthesis of $N^9,N^{10}$-bis(10,10-dimethyl-10H-indeno[2,1-b]triphenylen-12-yl)-$N^9,N^{10}$-diphenylanthracene-9,10-diamine

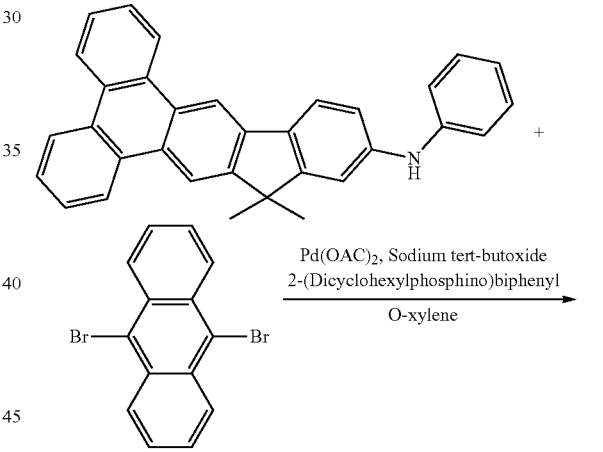

A mixture of 3.3 g (10 mmol) 9,10-dibromoanthracene, 8.9 g (20.4 mmol) of 10,10-dimethyl-N-phenyl-10H-indeno[1,2-b]triphenylen-12-amine, 0.05 g (0.2 mmol) of palladium(II)acetate, 0.15 g (0.4 mmol) of 2-(dicyclohexylphosphino)biphenyl, 3.8 g (40 mmol) of sodium tert-butoxide and 50 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 6.4 g (yield 61%) of yellow product which was purified by column chromatography on silica (hexane-dichloromethane). MS (m/z, FAB+): 1044.6.

Example 4

Synthesis of EX12

Synthesis of 3-(biphenyl-2-yl)-7-bromodibenzo[b,d]furan

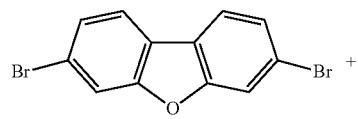

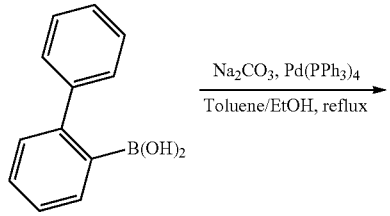

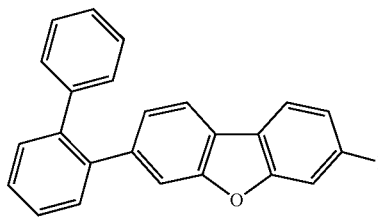

A mixture of 16.3 g (50 mmol) of 3,7-dibromodibenzo[b,d]furan, 10 g (50 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 110° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (9 g, 22.5 mmol, 45%) as a white solid.

Synthesis of 12-bromobenzo[d]triphenyleno[2,3-b]furan

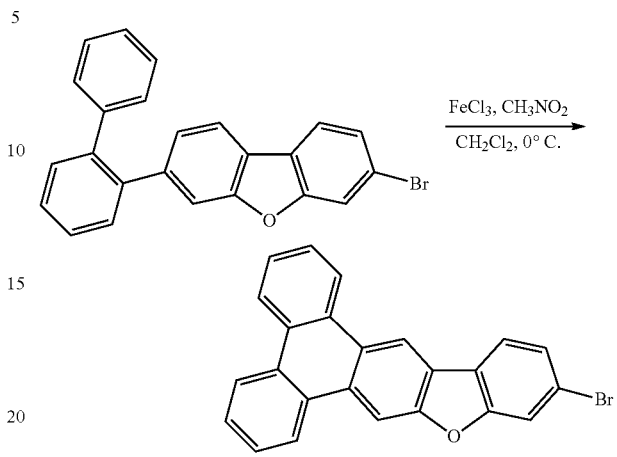

In a 3000 ml three-necked flask that had been degassed and filled with nitrogen, 9 g (22.5 mmol) of 3-(biphenyl-2-yl)-7-bromodibenzo[b,d]furan was dissolved in anhydrous dichloromethane (900 ml), 18.3 g (112.5 mmol) Iron(III) chloride was then added, and the mixture was stirred 20 minutes. Methanol 300 ml was added to the mixture and the organic layer was separated and the solvent removed in vacuo. The residue was purified by column chromatography on silica(hexane-dichloromethane) afforded a white solid (7.4 g, 18.7 mmol, 83%).

Synthesis of N-(4-isopropylphenyl)benzo[d]triphenyleno[2,3-b]furan-12-amine

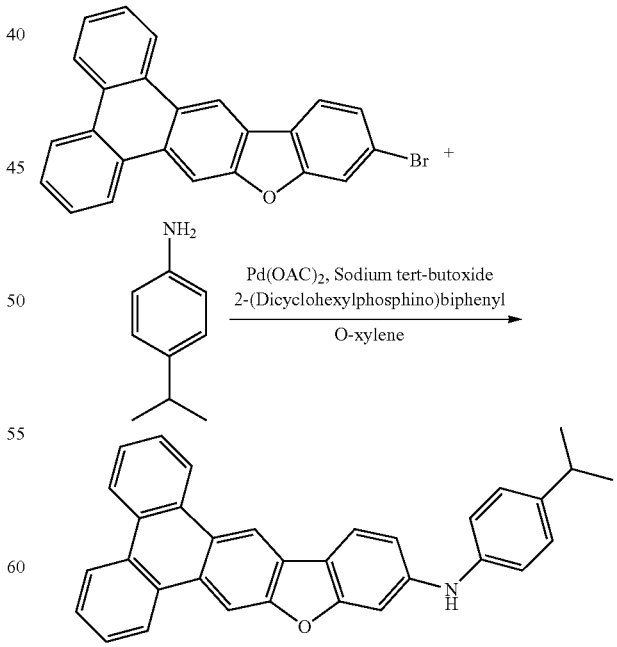

A mixture of 7.4 g (18.7 mmol) 12-bromobenzo[d]triphenyleno[2,3-b]furan, 3.7 g (27.5 mmol) of 4-isopropylaniline, 0.25 g (1 mmol) of palladium(II)acetate, 0.75 g (2.0 mmol) of 2-(dicyclohexylphosphino)biphenyl, 4.8 g (50 mmol) of sodium tert-butoxide and 50 ml of o-xylene was refluxed under nitrogen overnight. After finishing the reaction, the solution was filtered at 100° C., to receive the filtrate, and the filtrate was added to 500 ml MeOH, while stirring and the precipitated product was filtered off with suction. To give 4.3 g (yield 51%) of yellow product which was recrystallized from hexane.

Synthesis of $N^9,N^{10}$-bis(benzo[b]triphenyleno[2,3-d]furan-12-yl)-$N^9,N^{10}$-bis(4-isopropylphenyl)anthracene-9,10-diamine

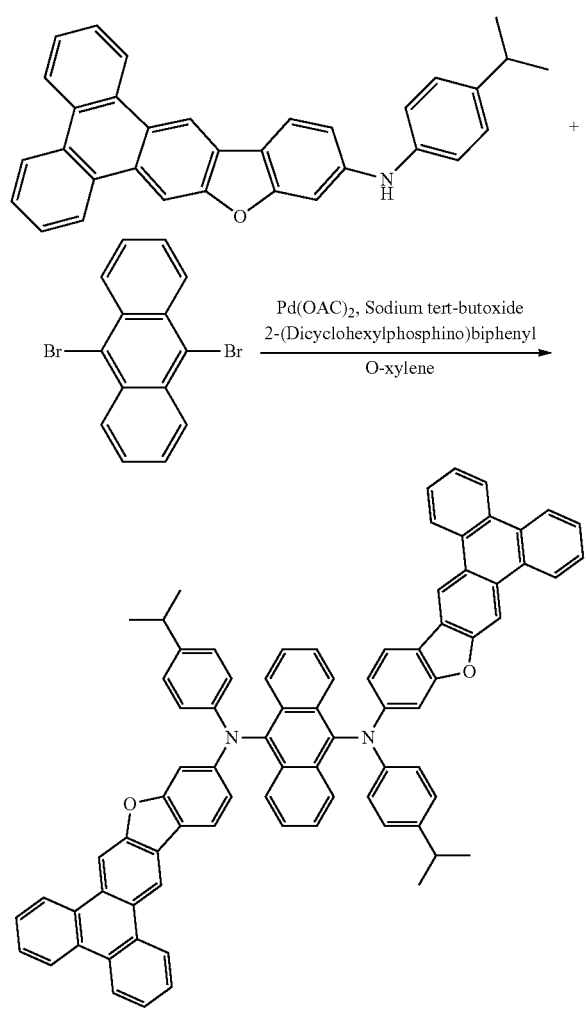

A mixture of 1.5 g (4.3 mmol) 9,10-dibromoanthracene, 4.3 g (9.5 mmol) of N-(4-isopropylphenyl)benzo[d]triphenyleno[2,3-b]furan-12-amine, 0.025 g (0.1 mmol) of palladium(II)acetate, 0.08 g (0.2 mmol) of 2-(dicyclohexylphosphino)biphenyl, 1.9 g (20 mmol) of sodium tert-butoxide and 30 ml of o-xylene was refluxed under nitrogen overnight. After finishing the reaction, the solution was filtered at 120° C., to receive the filtrate, and the filtrate was added to 500 ml MeOH, while stirring and the precipitated product was filtered off with suction. To give 1.8 g (yield 39%) of yellow product which was purified by column chromatography on silica(hexane-dichloromethane). MS (m/z, FAB$^+$): 1076.6.

Example 5

Synthesis of EX17

Synthesis of 10,10-dimethyl-N-m-tolyl-10H-indeno[1,2-b]triphenylen-13-amine

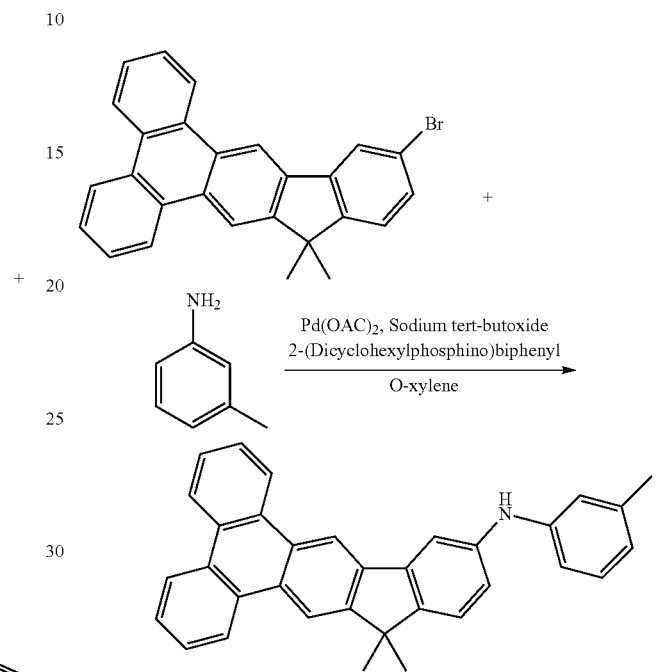

A mixture of 21.1 g (50 mmol) 13-bromo-10,10-dimethyl-10H-indeno[1,2-b]triphenylene, 5.9 g (55 mmol) of m-toluidine, 0.25 g (1 mmol) of palladium(II)acetate, 0.75 g (2.0 mmol) of 2-(dicyclohexylphosphino)biphenyl, 9.6 g (100 mmol) of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give 8.9 g (yield 41%) of yellow product which was recrystallized from hexane.

Synthesis of $N^1,N^6$-bis(10,10-dimethyl-10H-indeno[2,1-b]triphenylen-13-yl)-$N^1,N^6$-dim-tolylpyrene-1,6-diamine

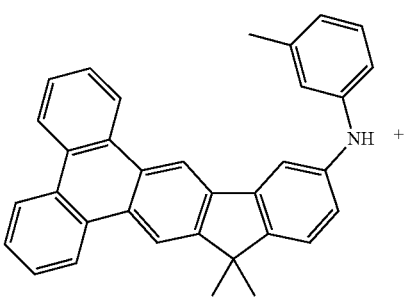

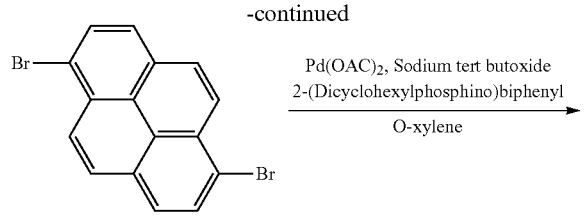

Example 6

Synthesis of EX21

Synthesis of N-(4-isopropylphenyl)-10,10-dimethyl-10H-indeno[1,2-b]triphenylen-12-amine

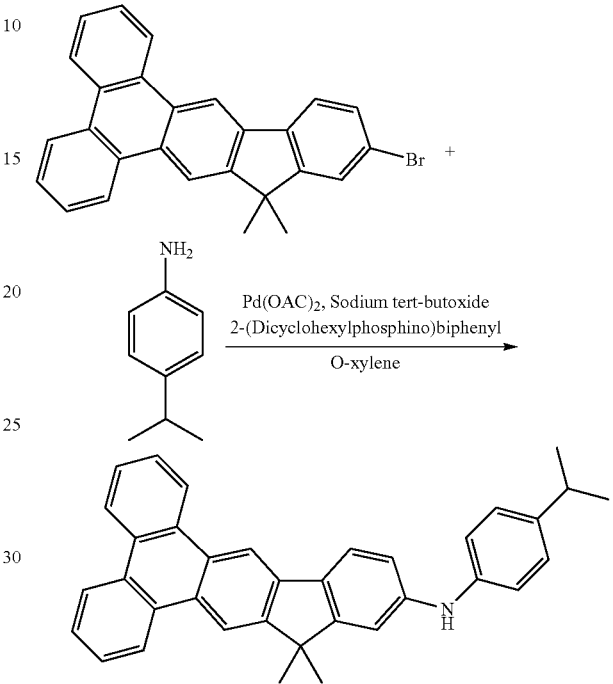

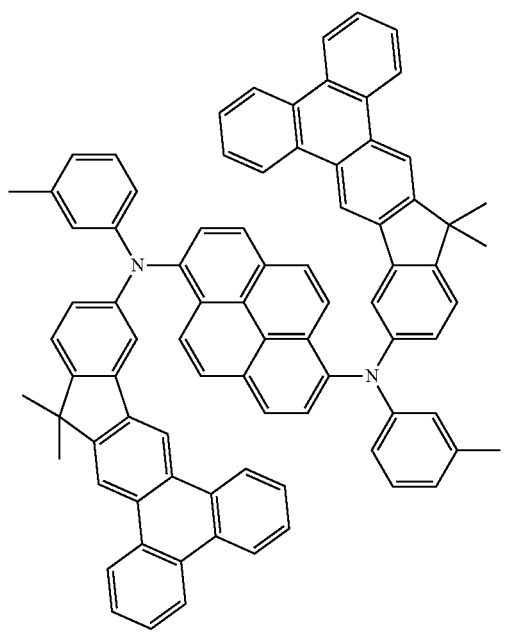

A mixture of 3.6 g (10 mmol) 1,6-dibromopyrene, 9.2 g (20.5 mmol) of 10,10-dimethyl-N-m-tolyl-10H-indeno[1,2-b]triphenylen-13-amine, 0.05 g (0.2 mmol) of palladium(II) acetate, 0.15 g (0.4 mmol) of 2-(dicyclohexyl phosphino)biphenyl, 3.8 g (40 mmol) of sodium tert-butoxide and 50 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 4.3 g (yield 39%) of yellow product which was purified by column chromatography on silica (hexane-dichloromethane). MS (m/z, FAB⁺): 1096.6.

A mixture of 21.1 g (50 mmol) 12-bromo-10,10-dimethyl-10H-indeno[1,2-b]triphenylene, 7.4 g (55 mmol) of 4-isopropylaniline, 0.25 g (1 mmol) of palladium(II)acetate, 0.75 g (2.0 mmol) of 2-(dicyclohexylphosphino)biphenyl, 9.6 g (100 mmol) of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give 11 g (yield 46%) of yellow product which was recrystallized from hexane.

Synthesis of N¹,N⁶-bis(10,10-dimethyl-10H-indeno[1,2-b]triphenylen-12-yl)-N¹,N⁶-bis(4-isopropylphenyl)pyrene-1,6-diamine

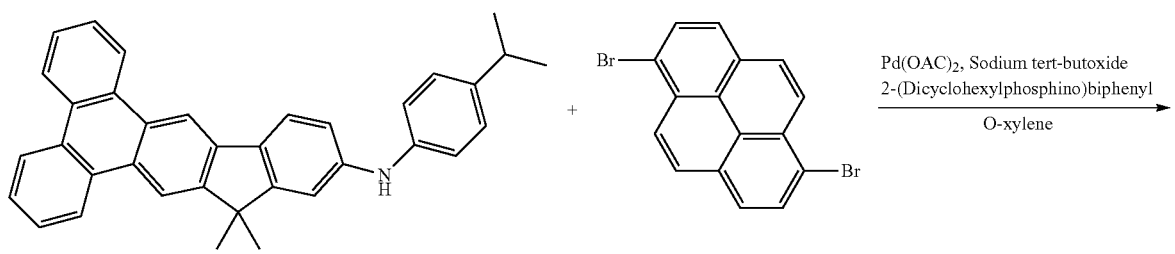

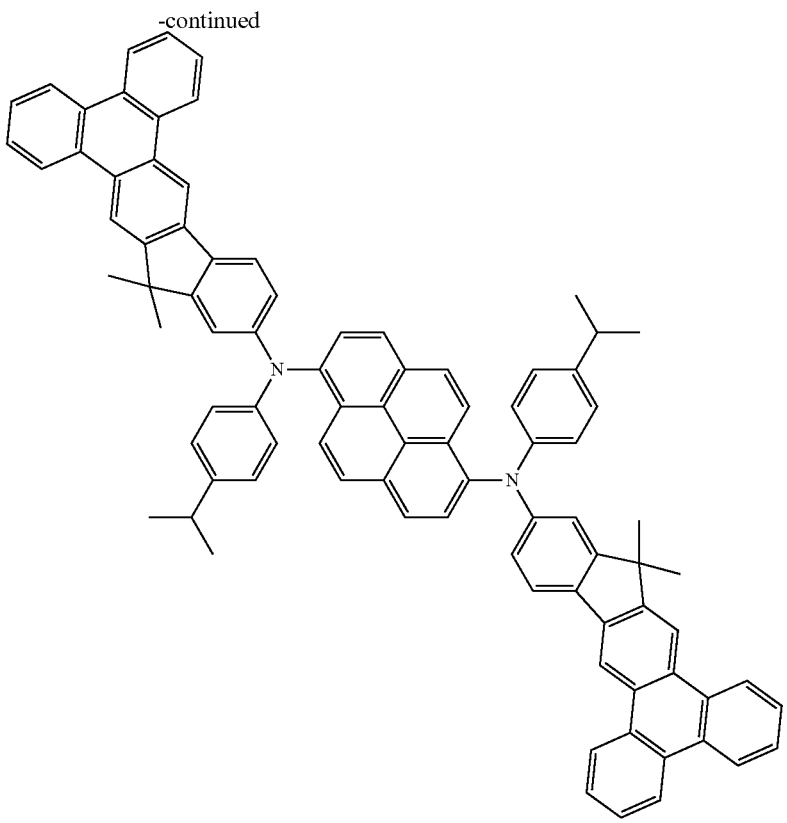

A mixture of 3.6 g (10 mmol) 1,6-dibromopyrene, 9.7 g (20.4 mmol) of N-(4-isopropylphenyl)-10,10-dimethyl-10H-indeno[1,2-b]triphenylen-12-amine, 0.05 g (0.2 mmol) of palladium(II)acetate, 0.15 g (0.4 mmol) of 2-(dicyclohexylphosphino)biphenyl, 3.8 g (40 mmol) of sodium tert-butoxide and 50 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 3.7 g (yield 32%) of yellow product which was purified by column chromatography on silica(hexane-dichloromethane). MS (m/z, FAB$^+$): 1152.2.

Example 7

Synthesis of EX26

Synthesis of 3-(biphenyl-2-yl)-6-bromo-9-ethyl-9H-carbazole

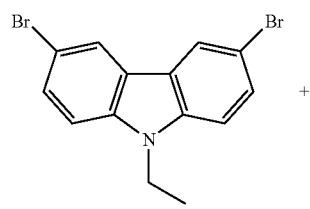

+

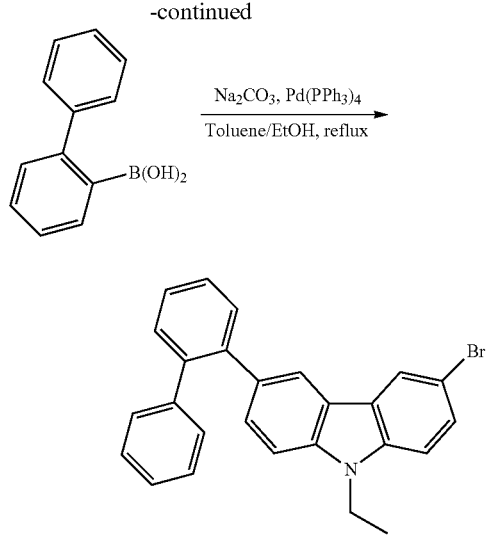

A mixture of 17.6 g (50 mmol) of 3,6-dibromo-9-ethyl-9H-carbazole, 10 g (50 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 110° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (10.2 g, 24 mmol, 48%) as a white solid.

Synthesis of 13-bromo-10-ethyl-10H-phenanthro[9,10-b]carbazole

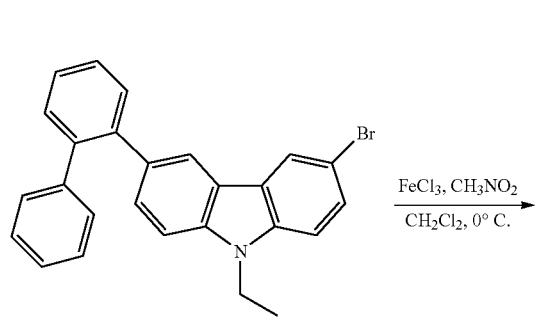

In a 3000 ml three-necked flask that had been degassed and filled with nitrogen, 10.2 g (24 mmol) of 3-(biphenyl-2-yl)-6-bromo-9-ethyl-9H-carbazole was dissolved in anhydrous dichloromethane (1020 ml), 19.5 g (120 mmol) Iron (III) chloride was then added, and the mixture was stirred 20 minutes. Methanol 500 ml was added to the mixture and the organic layer was separated and the solvent removed in vacuo. The residue was purified by column chromatography on silica(hexane-dichloromethane) afforded a white solid (6.8 g, 16 mmol, 67%).

Synthesis of N-(3,5-dimethylphenyl)-10-ethyl-10H-phenanthro[9,10-b]carbazol-13-amine

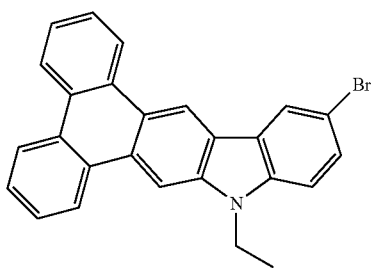

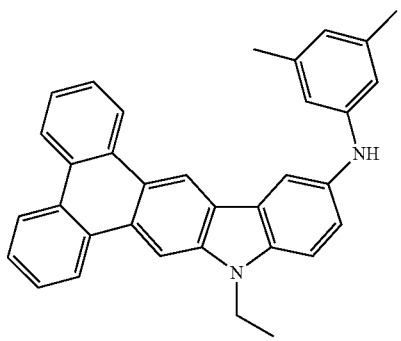

A mixture of 6.8 g (16 mmol) 13-bromo-10-ethyl-10H-phenanthro[9,10-b]carbazole, 1.9 g (16 mmol) of 3,5-dimethylaniline, 0.13 g (0.5 mmol) of palladium(II)acetate, 0.38 g (1.0 mmol) of 2-(dicyclohexylphosphino)biphenyl, 4.8 g (50 mmol) of sodium tert-butoxide and 50 ml of o-xylene was refluxed under nitrogen overnight. After finishing the reaction, the solution was filtered at 110° C., to receive the filtrate, and the filtrate was added to 500 ml MeOH, while stirring and the precipitated product was filtered off with suction. To give 3.8 g (yield 51%) of yellow product which was recrystallized from hexane and dichloromethane.

Synthesis of $N^1,N^6$-bis(3,5-dimethylphenyl)-$N^1,N^6$-bis(10-ethyl-10H-phenanthro[9,10-b]carbazol-13-yl)pyrene-1,6-diamine

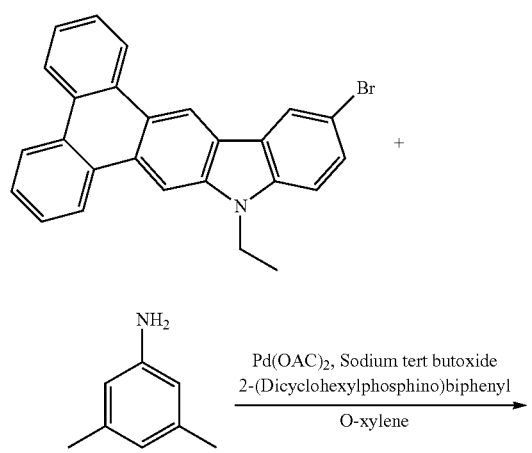

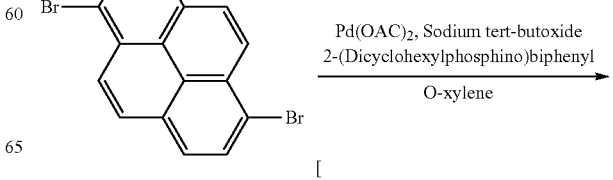

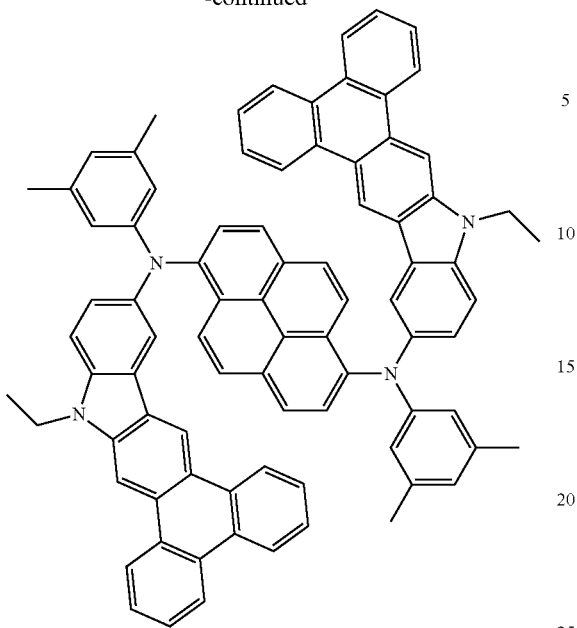

A mixture of 1.3 g (3.7 mmol) 1,6-dibromopyrene, 3.8 g (8.2 mmol) of N-(3,5-dimethylphenyl)-10-ethyl-10H-phenanthro[9,10-b]carbazol-13-amine, 0.025 g (0.1 mmol) of palladium(II)acetate, 0.08 g (0.2 mmol) of 2-(dicyclohexylphosphino)biphenyl, 1.9 g (20 mmol) of sodium tert-butoxide and 20 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 1.9 g (yield 46%) of yellow product which was purified by column chromatography on silica(hexane-dichloromethane). MS (m/z, FAB$^+$): 1126.7.

Example 8

Synthesis of EX29

Synthesis of 6-bromo-2-iododibenzo[b,d]furan

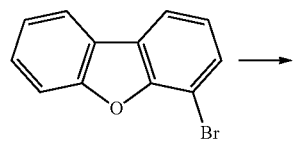

A mixture of 24.7 g (100 mmol) 4-bromodibenzo[b,d]furan, 12.7 g (50 mmol) of iodine, 16.1 g (50 mmol) of phenyliododiacetate, 50 ml of acetic acid, 50 ml of acetic anhydride and 3 ml of sulfuric acid were stirred at room temperature for 24 hours. After completion of reaction, toluene was added to the reaction mixture and the mixture was washed with water. After the organic phase was dried with anhydrous magnesium sulfate, the solvent in the organic phase was distilled away under reduced pressure. The residue was purified by column chromatography on silica(hexane-dichloromethane) afforded a white solid (19 g, 51 mmol, 51%)

Synthesis of 2-(biphenyl-2-yl)-6-bromodibenzo[b,d]furan

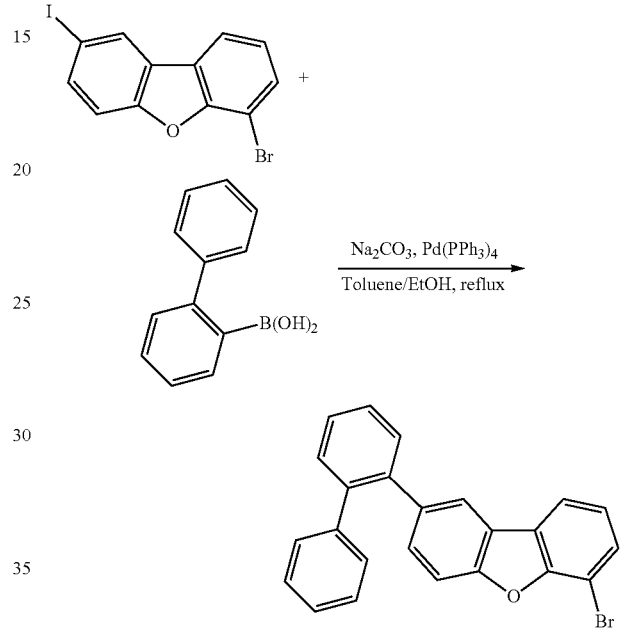

A mixture of 19 g (51 mmol) of 6-bromo-2-iododibenzo[b,d]furan, 11 g (55 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 110° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (12.8 g, 32.1 mmol, 63%) as a white solid.

Synthesis of 11-bromobenzo[d]triphenyleno[2,3-b]furan

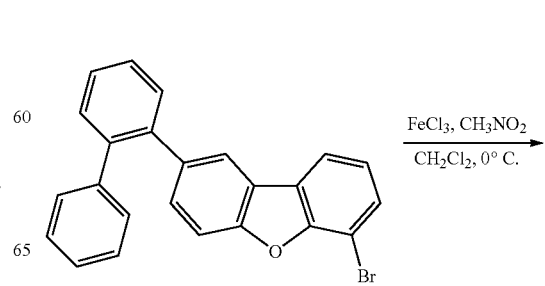

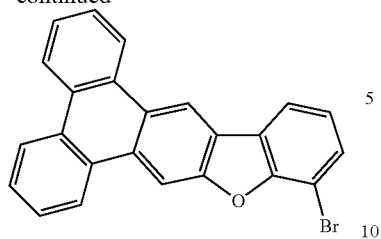

In a 3000 ml three-necked flask that had been degassed and filled with nitrogen, 12.8 g (32.1 mmol) of 2-(biphenyl-2-yl)-6-bromodibenzo[b,d]furan was dissolved in anhydrous dichloromethane (1280 ml), 26.1 g (160.5 mmol) Iron(III) chloride was then added, and the mixture was stirred 20 minutes. Methanol 400 ml was added to the mixture and the organic layer was separated and the solvent removed in vacuo. The residue was purified by column chromatography on silica(hexane-dichloromethane) afforded a white solid (9.9 g, 25 mmol, 78%).

Synthesis of N-(biphenyl-4-yl)benzo[d]triphenyleno[2,3-b]furan-11-amine

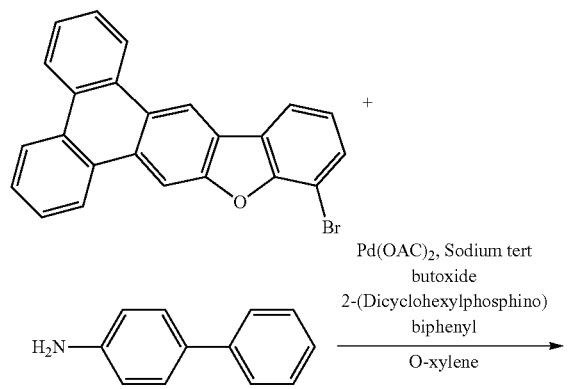

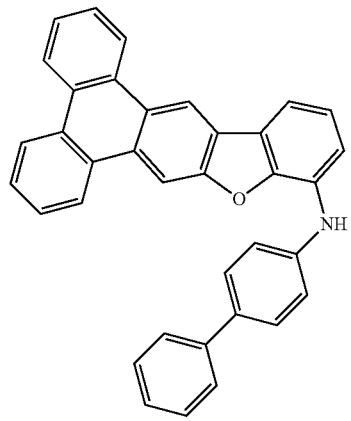

A mixture of 9.9 g (25 mmol) 11-bromobenzo[d]triphenyleno[2,3-b]furan, 4.3 g (25 mmol) of biphenyl-4-amine, 0.25 g (1 mmol) of palladium(II)acetate, 0.75 g (2.0 mmol) of 2-(dicyclohexylphosphino)biphenyl, 9.6 g (100 mmol) of sodium tert-butoxide and 50 ml of o-xylene was refluxed under nitrogen overnight. After finishing the reaction, the solution was filtered at 100° C., to receive the filtrate, and the filtrate was added to 500 ml MeOH, while stirring and the precipitated product was filtered off with suction. To give 5.8 g (yield 48%) of yellow product which was recrystallized from hexane.

Synthesis of $N^1,N^6$-bis(benzo[b]triphenyleno[2,3-d]furan-11-yl)-$N^1,N^6$-di(biphenyl-4-yl)pyrene-1,6-diamine

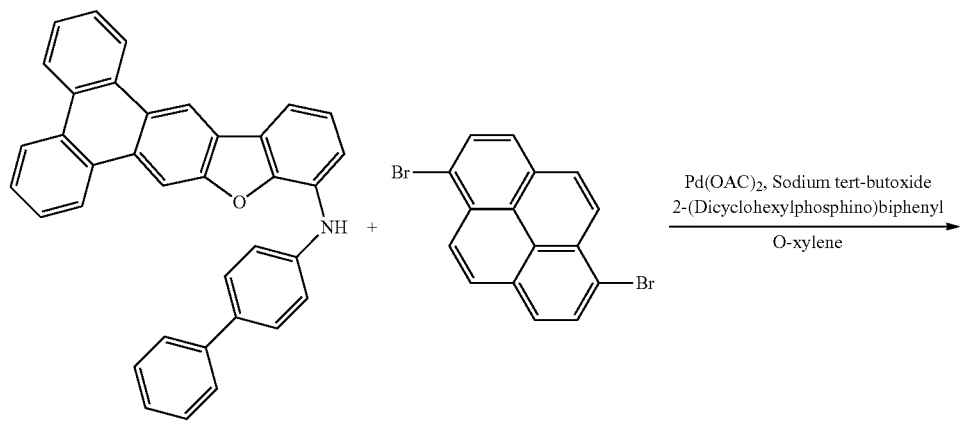

-continued

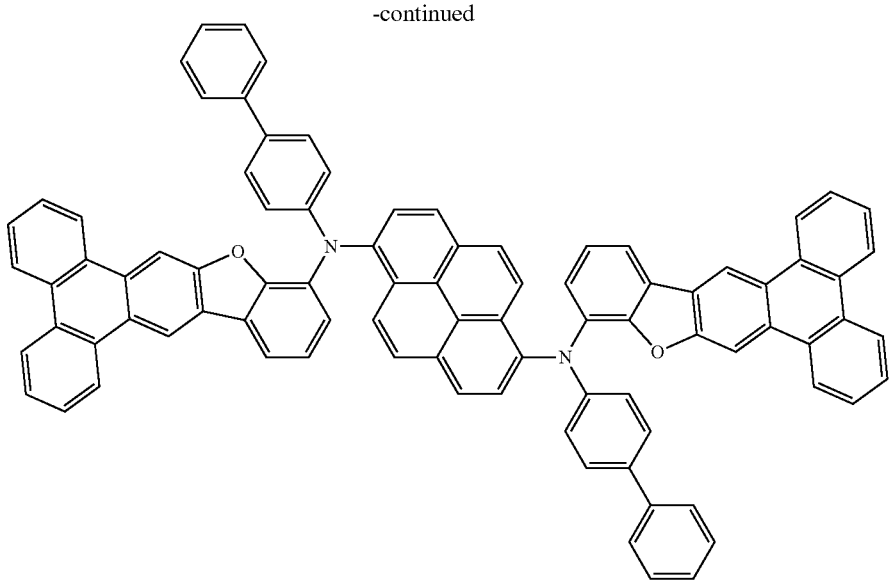

A mixture of 1.3 g (3.7 mmol) 1,6-dibromopyrene, 4.0 g (8.2 mmol) of N-(biphenyl-4-yl)benzo[d]triphenyleno[2,3-b]furan-11-amine, 0.025 g (0.1 mmol) of palladium(II) acetate, 0.08 g (0.2 mmol) of 2-(dicyclohexyl phosphino) biphenyl, 1.9 g (20 mmol) of sodium tert-butoxide and 20 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 1.6 g (yield 38%) of yellow product which was purified by column chromatography on silica (hexane-dichloromethane). MS (m/z, FAB$^+$): 1168.1.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f: 2,3-]quinoxaline-2,3,6,7,10,11-hexacarbonitrile (HAT-CN) is used as hole injection layer in this organic EL device, N,N-Bis(naphthalene-1-yl)-N,N-bis (phenyl)-benzidine (NPB) is most widely used as the hole transporting layer; 10,10-dimethyl-13-(3-(pyren-1-yl)phenyl)-10H-indeno[2,1-b]triphenylene (H1), 10,10-dimethyl-12-(4-(pyren-1-yl)phenyl)-10H-indeno[2,1-b]triphenylene (H2), 10,10-dimethyl-12-(10-(4-(naphthalene-1-yl)phenyl)anthracen-9-yl)-10H-indeno[2,1-b]triphenylene(H3) and 10,10-dimethyl-13-(10-(3-(naphthalen-2-yl)phenyl)anthracen-9-yl)-10H-indeno[2,1-b]triphenylene (H4) are used as emitting host in organic EL device and N1,N1,N6,N6-tetram-tolylpyrene-1,6-diamine (D1) is used as blue guest for comparison; HB3 (see the following chemical structure) are used as hole blocking material (HBM) and 2-(naphthalen-1-yl)-9-(4-(1-(4-(10-(naphthalene-2-yl)anthracen-9-yl)phenyl)-1H-benzo[d]imidazol-2-yl)phenyl)-1,10-phenanthroline (ET2) is used as electron transporting material to co-deposit with 8-hydroxyquinolato-lithium (LiQ) in organic EL device. The prior art of OLED materials for producing standard organic EL device control and comparable material in this invention shown its chemical structure as follows:

HAT-CN NPB

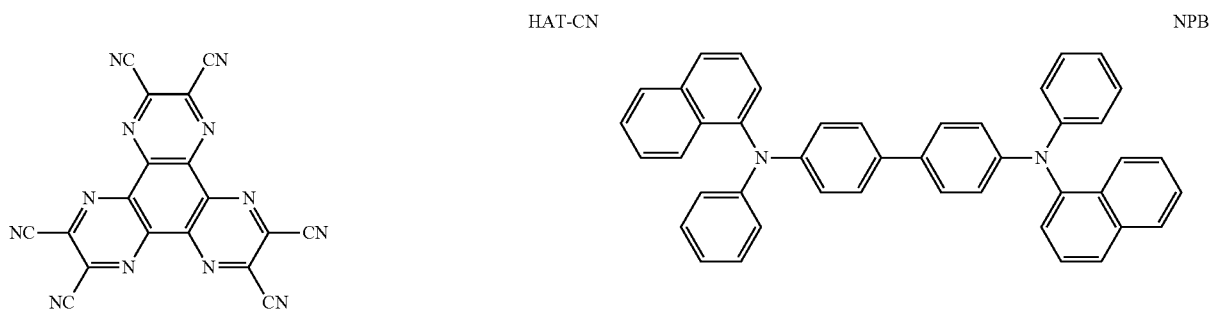

-continued
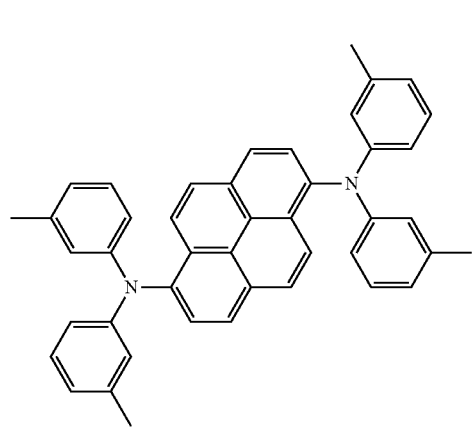 D1
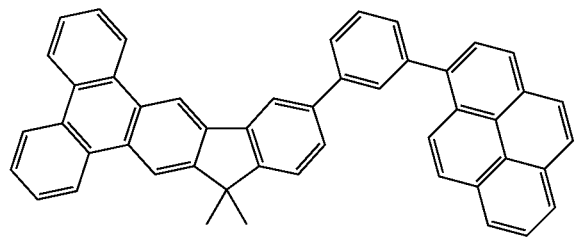 H1
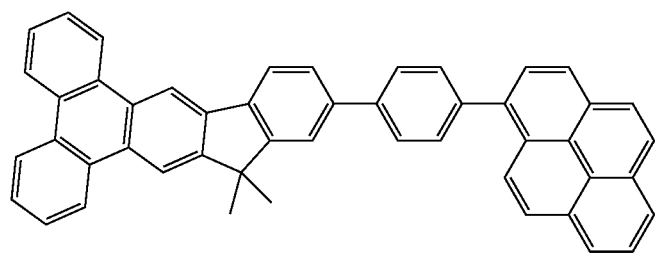 H2
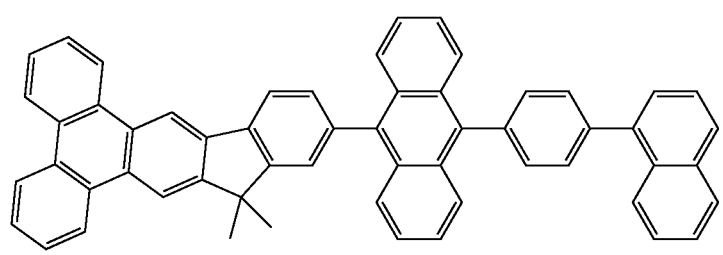 H3
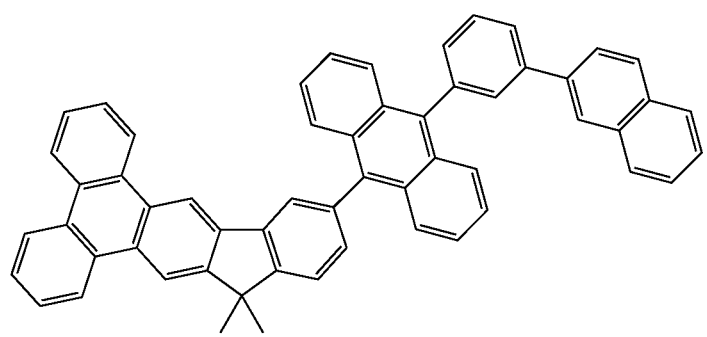 H4

HB3
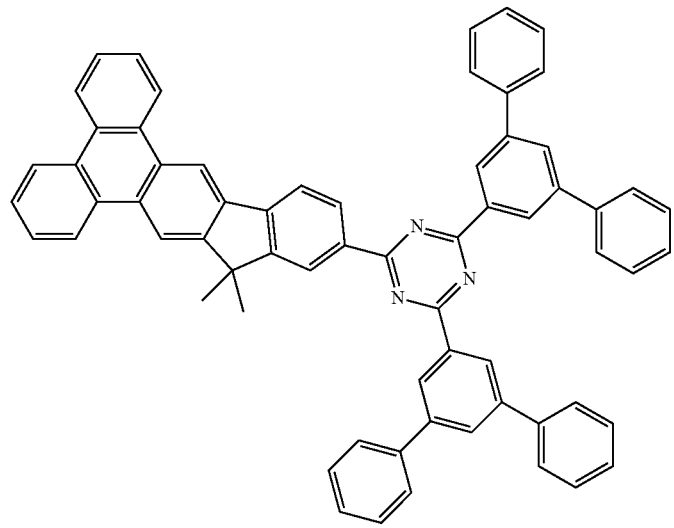
LiQ
ET2
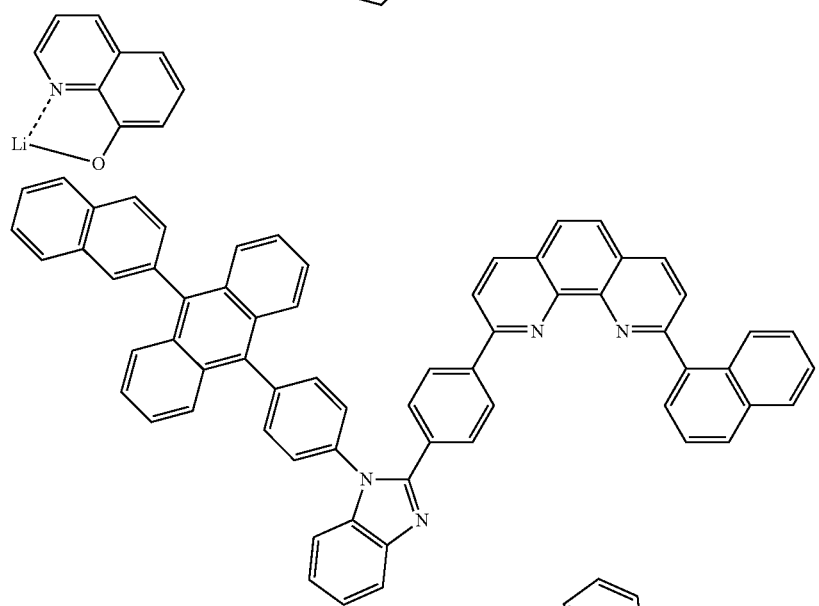
EX1
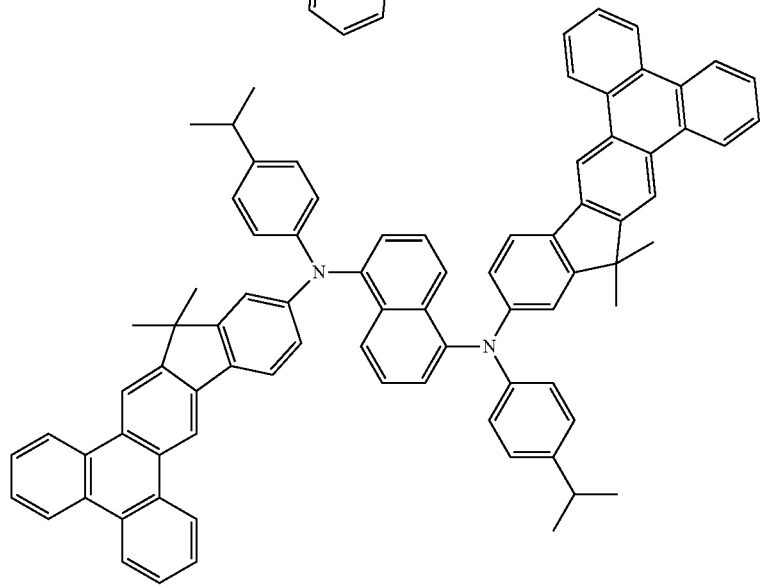

-continued
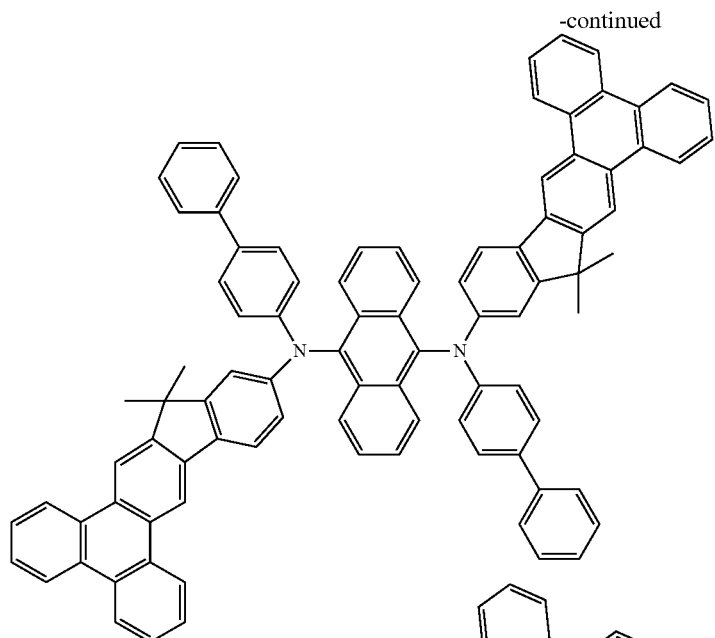
EX3
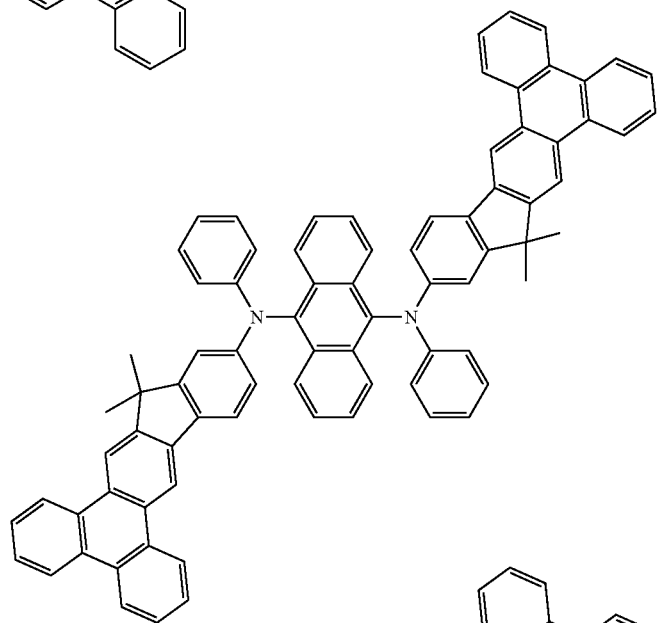
EX7
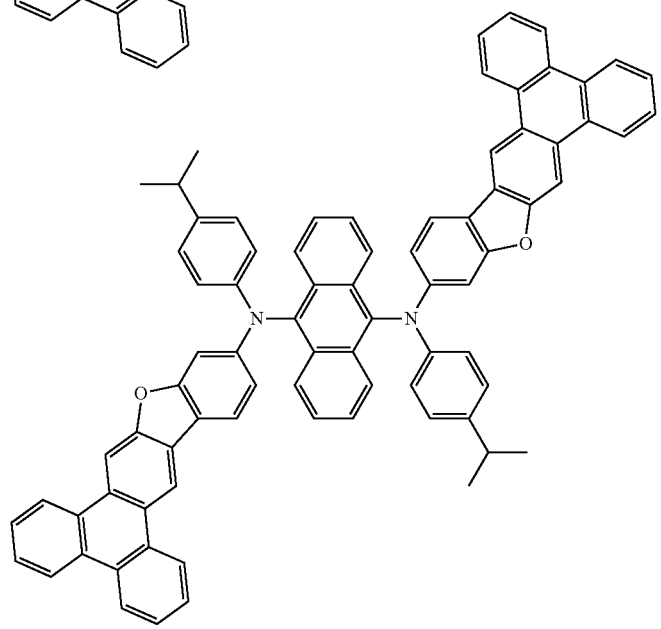
EX12

EX17
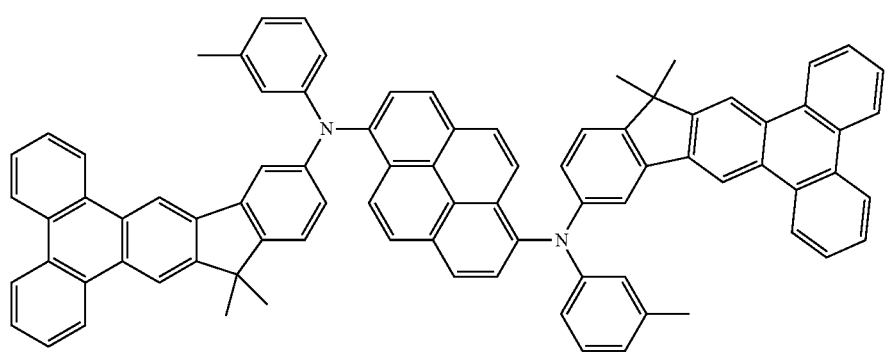
EX21
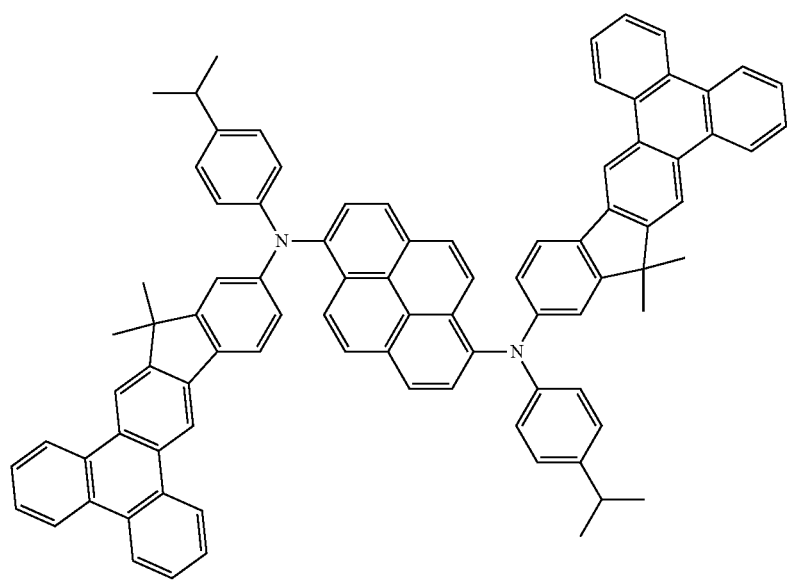
EX26
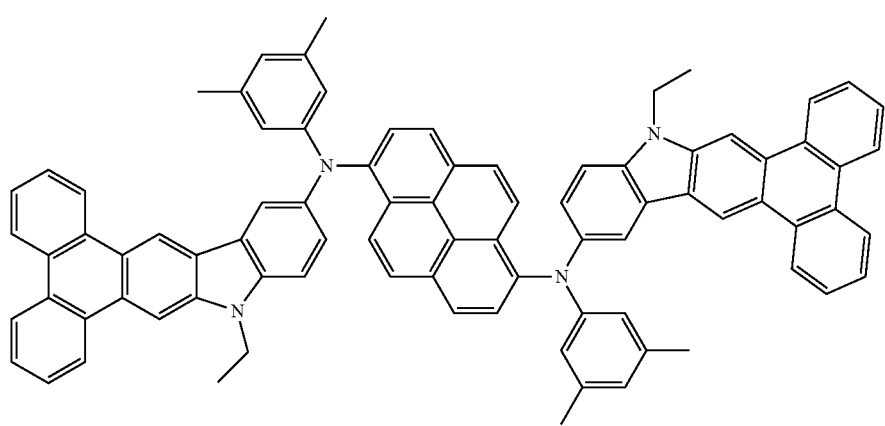

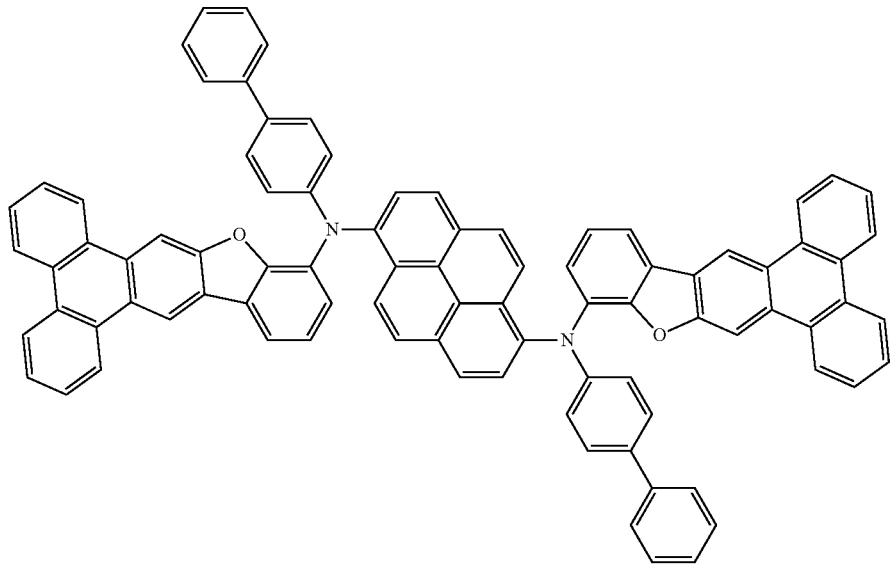

EX29

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 9

Using a procedure analogous to the above mentioned general method, fluorescent emitting organic EL device having the following device structure was produced (See FIG. 1). Device: ITO/HAT-CN (20 nm)/NPB (110 nm)/ Emitting host doped 5% Emitting guest (30 nm)/HB3/ET2 doped 50% LiQ (35 nm)/LiQ (1 nm)/Al (160 nm). The I-V-B (at 1000 nits) and half-life time of fluorescent emitting organic EL device testing report as Table 1. The half-life time is defined that the initial luminance of 1000 cd/m² has dropped to half.

TABLE 1

| Emitting Host | Emitting Guest | Voltage (V) | Efficiency (cd/A) | Device Colour | Half-life time (hour) |
|---|---|---|---|---|---|
| H1 | EX1 | 4.2 | 3.0 | blue | 80 |
| H1 | EX3 | 3.5 | 16.8 | green | 850 |

TABLE 1-continued

| Emitting Host | Emitting Guest | Voltage (V) | Efficiency (cd/A) | Device Colour | Half-life time (hour) |
|---|---|---|---|---|---|
| H1 | EX7 | 3.6 | 15.5 | green | 880 |
| H1 | EX12 | 3.5 | 8.5 | green | 900 |
| H1 | EX17 | 3.5 | 5.4 | blue | 250 |
| H1 | EX21 | 3.6 | 5.8 | blue | 220 |
| H1 | EX26 | 4.0 | 4.5 | blue | 150 |
| H1 | EX29 | 3.8 | 4.0 | blue | 110 |
| H1 | D1 | 3.5 | 5.3 | blue | 180 |
| H2 | EX3 | 3.9 | 18.0 | green | 1100 |
| H2 | EX7 | 4.2 | 17.5 | green | 1050 |
| H2 | EX17 | 4.3 | 6.0 | blue | 300 |
| H2 | EX21 | 4.5 | 6.2 | blue | 350 |
| H3 | EX17 | 3.3 | 5.8 | blue | 320 |
| H3 | EX21 | 3.5 | 6.2 | blue | 300 |
| H4 | D1 | 3.5 | 5.5 | blue | 280 |
| H4 | EX17 | 3.2 | 6.3 | blue | 350 |
| H4 | EX21 | 3.4 | 6.5 | blue | 380 |

In the above preferred embodiments for organic EL device test report (see Table 1), we show that the organic material with a general formula (1) used as emitting guest material for organic EL in the present invention display good performance than the prior art of organic EL materials. More specifically, the organic EL device in the present invention use the organic material with a general formula (1) as emitting guest material to collocate with emitting host material such as H1, H2, H3 and H4 shown lower power consumption, higher efficiency and longer half-life time.

To sum up, the present invention discloses an organic material with a general formula (1) used as emitting guest material for organic EL device. The mentioned organic material are represented by the following formula (1)

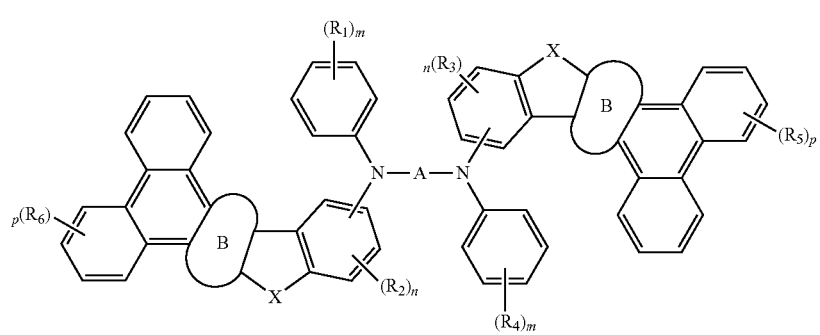

formula (1)

wherein A represents a substituted or unsubstituted fused ring hydrocarbon units with two to five rings, preferably A represents a substituted or unsubstituted naphthyl group, a substituted or unsubstituted phenanthrenyl group, a substituted or unsubstituted anthracenyl group, a substituted or unsubstituted pyrenyl group, a substituted or unsubstituted chrysenyl group, a substituted or unsubstituted triphenylenyl group and a substituted or unsubstituted perylenyl group, B ring represents a benzene ring and which is condensed with the adjacent rings in different manner; X represents a divalent bridge selected from the atom or group consisting from O, S, $C(R_7)(R_8)$ and $N(R_9)$, m represents an integer of 0 to 5, n represents an integer of 0 to 3, p represents an integer of 0 to 8, $R_1$ to $R_9$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A organic material represented by the following formula (1):

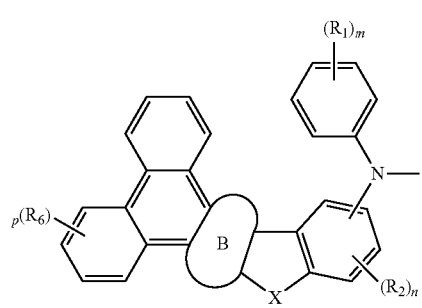

formula (1)

-continued

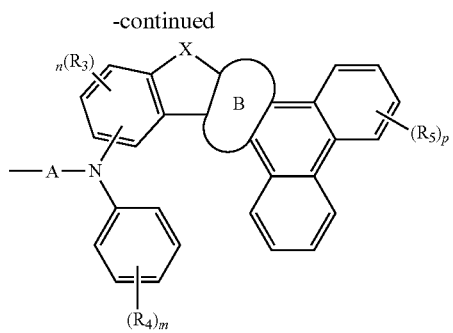

wherein A represents a substituted or unsubstituted fused ring hydrocarbon units with two to five rings, preferably A represents a substituted or unsubstituted naphthyl group, a substituted or unsubstituted phenanthrenyl group, a substituted or unsubstituted anthracenyl group, a substituted or unsubstituted pyrenyl group, a substituted or unsubstituted chrysenyl group, a substituted or unsubstituted triphenylenyl group and a substituted or unsubstituted perylenyl group, B ring represents a benzene ring and which is condensed with the adjacent rings in different manner; X represents a divalent bridge selected from the atom or group consisting from O, S, $C(R_7)(R_8)$ and $N(R_9)$, m represents an integer of 0 to 5, n represents an integer of 0 to 3, p represents an integer of 0 to 8, $R_1$ to $R_9$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

2. The organic material according to claim 1, wherein A is represented by the following formulas:

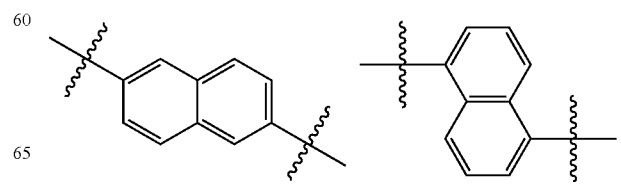

81
-continued

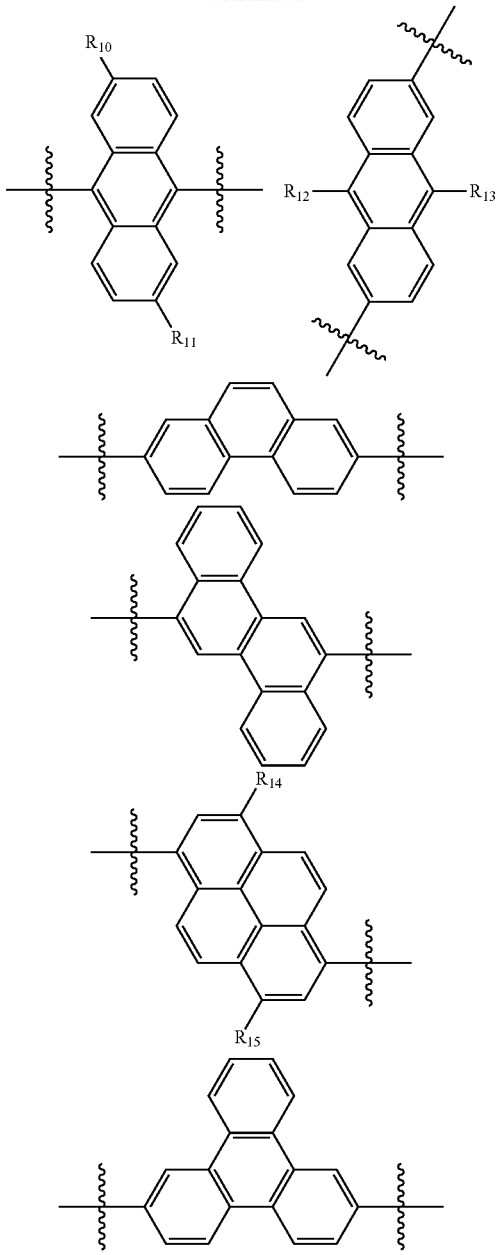

82
-continued

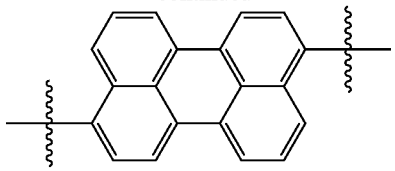

wherein R_{10} to R_{15} are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

3. The organic material according to claim 1, when m represents an integer of 1, preferably $R_1$ and $R_4$ are represented by the following formula (2); when m represents an integer of 2, and $R_1$ or $R_4$ are each independently in adjacent position, preferably $R_1$ and $R_4$ are represented by the following formula (3)

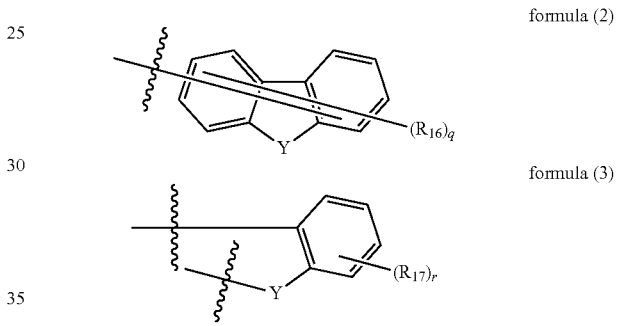

formula (2)

formula (3)

wherein Y represents a divalent bridge selected from the atom or group consisting from O, S and $N(R_{18})$, q represents an integer of 0 to 8, r represents an integer of 0 to 4, $R_{16}$ to $R_{18}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

4. The organic material according to claim 1, wherein the organic material formula (1) is represented by the following formula (4) to formula (6):

formula(4)

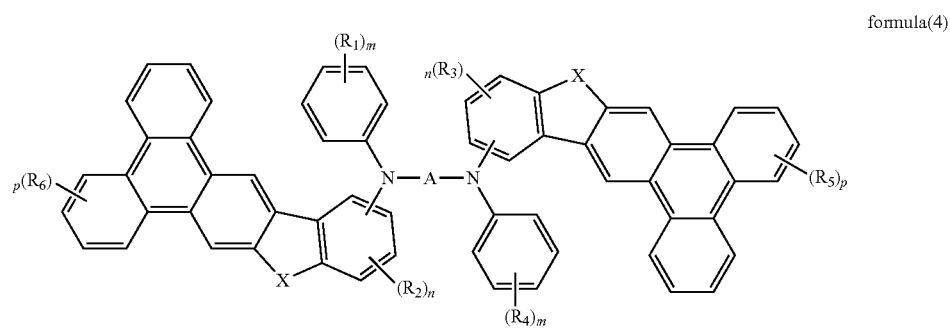

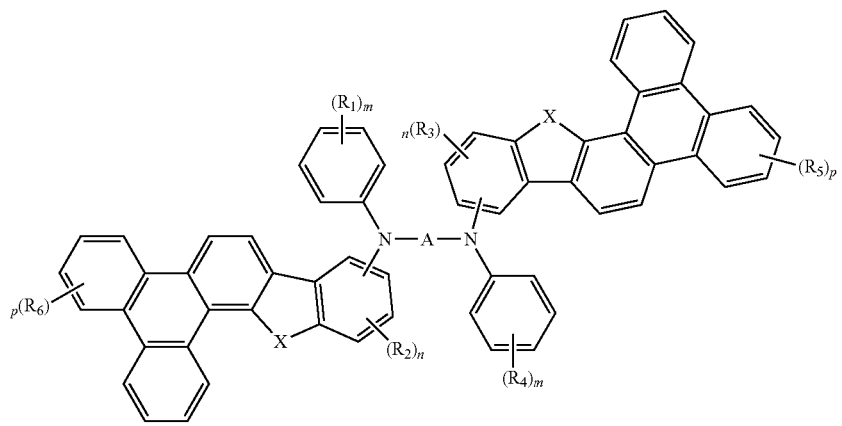

formula(5)

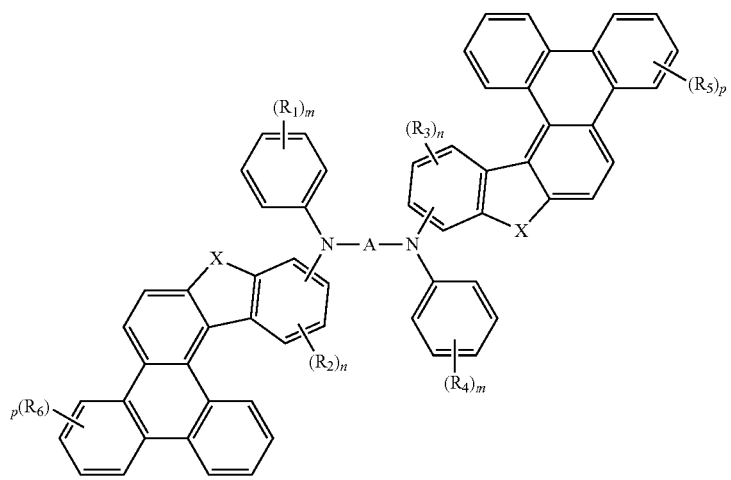

formula(6)

wherein A represents a substituted or unsubstituted fused ring hydrocarbon units with two to five rings, preferably A represents a substituted or unsubstituted naphthyl group, a substituted or unsubstituted phenanthrenyl group, a substituted or unsubstituted anthracenyl group, a substituted or unsubstituted pyrenyl group, a substituted or unsubstituted chrysenyl group, a substituted or unsubstituted triphenylenyl group and a substituted or unsubstituted perylenyl group, X represents a divalent bridge selected from the atom or group consisting from O, S, $C(R_7)(R_8)$ and $N(R_9)$, m represents an integer of 0 to 5, n represents an integer of 0 to 3, p represents an integer of 0 to 8, $R_1$ to $R_6$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

5. The organic material according to claim 4, wherein A is represented by the following formulas:

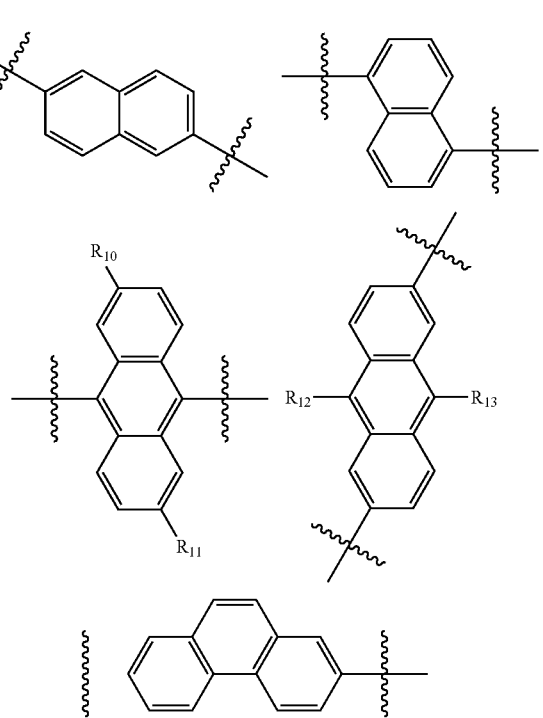

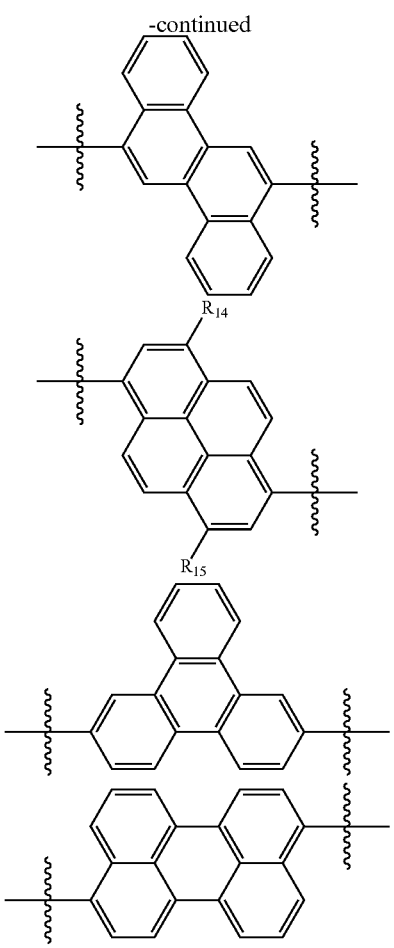

wherein $R_{10}$ to $R_{15}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

6. The organic material according to claim 4, when m represents an integer of 1, preferably $R_1$ and $R_4$ are represented by the following formula (2); when m represents an integer of 2, $R_1$ and $R_4$ are each independently in adjacent position, preferably $R_1$ and $R_4$ are represented by the following formula (3)

formula (2)

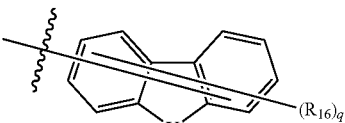

formula (3)

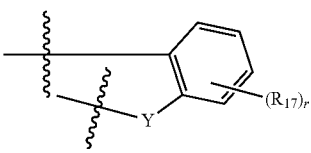

wherein Y represents a divalent bridge selected from the atom or group consisting from O, S and $N(R_{18})$, q represents an integer of 0 to 8, r represents an integer of 0 to 4, $R_{16}$ to $R_{18}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

7. The organic material according to claim 4, wherein the organic material formula (4) to formula (6) are represented by the following formula (7) to formula (18):

formula(7)

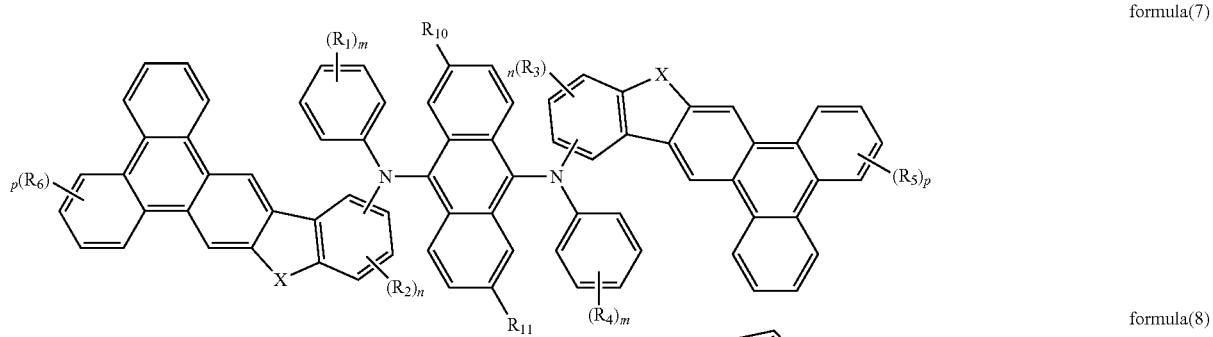

formula(8)

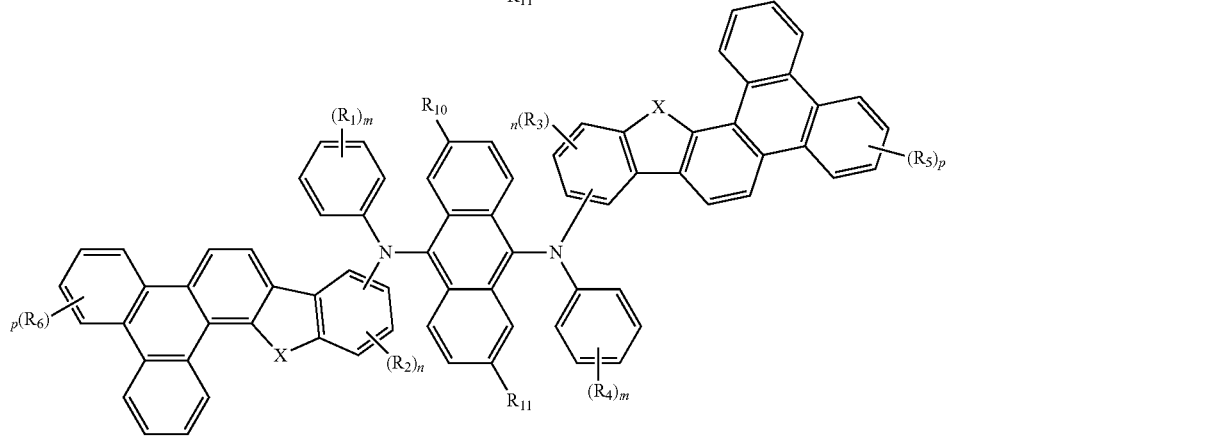

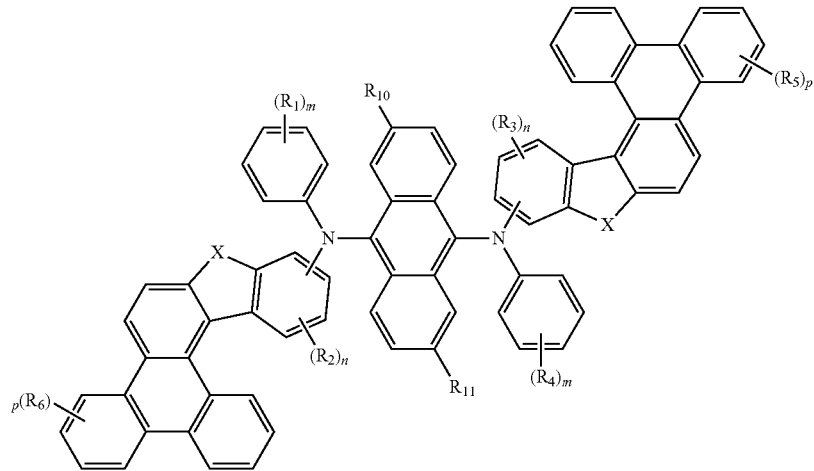
formula(9)
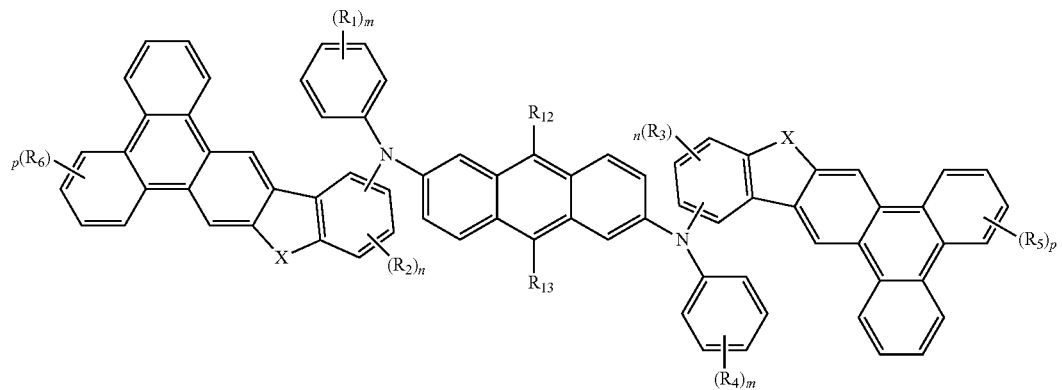
formula(10)
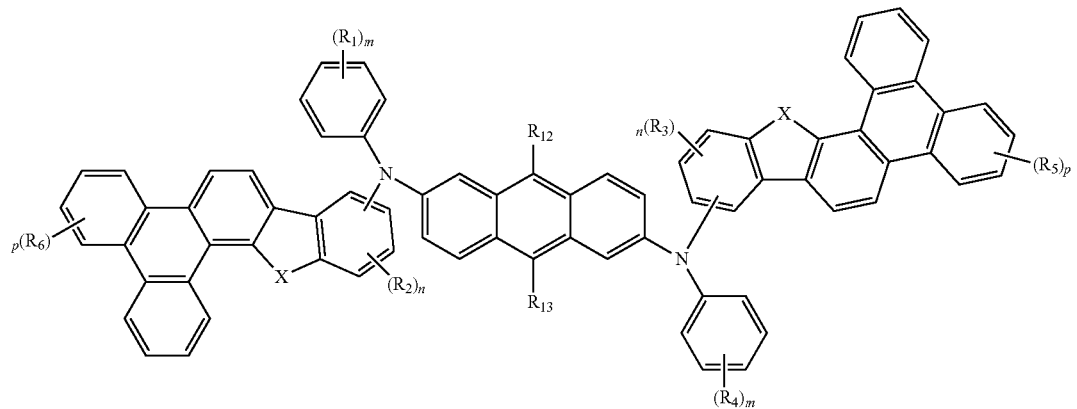
formula(11)

-continued
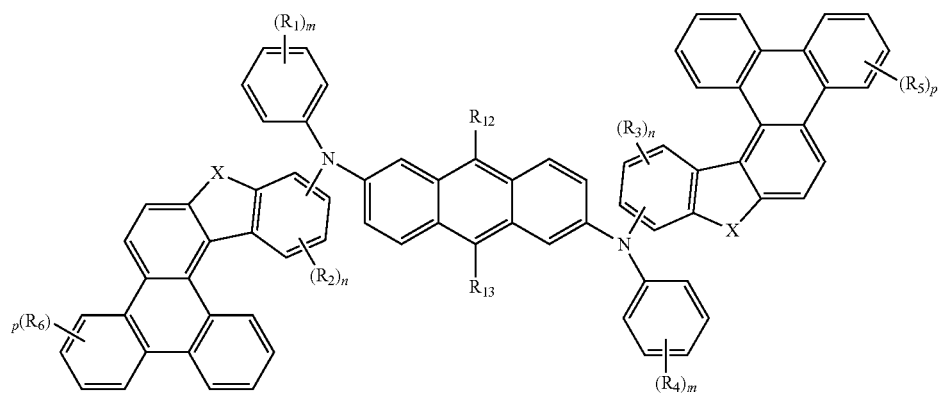
formula(12)
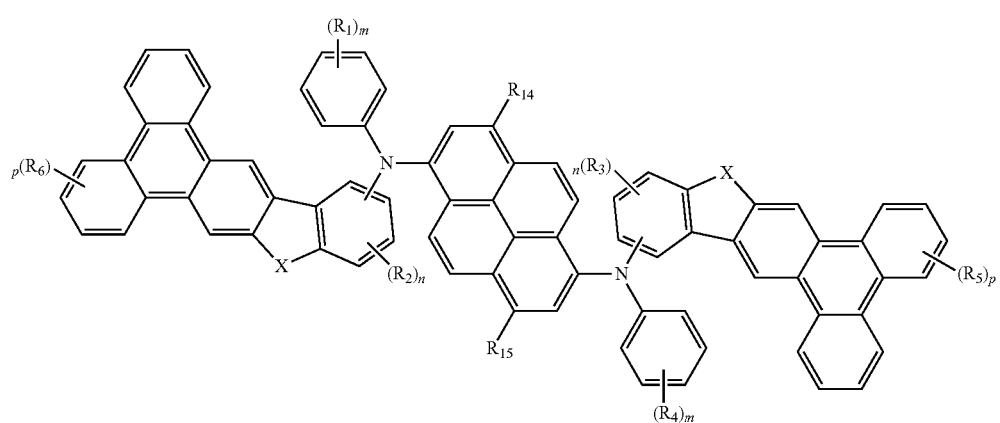
formula(13)
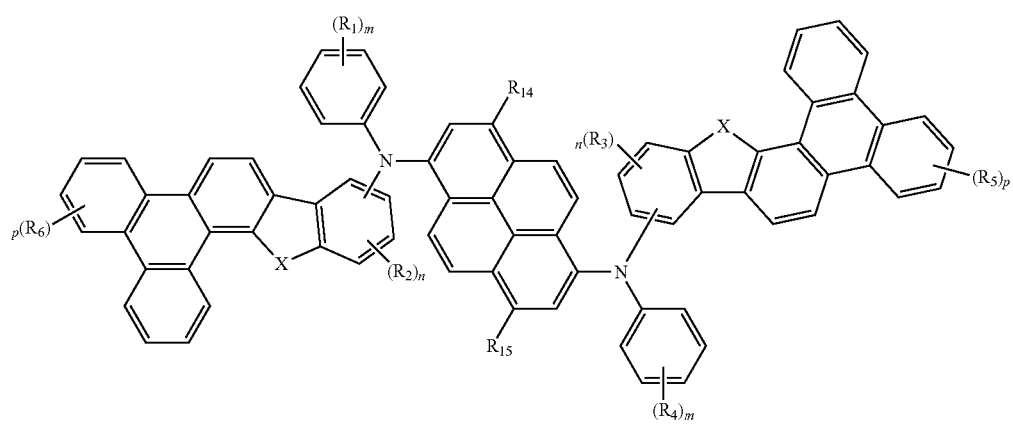
formula(14)
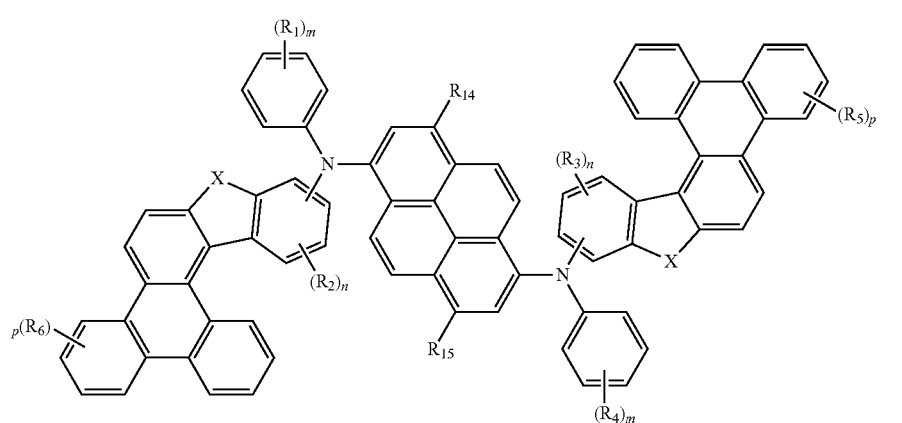
formula(15)

formula(16)

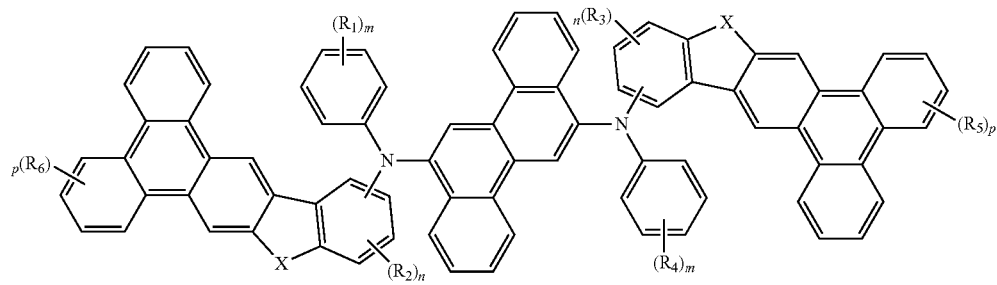

formula(17)

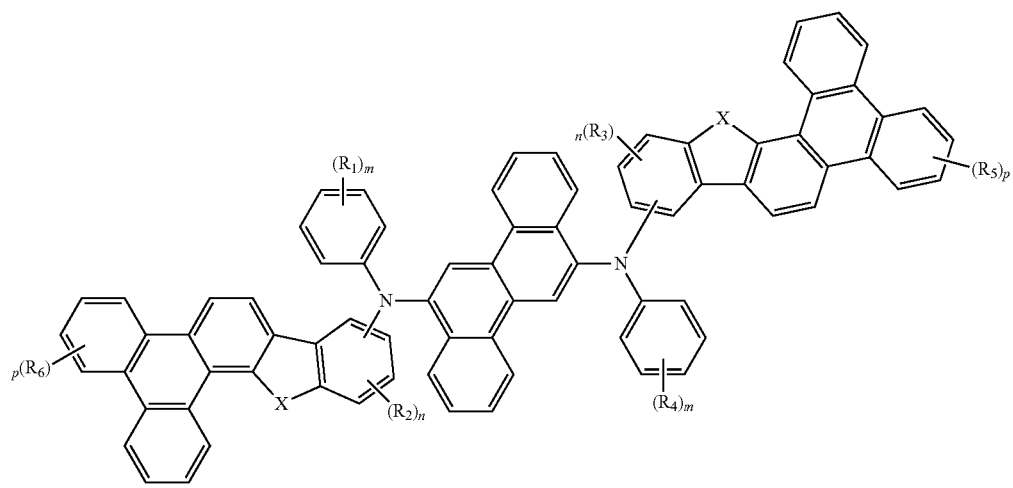

formula(18)

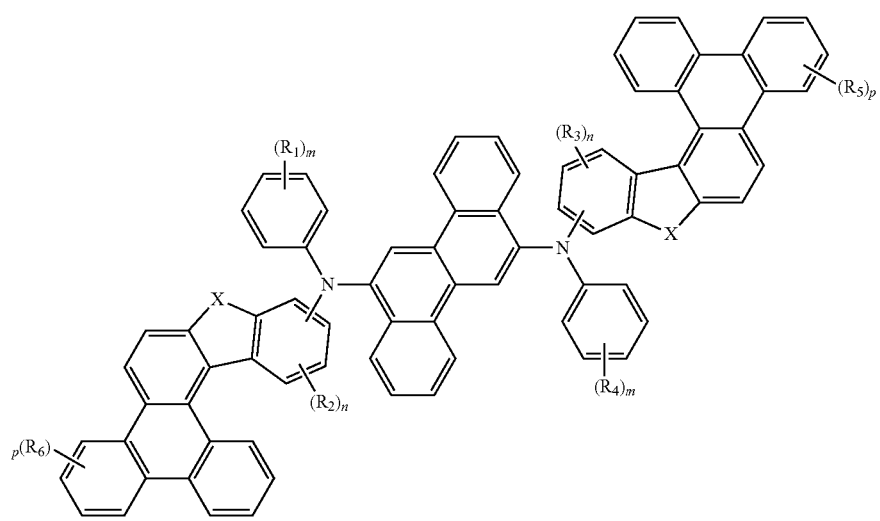

wherein X represents a divalent bridge selected from the atom or group consisting from O, S, C(R$_7$)(R$_8$) and N(R$_9$), m represents an integer of 0 to 5, n represents an integer of 0 to 3, p represents an integer of 0 to 8, R$_1$ to R$_{15}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

8. The organic material according to claim 7, when m represents an integer of 1, preferably R$_1$ and R$_4$ are represented by the following formula (2); when m represents an integer of 2, R$_1$ and R$_4$ are each independently in adjacent position, preferably R$_1$ and R$_4$ are represented by the following formula (3)

formula (2)

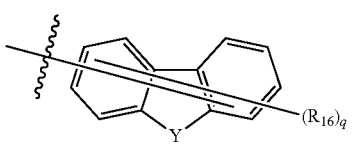

-continued formula (3)

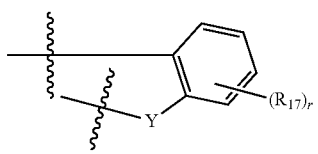

wherein Y represents a divalent bridge selected from the atom or group consisting from O, S and N(R$_{18}$), q represents an integer of 0 to 8, r represents an integer of 0 to 4, R$_{16}$ to R$_{18}$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

9. The organic material according to claim 1, wherein the fluorescent emitting guest is selected from the formula consisting of:

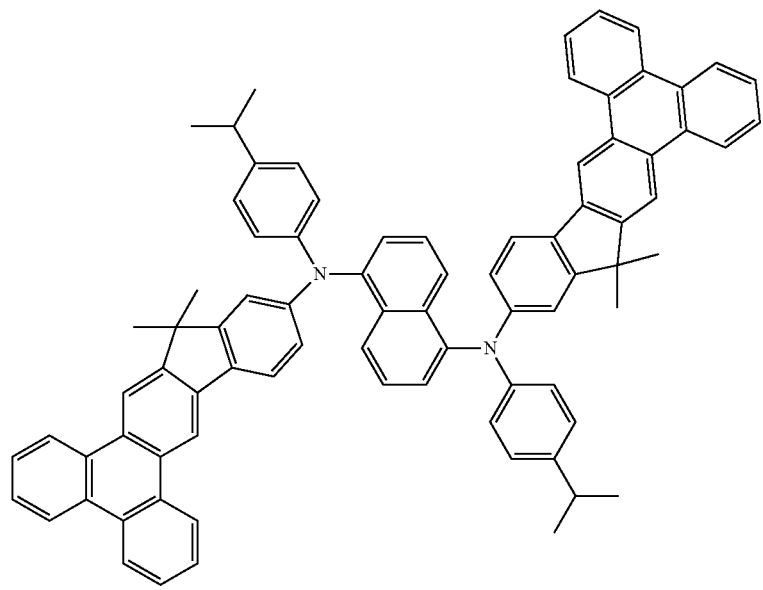

EX1

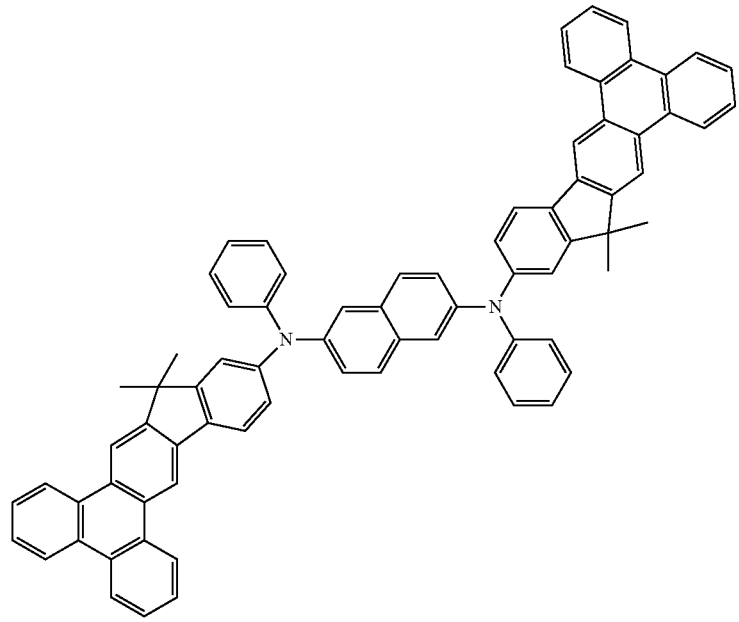

EX2

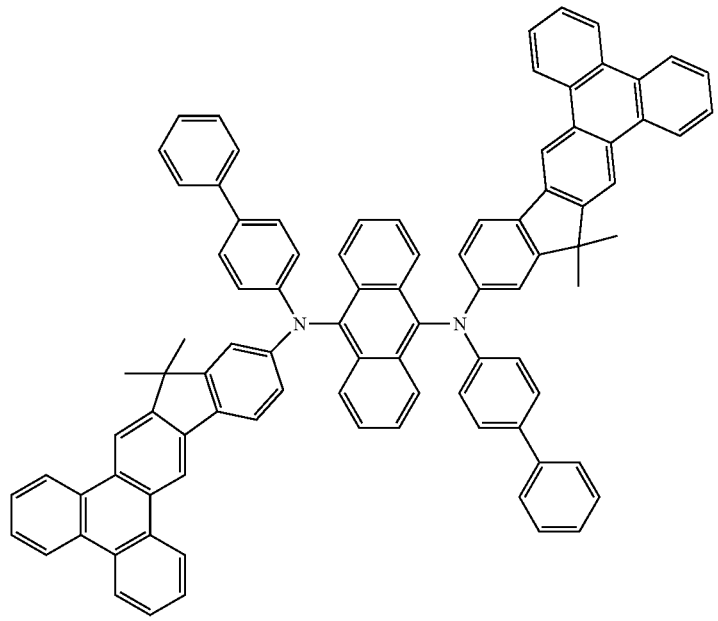
EX3
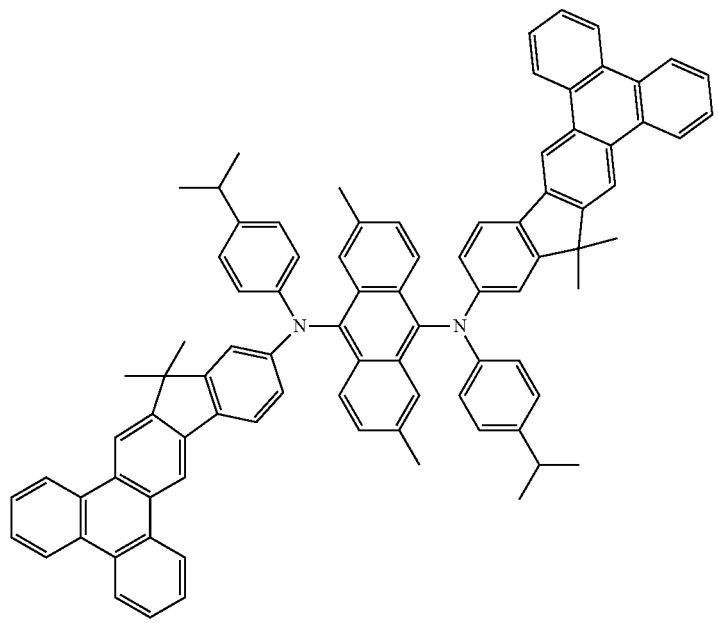
EX4

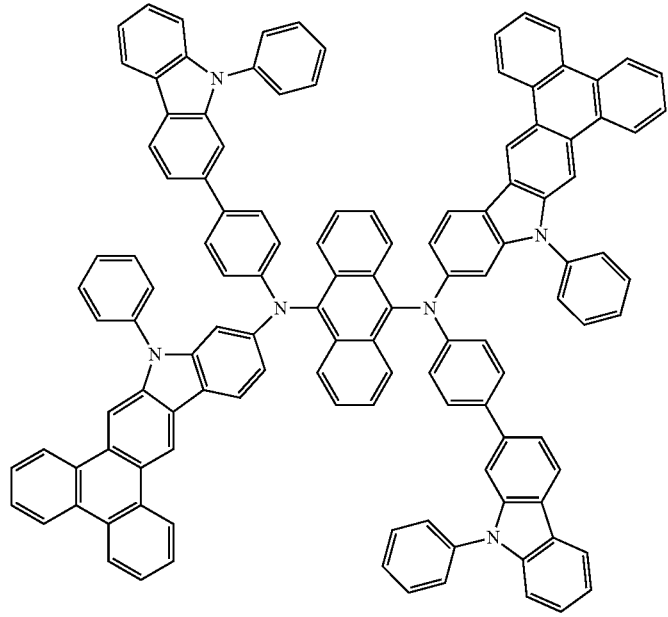
EX5
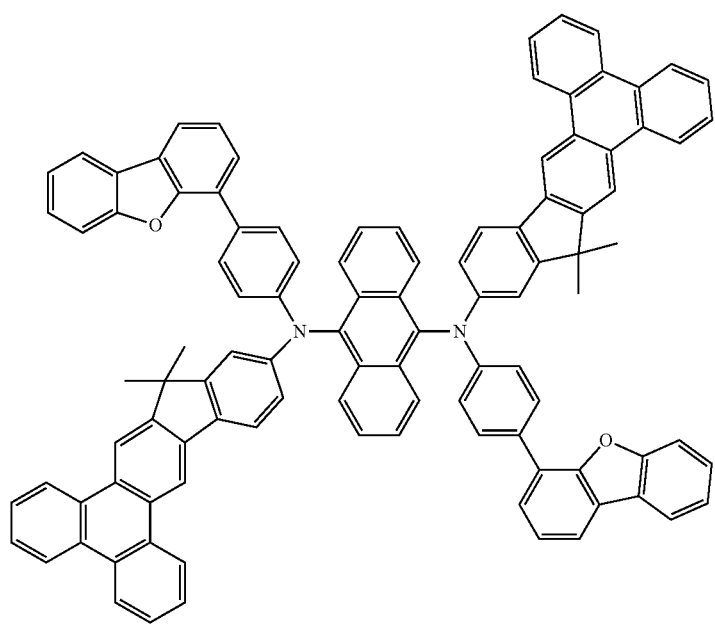
EX6

EX7
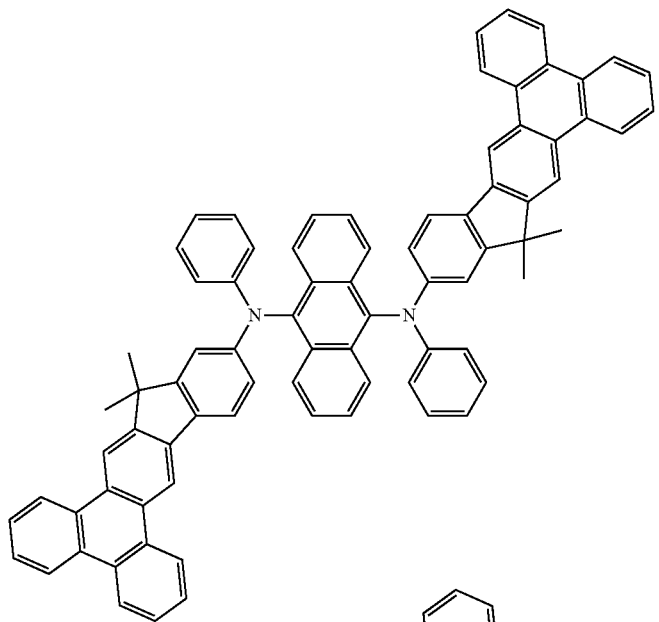
EX8
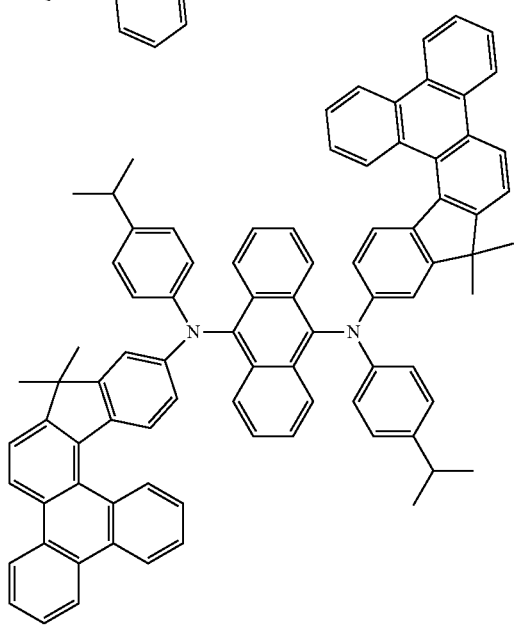
EX9
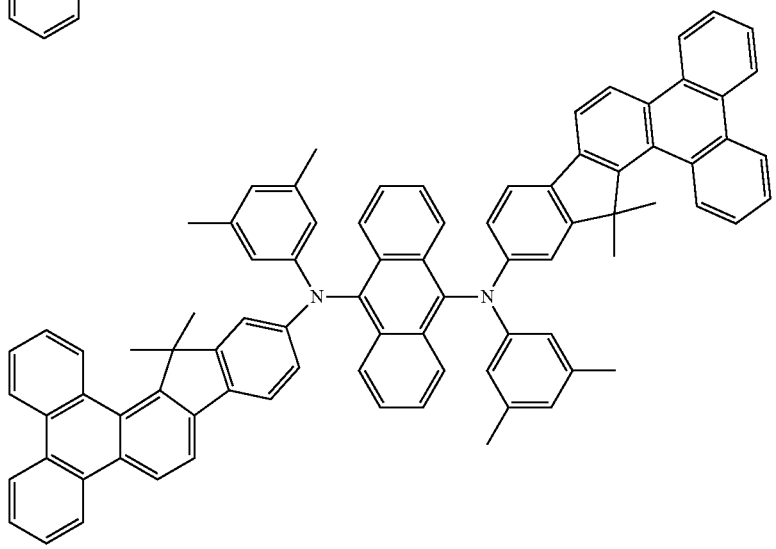

-continued
EX10
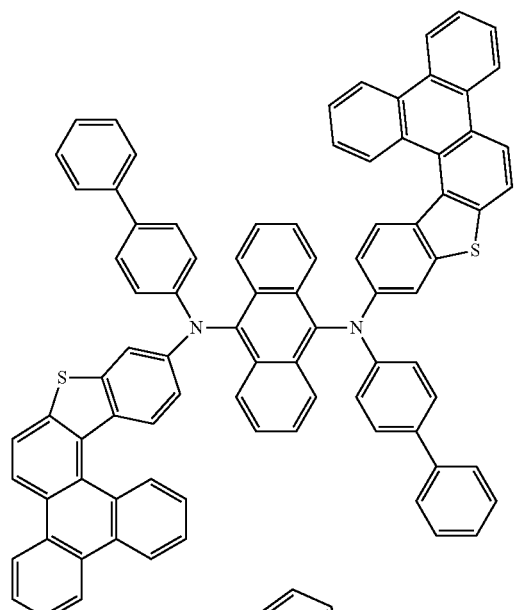
EX11
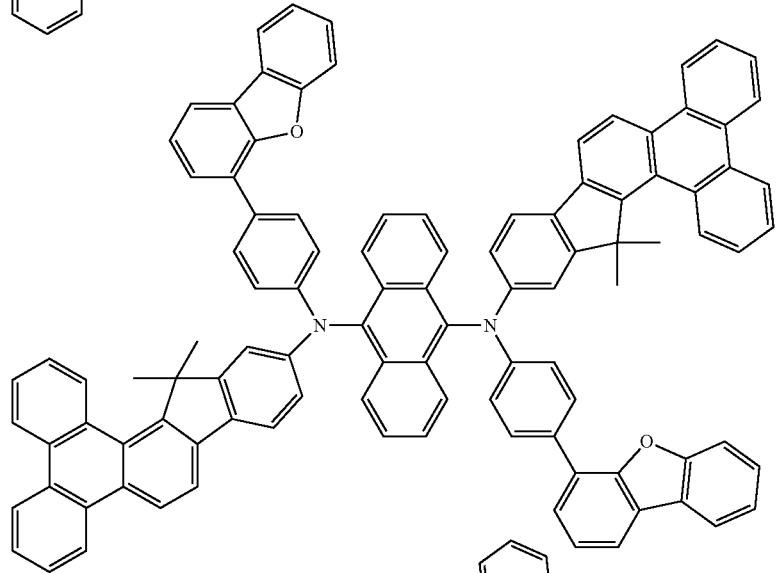
EX12
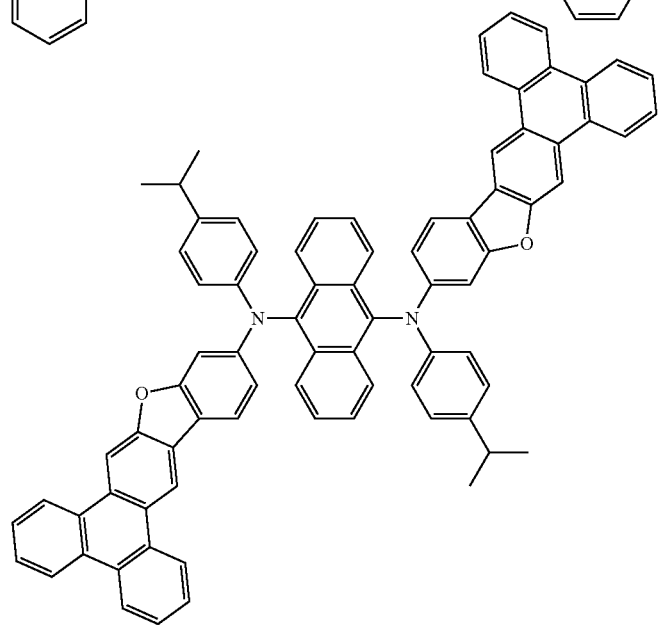

-continued
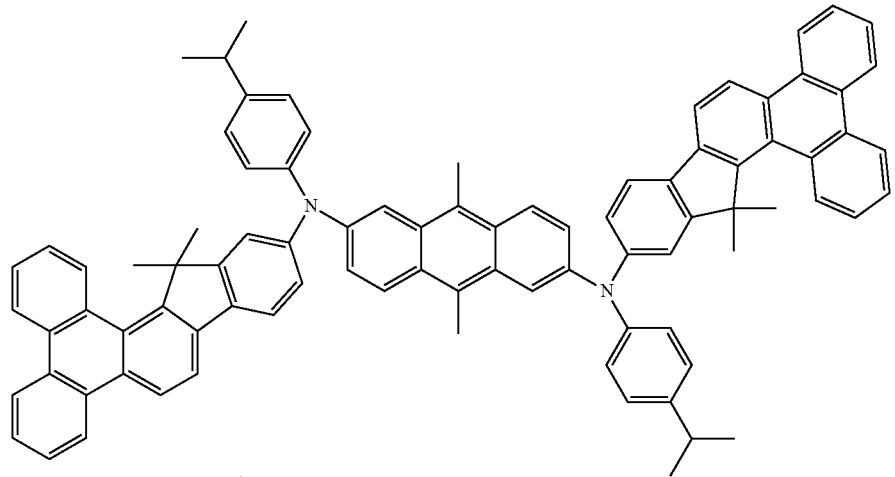
EX13
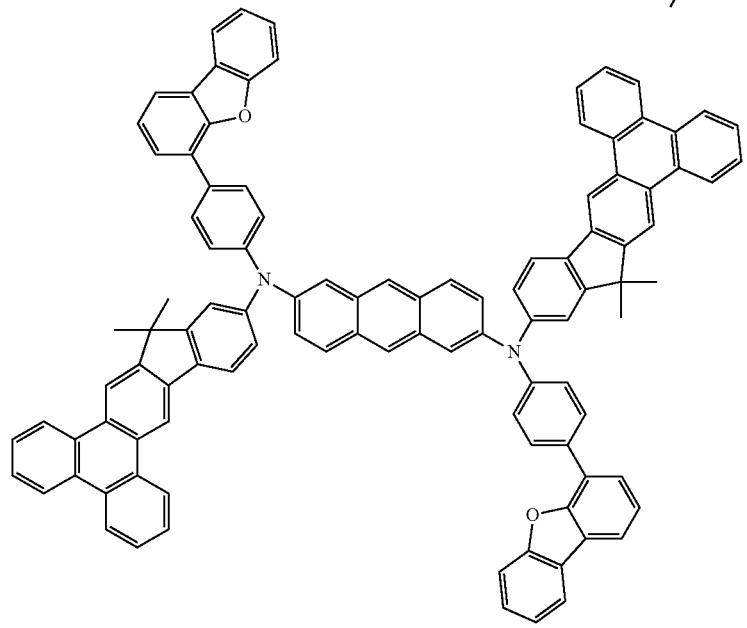
EX14
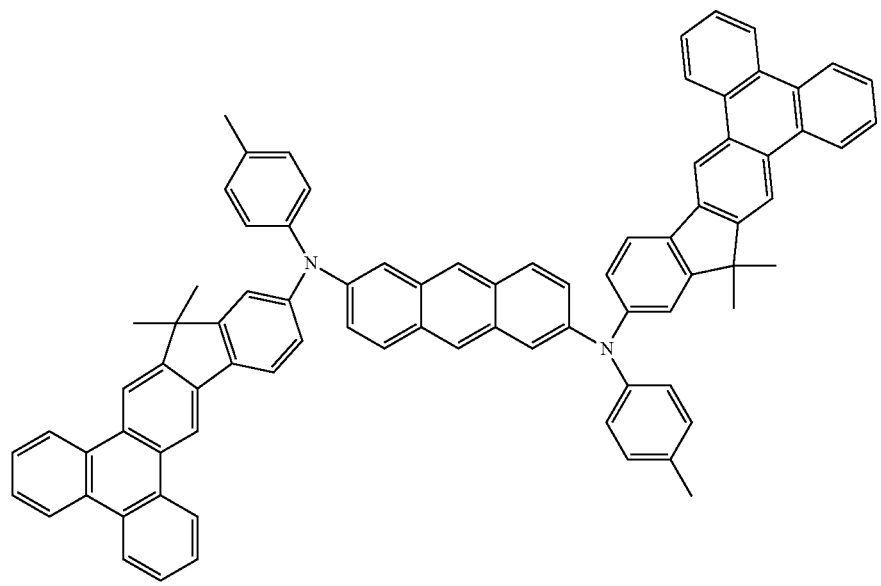
EX15

EX16
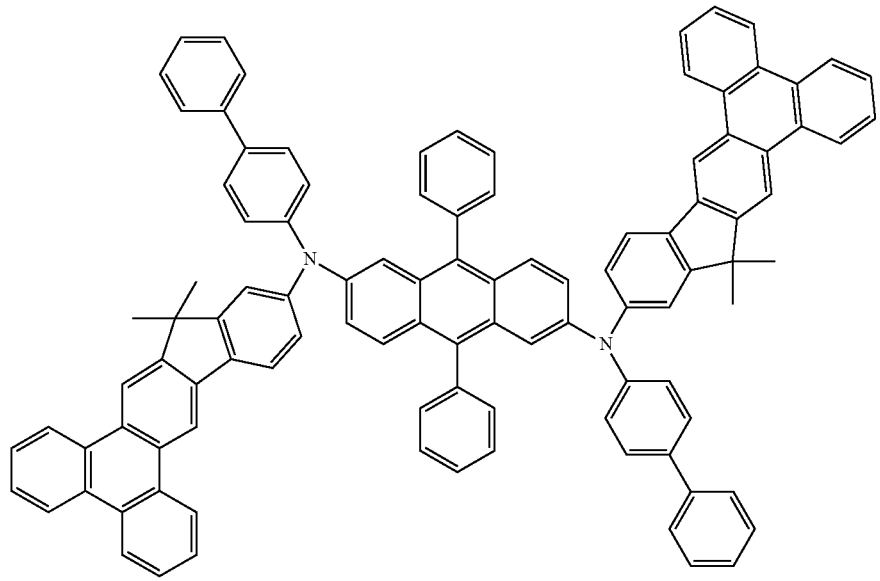
EX17
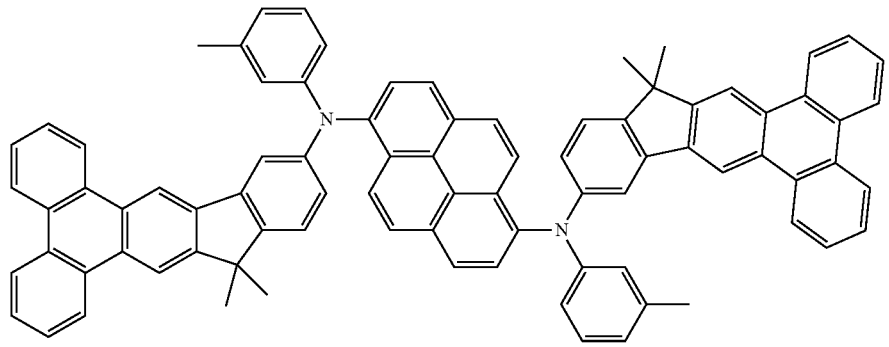
EX18
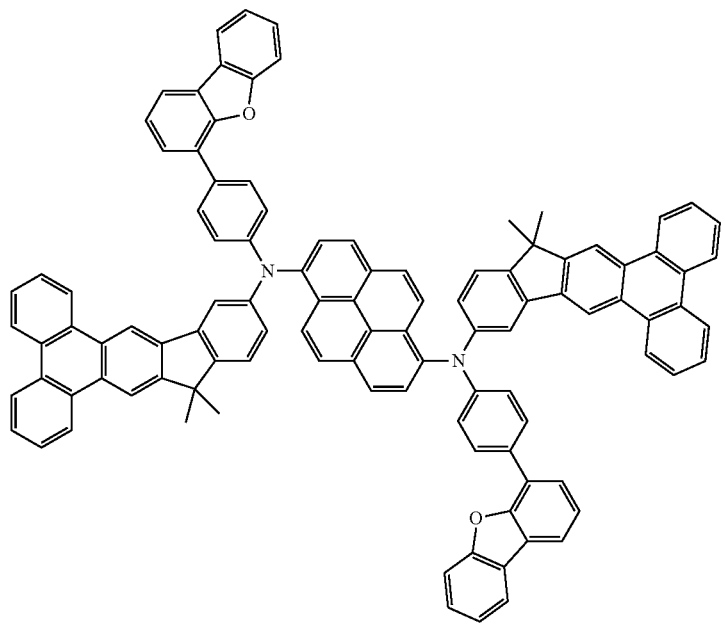

-continued
EX19
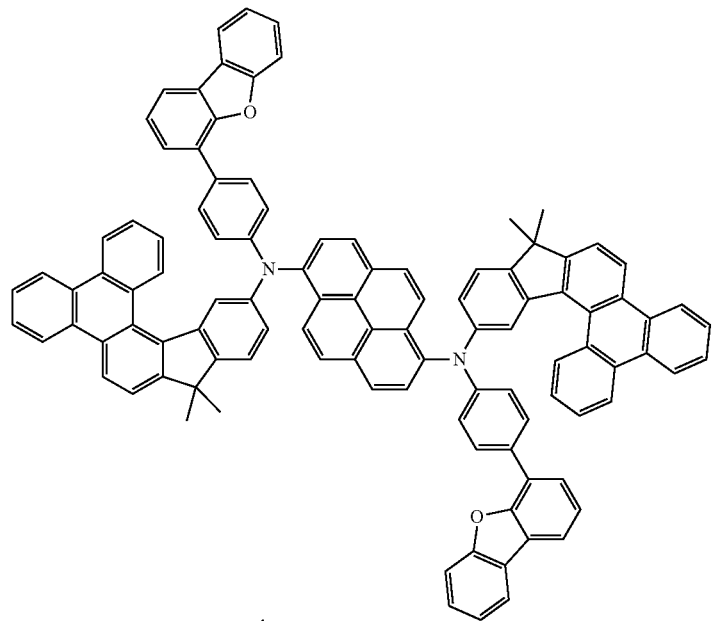
EX20
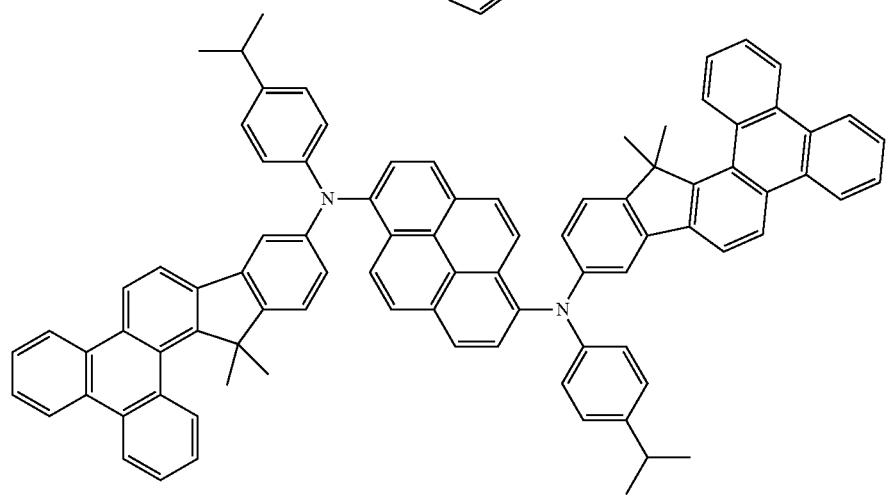
EX21
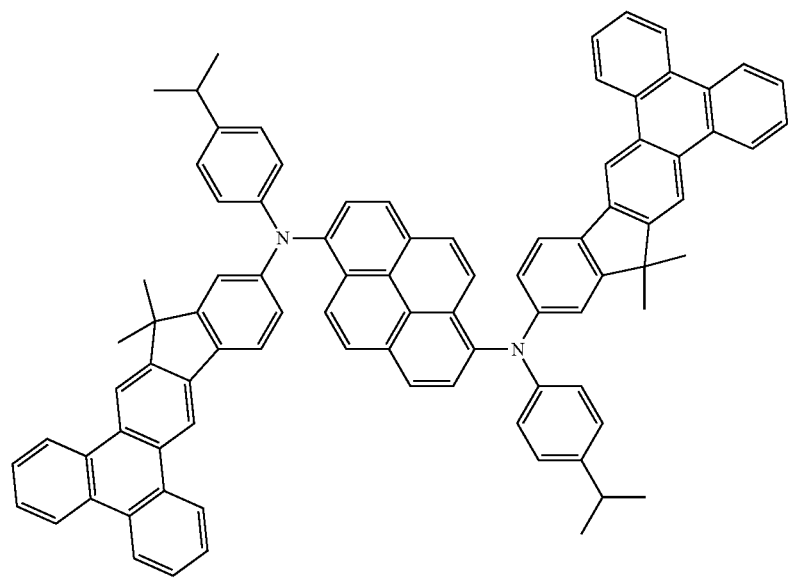

-continued
EX22
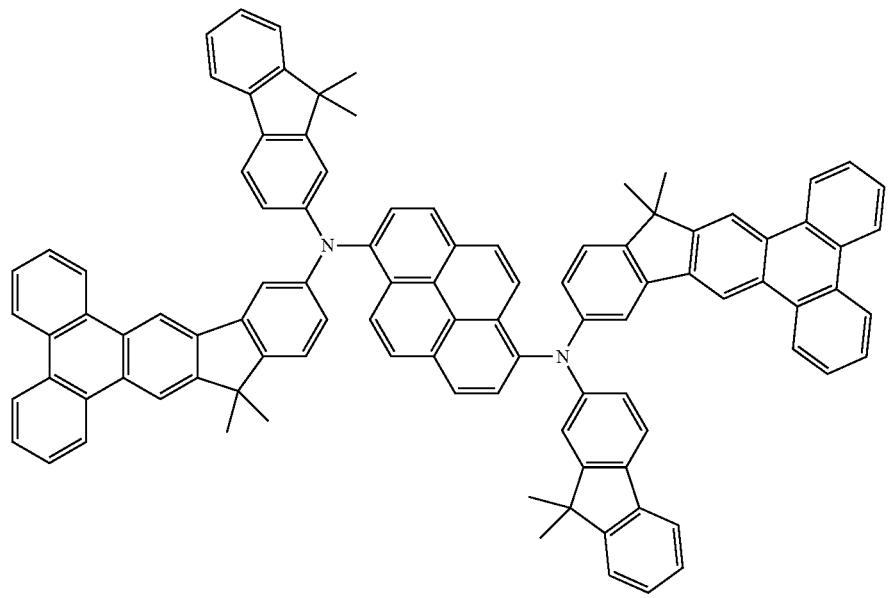
EX23
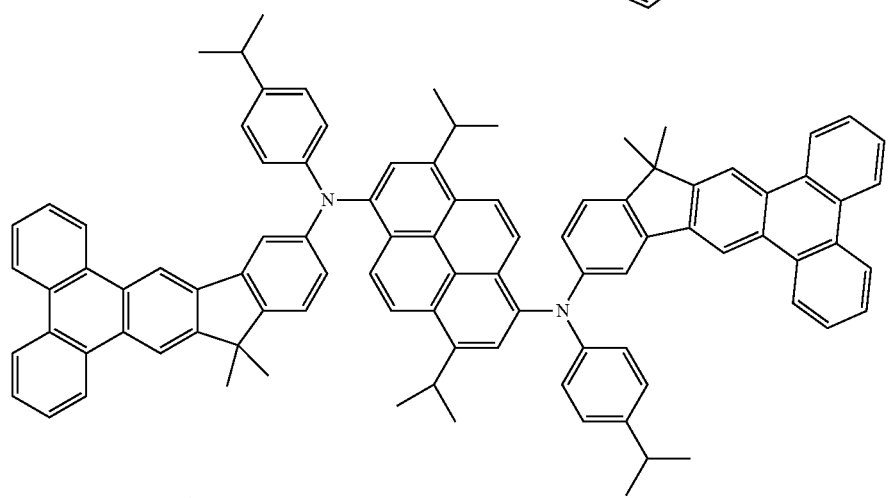
EX24
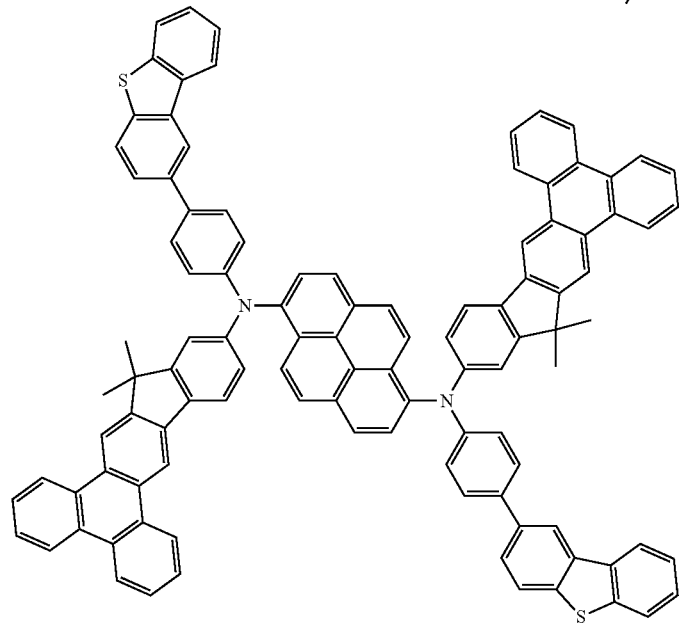

EX25
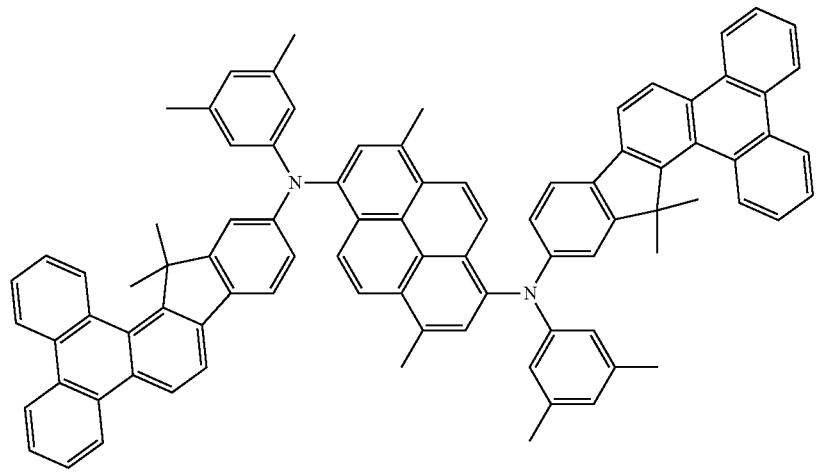
EX26
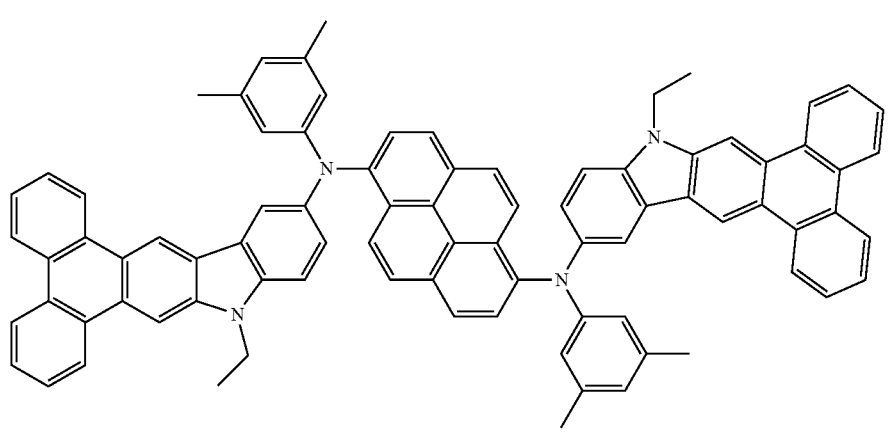
EX27
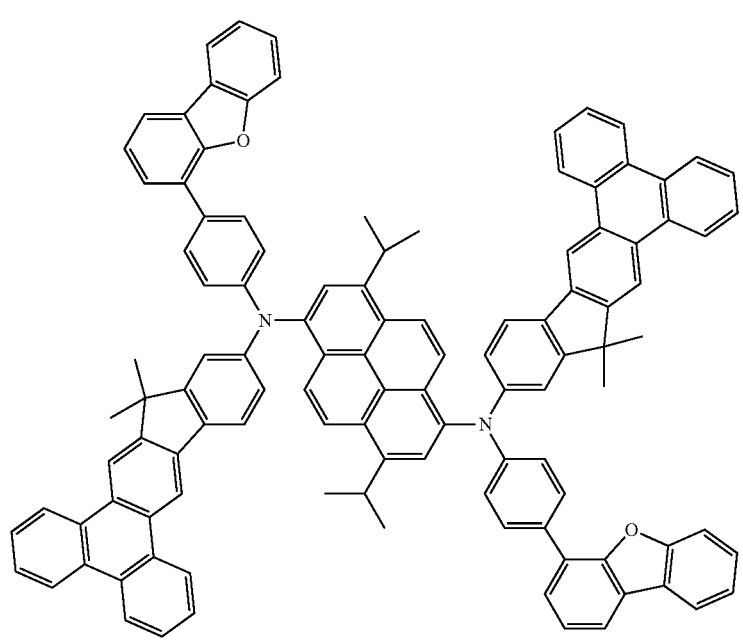

-continued
EX28
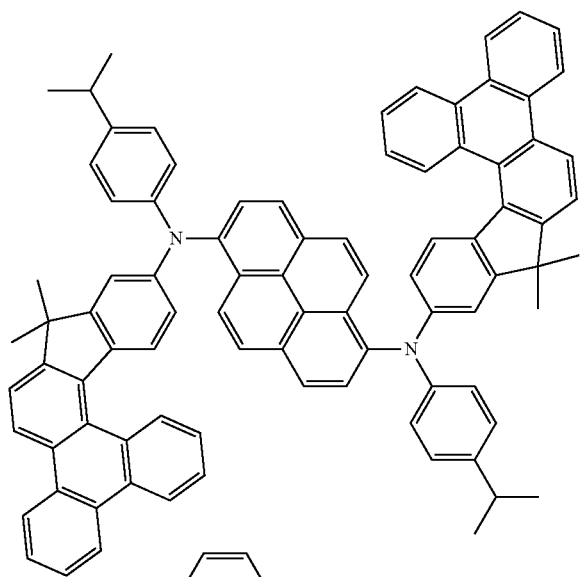
EX29
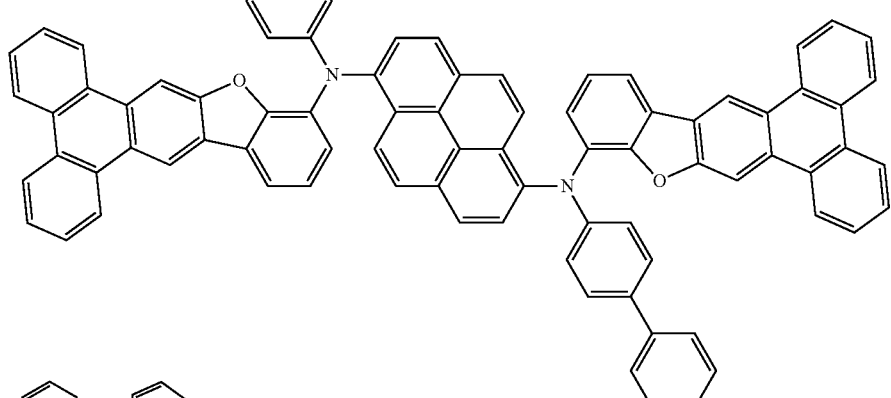
EX30
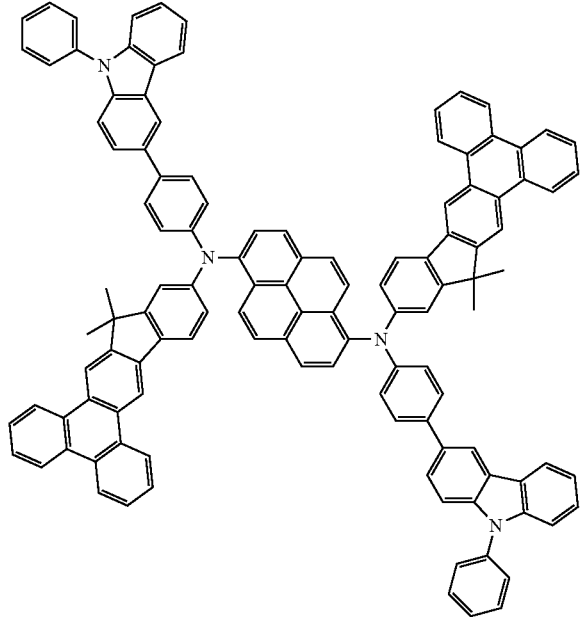

-continued
EX31
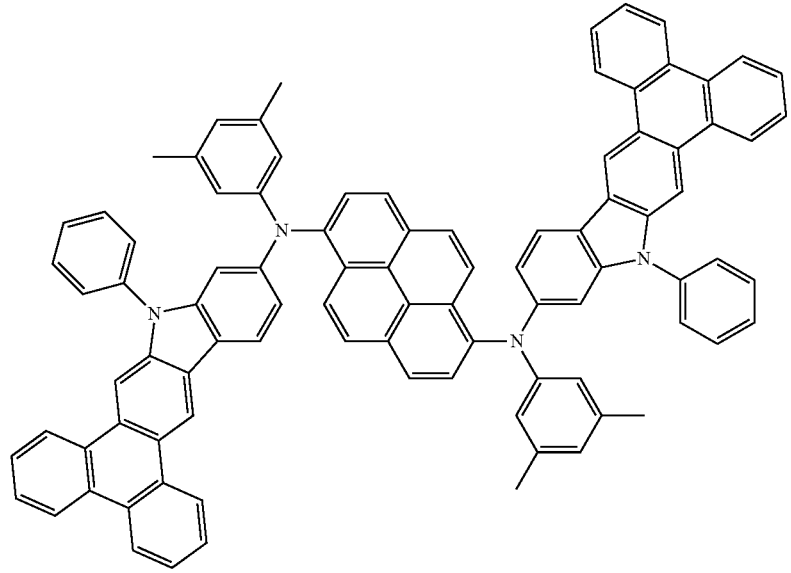
EX32
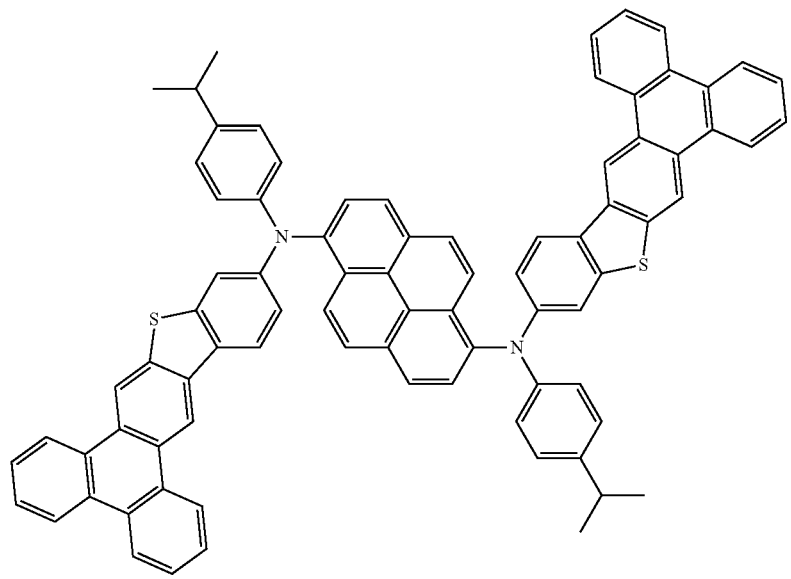
EX33
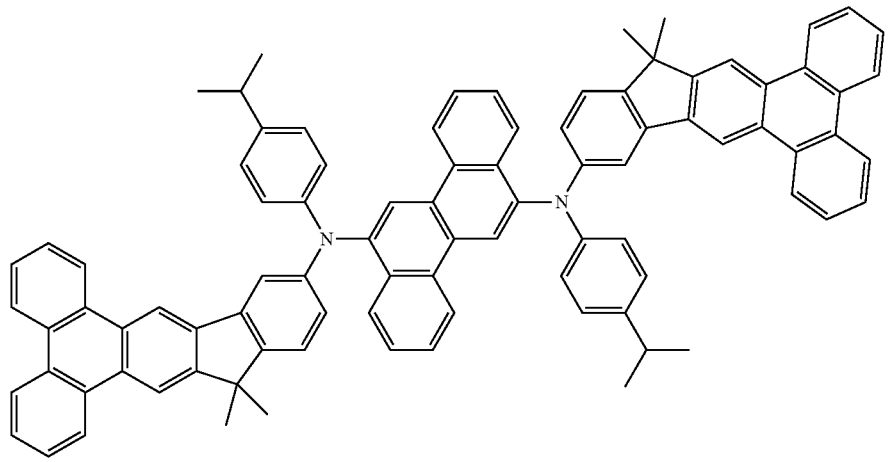

-continued
EX34
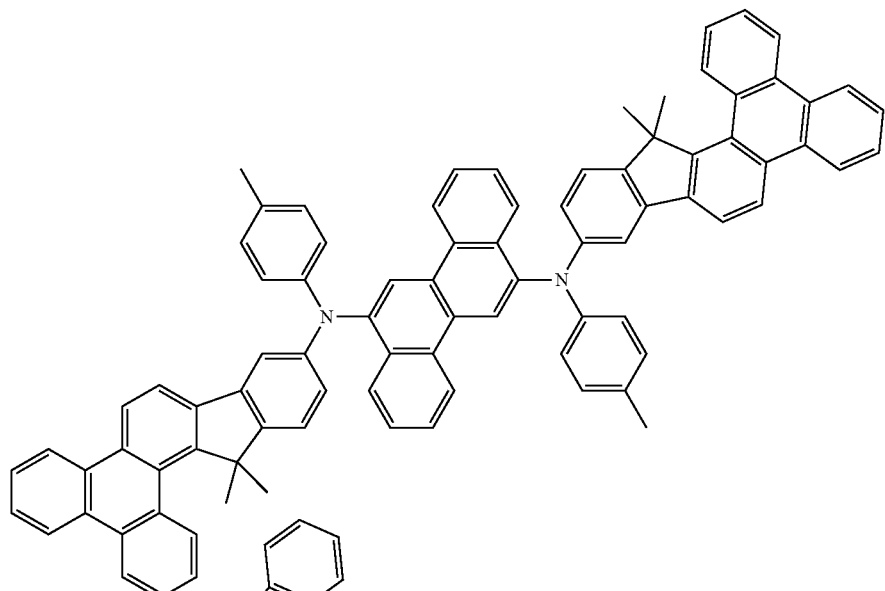
EX35
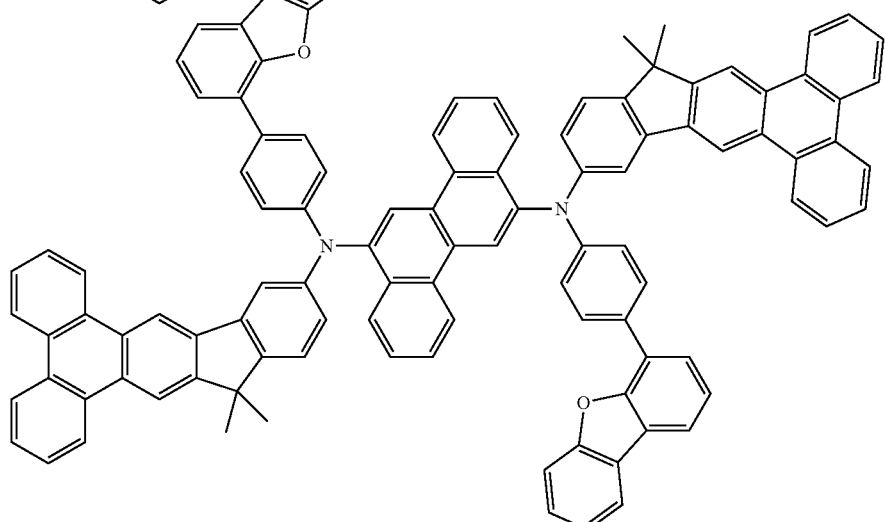
EX36
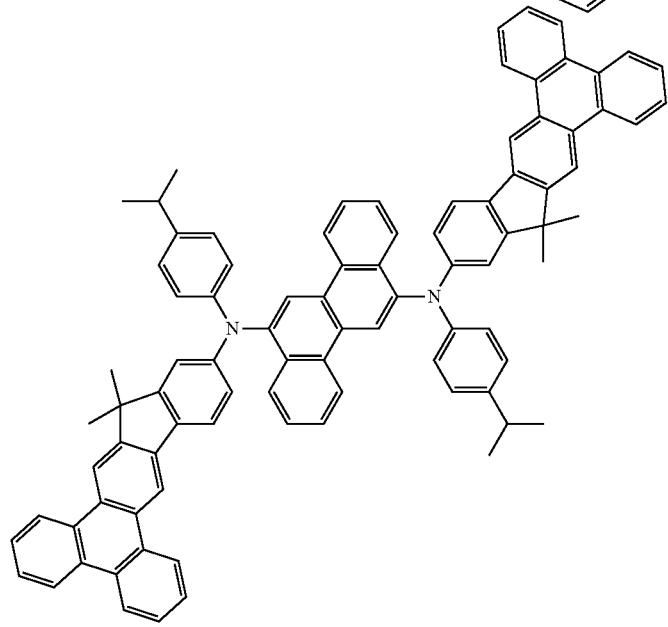

EX37
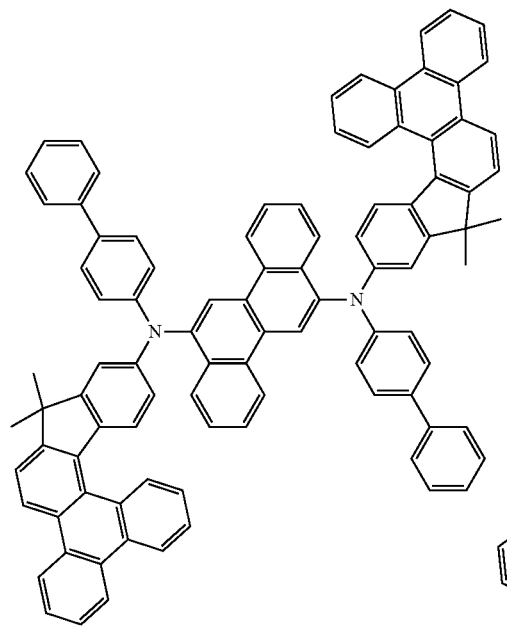
EX38
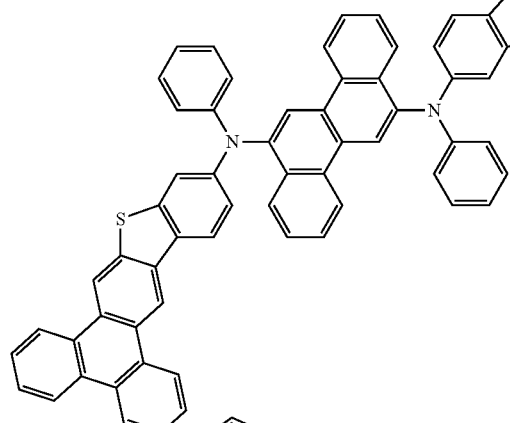
EX39
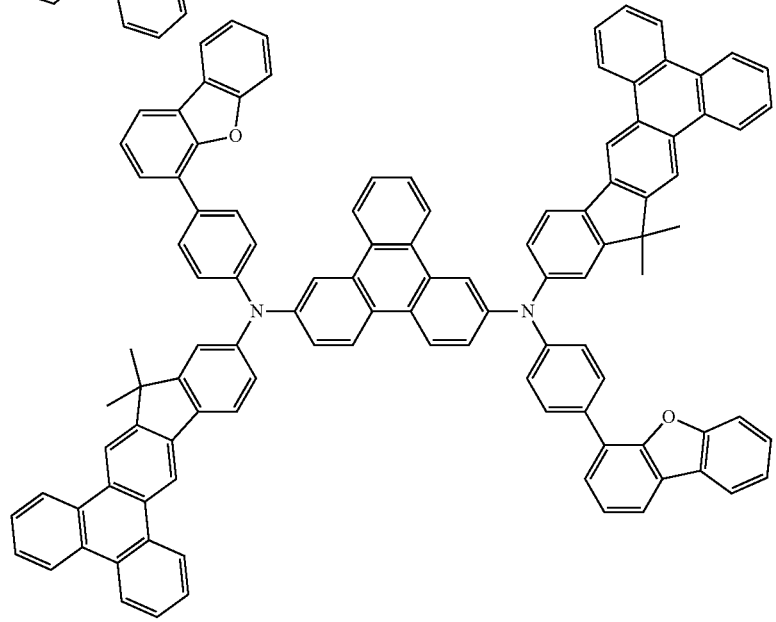

EX40
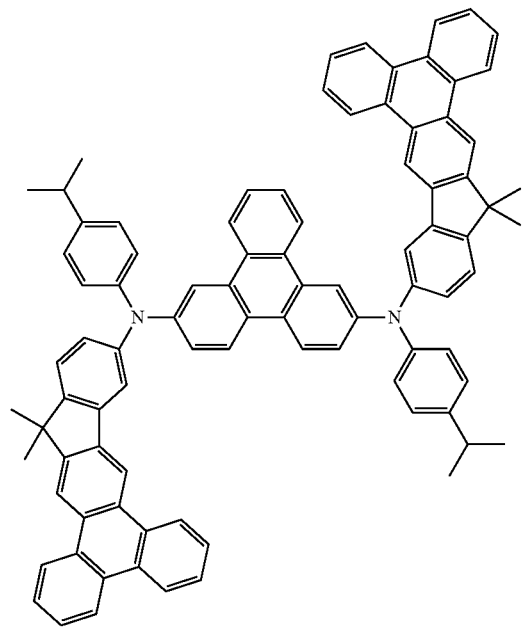
EX41
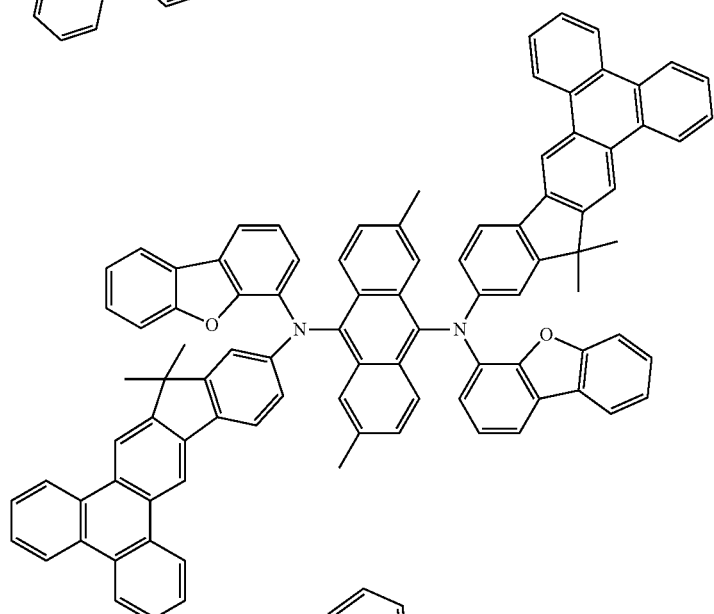
EX42
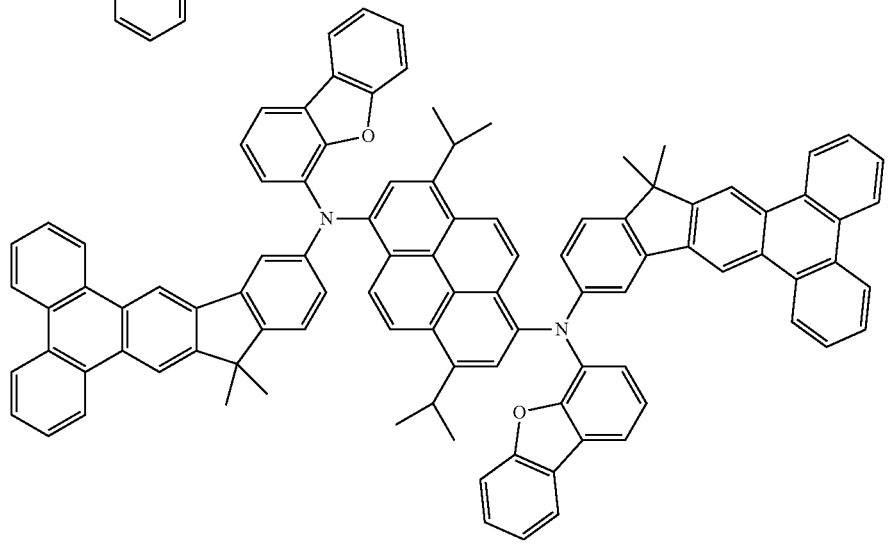
and

EX43

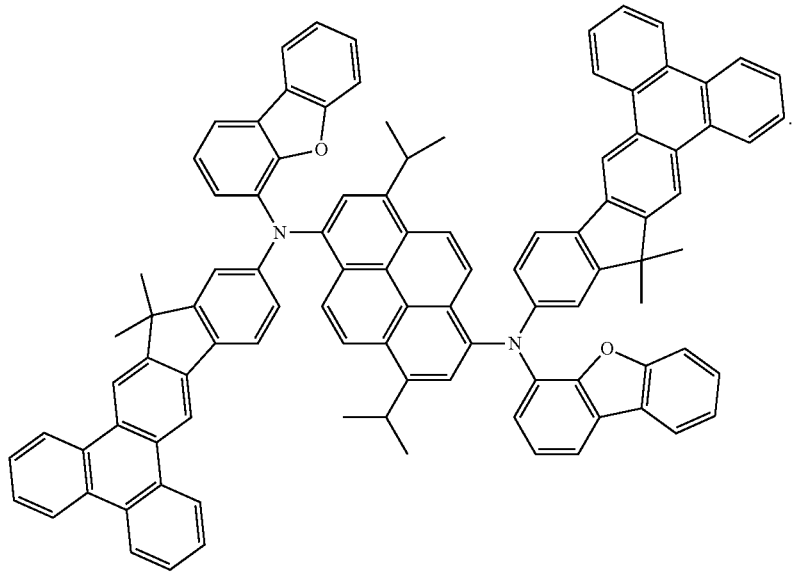

10. A organic electroluminescent device comprising a pair of electrodes consisting of a cathode and an anode and between the pairs of electrodes comprising at least a layer of the organic material with a general formula (1) according to claim 1.

11. The organic electroluminescent device according to claim 10, wherein the at least one layer of the organic material comprises a fluorescent emitting guest comprising the organic material with a general formula (1).

12. The organic electroluminescent device according to claim 11, wherein the fluorescent emitting guest comprising the organic material with a general formula (4) to formula (6)

formula(4)
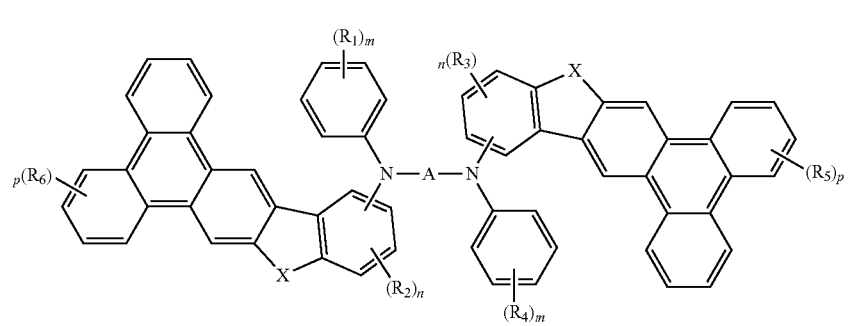

formula(5)
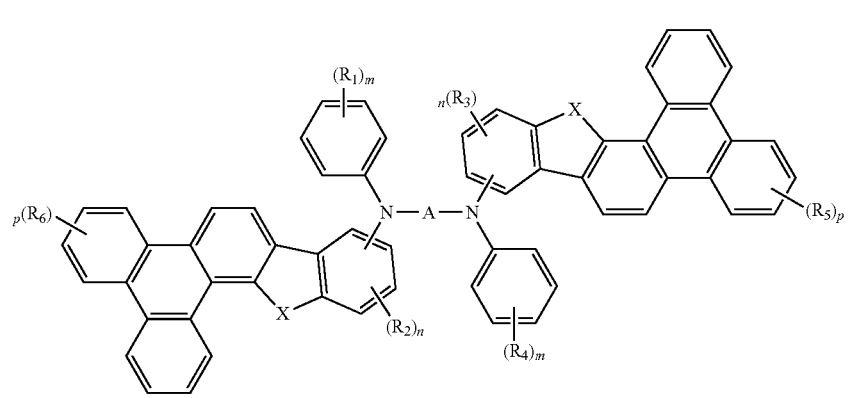

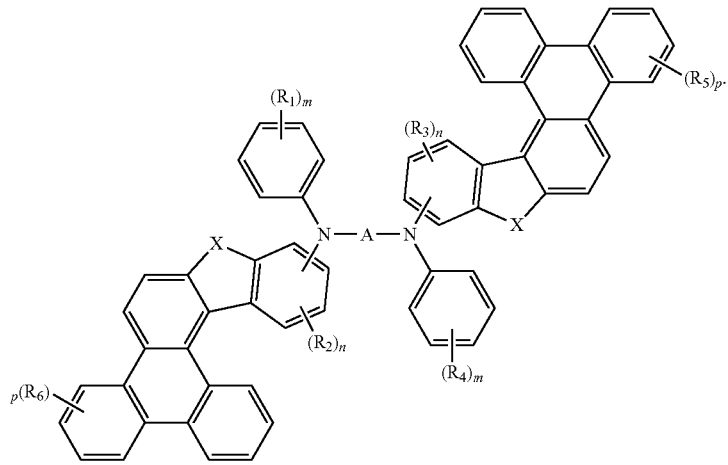
formula(6)
13. The organic electroluminescent device according to claim 11, wherein the fluorescent emitting guest comprising the organic material with a general formula (7) to formula (18)
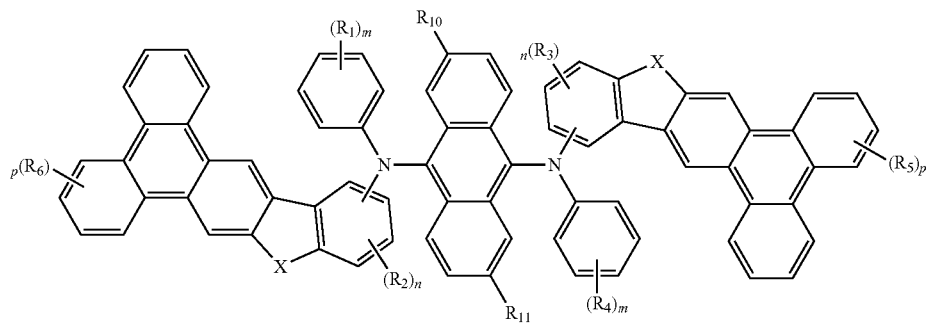
formula(7)
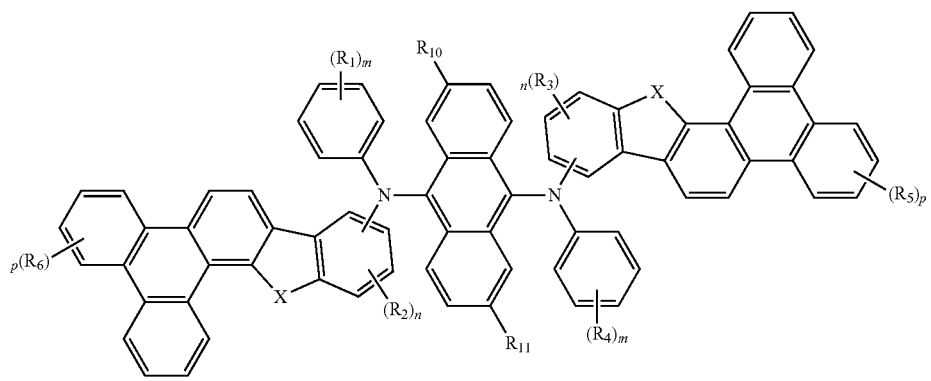
formula(8)

formula(9)
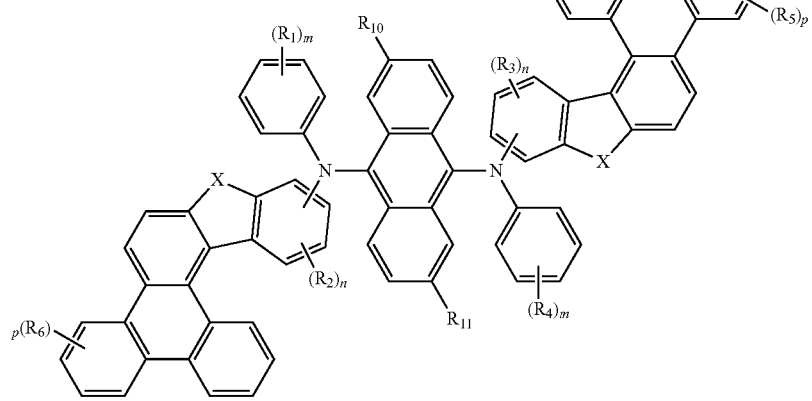
formula(10)
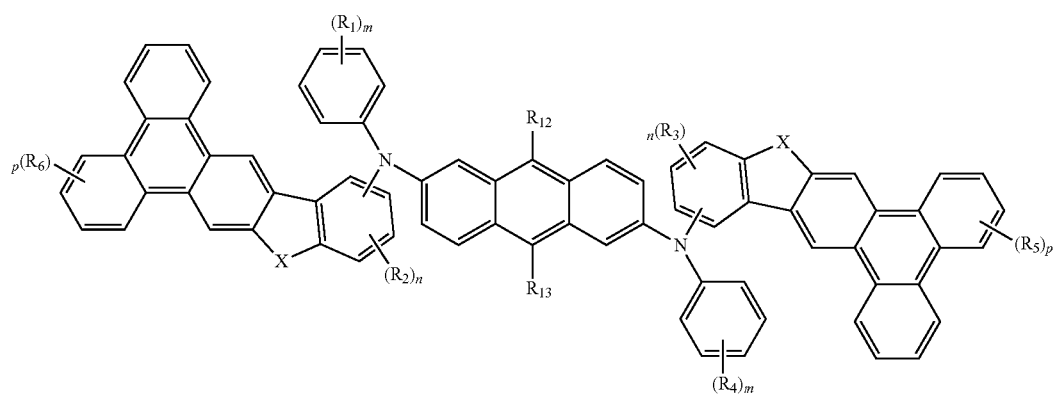
formula(11)
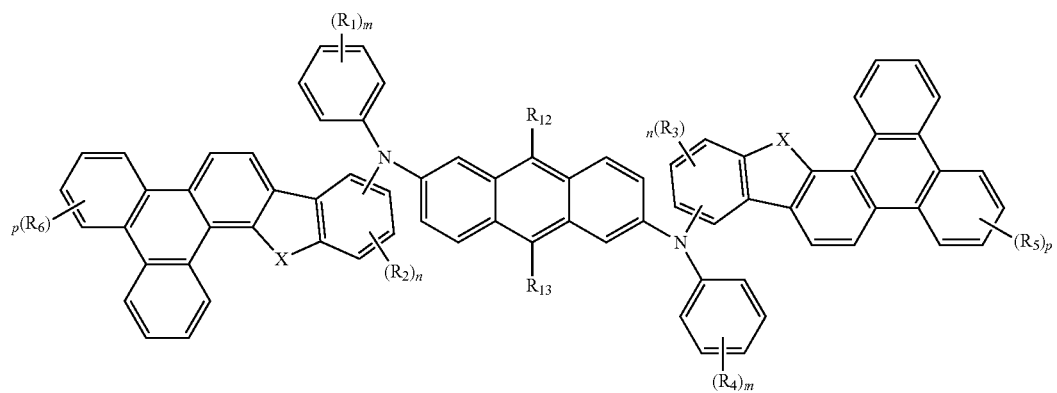
formula(12)
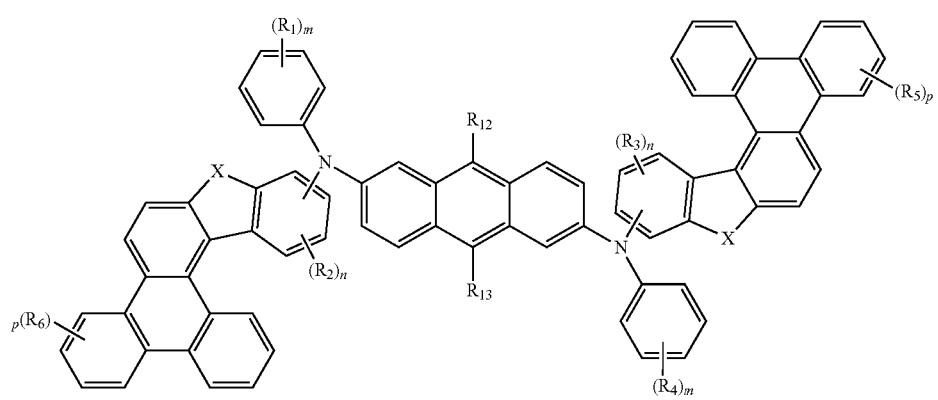

formula(13)
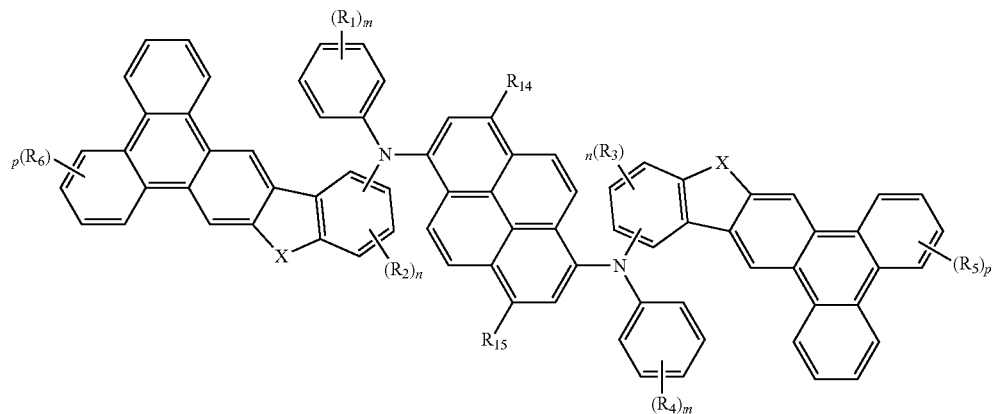
formula(14)
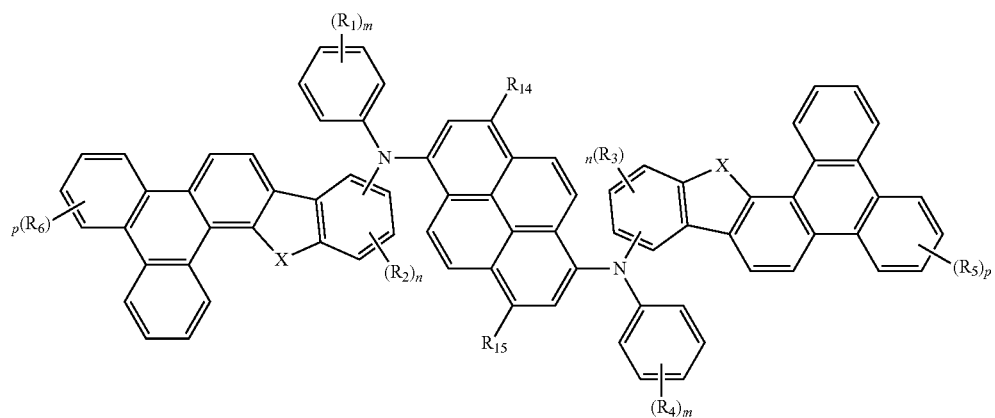
formula(15)
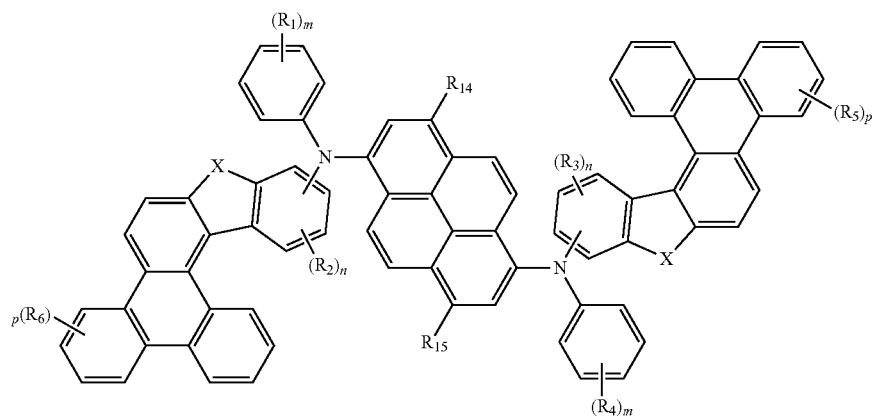
formula(16)
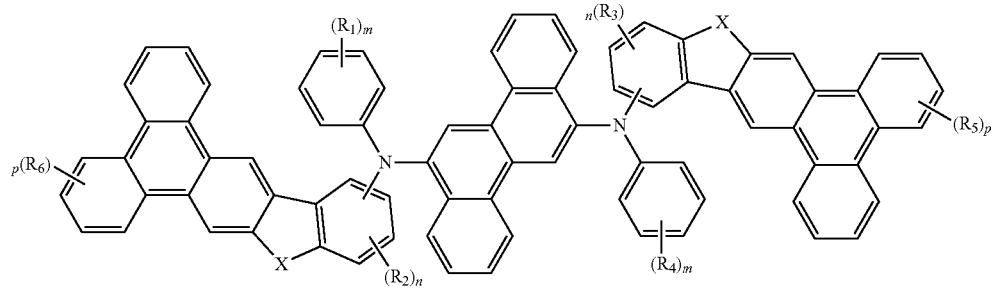

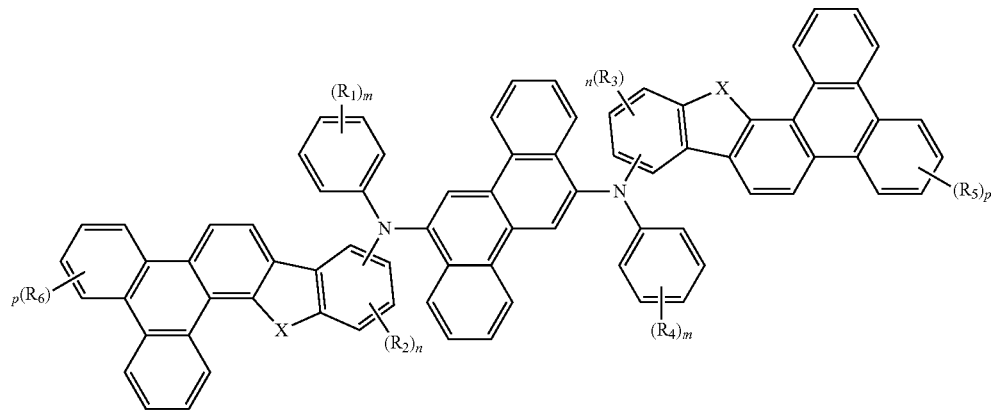
formula(17)
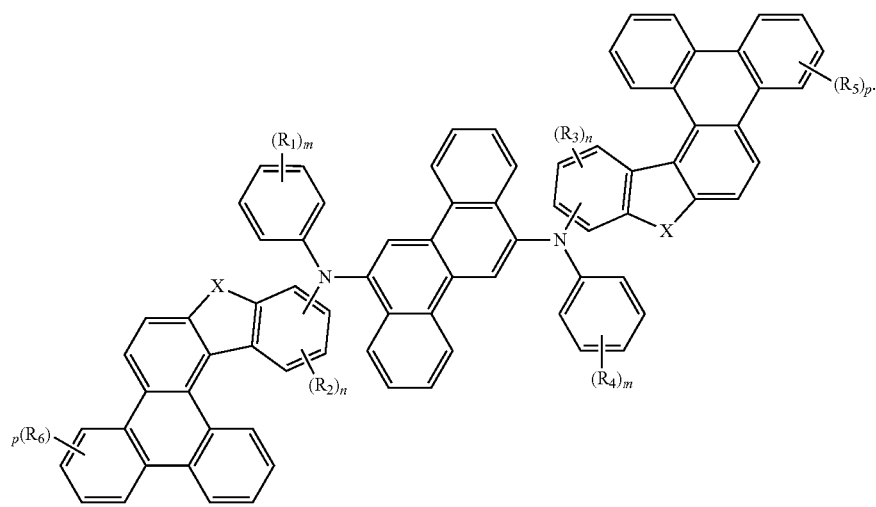
formula(18)
14. The organic electroluminescent device according to claim 11, wherein the fluorescent emitting guest comprising the following formulas:
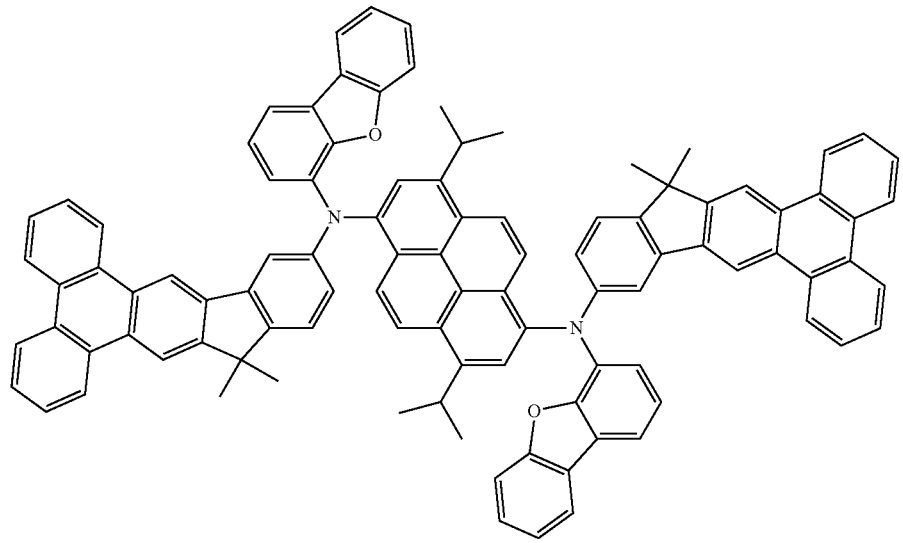

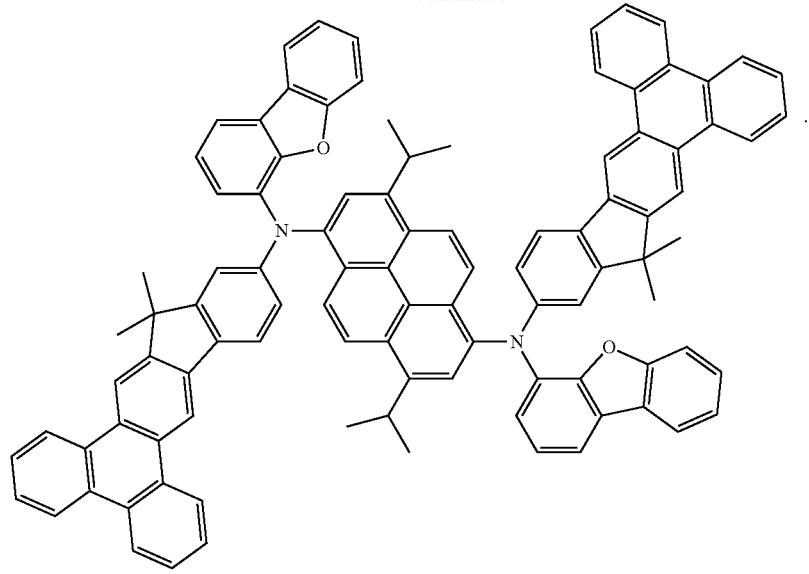
15. The organic electroluminescent device according to claim 11, wherein the fluorescent emitting host comprising the following formulas:
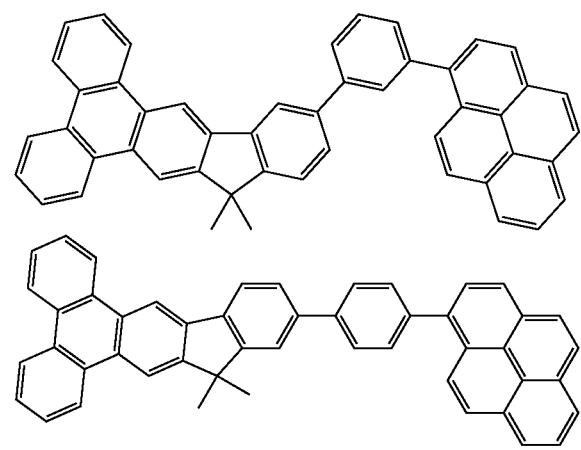
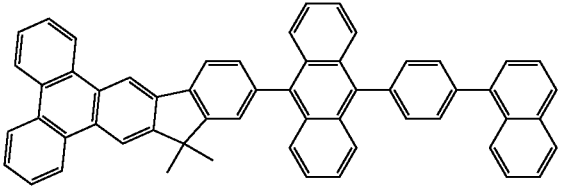
* * * * *